(12) United States Patent
Mhlanga et al.

(10) Patent No.: US 9,663,833 B2
(45) Date of Patent: May 30, 2017

(54) SINGLE CELL BASED REPORTER ASSAY TO MONITOR GENE EXPRESSION PATTERNS WITH HIGH SPATIO-TEMPORAL RESOLUTION

(75) Inventors: Musa Mhlanga, Paris (FR); Jost Enninga, Paris (FR); Philippe Sansonetti, Paris (FR); Ulf Nehrbass, Paris (FR)

(73) Assignee: INSTITUT PASTEUR, Paris (FR)

( * ) Notice: Subject to any disclaimer, the term of this patent is extended or adjusted under 35 U.S.C. 154(b) by 1109 days.

(21) Appl. No.: 12/676,135

(22) PCT Filed: Sep. 12, 2008

(86) PCT No.: PCT/EP2008/062204
§ 371 (c)(1),
(2), (4) Date: Jan. 17, 2013

(87) PCT Pub. No.: WO2009/065635
PCT Pub. Date: May 28, 2009

(65) Prior Publication Data
US 2011/0021369 A1    Jan. 27, 2011

(30) Foreign Application Priority Data
Sep. 12, 2007 (EP) .................... 07291093

(51) Int. Cl.
*C12Q 1/68* (2006.01)
(52) U.S. Cl.
CPC ................ *C12Q 1/6897* (2013.01)
(58) Field of Classification Search
None
See application file for complete search history.

(56) References Cited

U.S. PATENT DOCUMENTS

| 6,692,965 | B1 | 2/2004 | Shekdar et al. |
| 2005/0191622 | A1 | 9/2005 | Siegel |
| 2006/0094019 | A1* | 5/2006 | Selvin et al. ............ 435/6 |

FOREIGN PATENT DOCUMENTS

| WO | WO 9955886 A1 * | 11/1999 |
| WO | WO-00/23621 A2 | 4/2000 |
| WO | WO 0171042 A2 * | 9/2001 |

OTHER PUBLICATIONS

Bratu et al., PNAS, 2003, vol. 100, pp. 13308-13313.*
Cowley et al., Gene, 2001, vol. 264, pp. 225-231.*
Vargas et al., PNAS, vol. 102, pp. 17008-17013.*
Berger et al., Breast Cancer Research, vol. 3, pp. 28-35.*
Marras et al., European Journal of Internal Medicine, 2005, vol. 363, pp. 48-60.*
Vargas et al., "Mechanism of mRNA transport in the nucleus", Proceedings of the National Academy of the United States of America, vol. 102, No. 47, Nov. 2005, pp. 17008-17013.
Poeta Del M et al., "Cryptococcus neoforms differential gene expression detected in vitro and in vivo with green fluorescent protein", Infection and Immunity, American Society for Microbiology, Washington, US, vol. 67, No. 4, Apr. 1999, pp. 1812-1820.
Vieites J. M. et al., "Expression and in vivo determination of firefly luciferase as gene reporter in *Saccharmoyces cerevisiae*", Yeast, Chichester, Sussex, GB, vol. 10, No. 10, 1994, pp. 1321-1327.
Niedz R. P. et al., "Green flourescent protein: An in vivo reporter of plant gene expression", Plant cell reports, Springer Verlag, DE, vol. 14, No. 7, 1995, pp. 403-406.
Marras et al., "Real-time assays with molecular beacons and other fluorescent nucleic acid hybridization probes", Clinica Chimica Acta, Amsterdam, NL, vol. 363, No. 1-2, Jan. 2006, pp. 48-60.
Mhlanga Musa M. et al., "tRNA-linked molecular beacons for imaging mRNAs in the cytoplasm of living cells", Nucleic Acids Research, vol. 33, No. 6, 2005, pp. 1902-1912.
Gossen, Manfred et al., "Tight control of gene expression in mammalian cells by tetracycline-responsive promoters", Proc. Natl., Acad., Sci., USA, 2005, vol. 89, pp. 5547-5551.
Drake et al., "Stochasticity of Manganese Superoxide Dismutase mRNA Expression in Breast Carcinoma Cells by Molecular Beacon Imaging", ChemBioChem, vol. 6 (2005) pp. 2041-2047.
Forrest et al., "Live Imaging of Endogenous RNA Reveals a Diffusion and Entrapment Mechanism for nanos mRNA Localization in *Drosophila*", Current Biology, vol. 13 (2003) pp. 1159-1168.
Peng et al., "Real-time Detection of Gene Expression in Cancer Cells Using Molecular Beacon Imaging: New Strategies for Cancer Research", Cancer Res., vol. 65, No. 5 (2005) pp. 1909-1917.
Rodriguez et al., "Imaging mRNA movement from transcription sites to translation sites", Seminars in Cell & Developmental Biology, vol. 18 (2007) pp. 202-208.
Tsourkas et al., "Shedding light on health and disease using molecular beacons", Briefings in Functional Genomics and Proteomics, vol. 1, No. 4 (2003) pp. 372-384.

* cited by examiner

*Primary Examiner* — Mindy G Brown
(74) *Attorney, Agent, or Firm* — Birch, Stewart, Kolasch & Birch, LLP

(57) ABSTRACT

The invention relates to a double-stranded polynucleotide comprising on its positive strand considered from its 5' end to its 3' end, (i) a promoter of a gene of interest or several promoters of various genes of interest selected among genes which are endogenous to a determined cell, and, (ii) one or several barcode(s) wherein each barcode contains at least one barcode unit formed of at least one, especially of multiple, recognition binding sites each binding site being composed of a nucleotide sequence, and wherein each of said barcode(s) is under the control of at least one of said promoter(s) for transcription. It further concerns use of said polynucleotide to monitor gene expression patterns in living cells, especially in single cells, with a rapid and high spatio-temporal resolution.

22 Claims, 22 Drawing Sheets

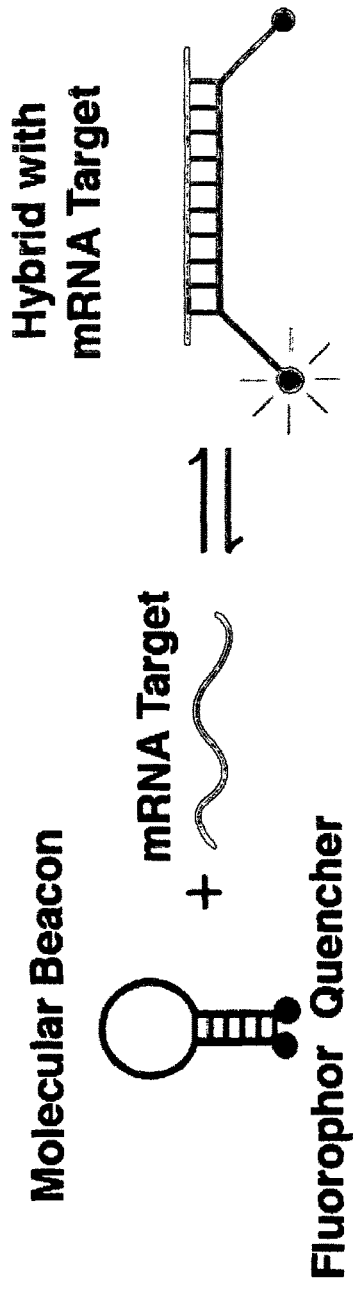

Dual Color Coding Scheme

| Gene | Color 1 | Color 2 | Color 3 | Color 4 | Color 5 | Color 6 |
|------|---------|---------|---------|---------|---------|---------|
| Gene A | ● | ● | | | | |
| Gene B | ● | | ○ | | | |
| Gene C | ● | | | ● | | |
| Gene D | ● | | | | ● | |
| Gene E | ● | | | | | ● |
| Gene F | | ● | ○ | | | |
| Gene G | | ● | | ● | | |
| Gene H | | ● | | | ● | |
| Gene I | | ● | | | | ● |
| Gene J | | | ○ | ● | | |
| Gene K | | | ● | | ● | |
| Gene L | | | ● | | | ● |
| Gene M | | | | ● | ● | |
| Gene N | | | | ● | | ● |
| Gene O | | | | | ● | ● |

FIGURE 5A(1)

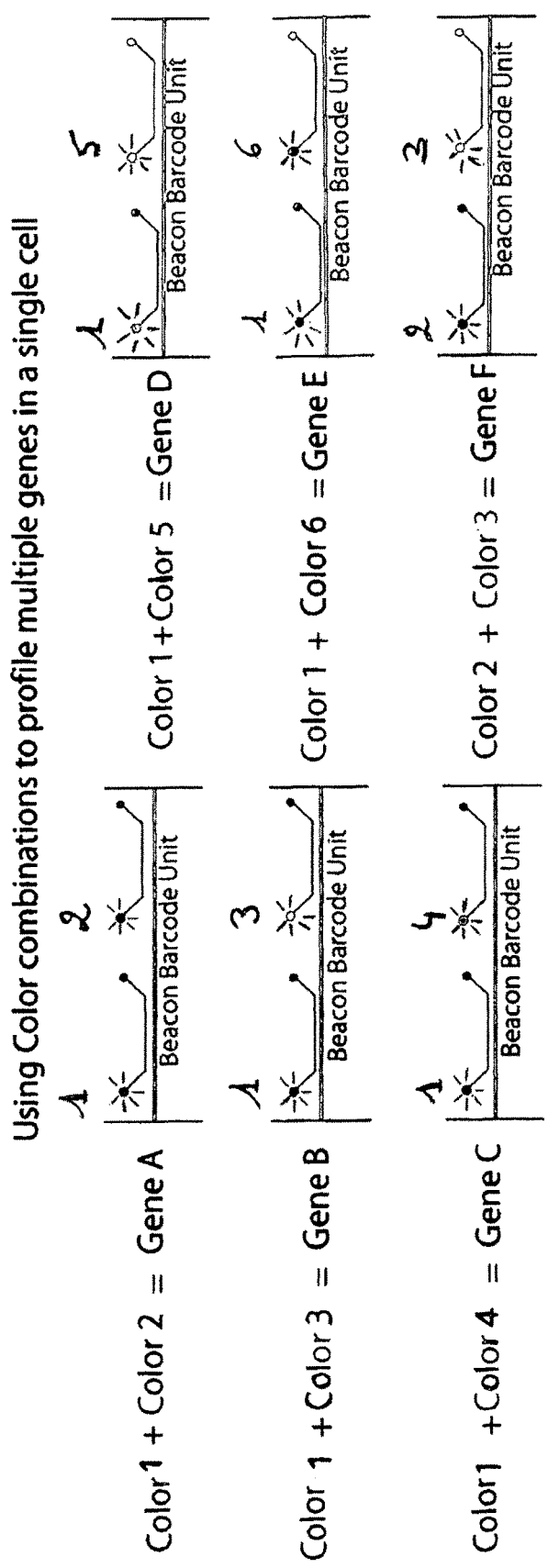
FIGURE 5A(2)

Triplex Color Coding Scheme

| Gene | Color 1 | Color 2 | Color 3 | Color 4 | Color 5 | Color 6 |
|------|---------|---------|---------|---------|---------|---------|
| Gene A | ● | ● | ○ | | | |
| Gene B | ● | ● | | ◉ | | |
| Gene C | ● | ● | | | ◉ | |
| Gene D | ● | ● | | | | ● |
| Gene E | ● | | ○ | ◉ | | |
| Gene F | ● | | ○ | | ● | |
| Gene G | ● | | ○ | | | ● |
| Gene H | ● | | | ● | ● | |
| Gene I | ● | | | ● | | ● |
| Gene J | ● | | | | ● | ● |
| Gene K | | ● | ○ | ◉ | | |
| Gene L | | ● | ○ | | ● | |
| Gene M | | ● | ○ | | | ● |
| Gene N | | ● | | ◉ | ● | |
| Gene O | | ● | | ◉ | | ● |
| Gene P | | ● | | | ● | ● |
| Gene Q | | | ○ | ◉ | ● | |
| Gene R | | | ○ | ● | | ● |
| Gene S | | | ○ | | ● | ● |
| Gene T | | | | ◉ | ● | ● |

FIGURE 5B

Kana :
GGCCGGCCAGATCTACTAGTCTCGAGGCTAGCCTGCAGGAGACTCTAGAT
CATAATCAGCCATACCACATTTGTAGAGGTTTTACTTGCTTTAAAAAACCT
CCCACACCTCCCCCTGAACCTGAAACATAAAATGAATGCAATTGTTGTTGT
TAACTTGTTTATTGCAGCTTATAATGGTTACAAATAAAGCAATAGCATCAC
AAATTTCACAAATAAAGCATTTTTTCACTGCATTCTAGTTGTGGTTTGTC
CAAACTCATCAATGTATCTCAGGTGGCACTTTTCGGGGAAATGTGCGCGG
AACCCCTATTTGTTTATTTTTCTAAATACATTCAAATATGTATCCGCTCATG
AGACAATAACCCTGATAAATGCTTCAATAATATTGAAAAAGGAAGAGTCC
TGAGGCGGAAAGAACCAGCTGTGGAATGTGTGTCAGTTAGGGTGTGGAA
AGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCC
CATGCTGACTAATTTTTTTTATTTATGCAGAGGCCGAGGCCGCCTCGGCCT
CTGAGCTATTCCAGAAGTAGTGAGGAGGCTTTTTGGAGGCCTAGGCTTTT
GCAAAGATCGATCAAGAGACAGGATGAGGATCGTTTCGCATGATTGAACA
AGATGGATTGCACGCAGGTTCTCCGGCCGCTTGGGTGGAGAGGCTATTCG
GCTATGACTGGGCACAACAGACAATCGGCTGCTCTGATGCCGCCGTGTTC
CGGCTGTCAGCGCAGGGGCGCCCGGTTCTTTTTGTCAAGACCGACCTGTCC
GGTGCCCTGAATGAACTGCAAGACGAGGCAGCGCGGCTATCGTGGCTGGC
CACGACGGGCGTTCCTTGCGCAGCTGTGCTCGACGTTGTCACTGAAGCGG
GAAGGGACTGGCTGCTATTGGGCGAAGTGCCGGGGCAGGATCTCCTGTCA
TCTCACCTTGCTCCTGCCGAGAAAGTATCCATCATGGCTGATGCAATGCGG
CGGCTGCATACGCTTGATCCGGCTACCTGCCCATTCGACCACCAAGCGAA
ACATCGCATCGAGCGAGCACGTACTCGGATGGAAGCCGGTCTTGTCGATC
AGGATGATCTGGACGAAGAGCATCAGGGGCTCGCGCCAGCCGAACTGTTC
GCCAGGCTCAAGGCGAGCATGCCCGACGGCGAGGATCTCGTCGTGACCCA
CGGCGATGCCTGCTTGCCGAATATCATGGTGGAAAATGGCCGCTTTTCTG
GATTCATCGACTGTGGCCGGCTGGGTGTGGCGGACCGCTATCAGGACATA
GCGTTGGCTACCCGTGATATTGCTGAAGAGCTTGGCGGCGAATGGGCTGA
CCGCTTCCTCGTGCTTTACGGTATCGCCGCTCCCGATTCGCAGCGCATCGC
CTTCTATCGCCTTCTTGACGAGTTCTTCTGAAATAAAAATAAAAAGCTT

Zeo
GGCCGGCCAGATCTACTAGTCTCGAGGCTAGCCTGCAGGAGACTCTAGAT
CATAATCAGCCATACCACATTTGTAGAGGTTTTACTTGCTTTAAAAAACCT
CCCACACCTCCCCCTGAACCTGAAACATAAAATGAATGCAATTGTTGTTGT
TAACTTGTTTATTGCAGCTTATAATGGTTACAAATAAAGCAATAGCATCAC
AAATTTCACAAATAAAGCATTTTTTCACTGCATTCTAGTTGTGGTTTGTC
CAAACTCATCAATGTATCTCAGGTGGCACTTTTCGGGGAAATGTGCGCGG
AACCCCTATTTGTTTATTTTTCTAAATACATTCAAATATGTATCCGCTCATG
AGACAATAACCCTGATAAATGCTTCAATAATATTGAAAAAGGAAGAGTCC
TGAGGCGGAAAGAACCAGCTGTGGAATGTGTGTCAGTTAGGGTGTGGAA
AGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCC
CATGCTGACTAATTTTTTTTATTTATGCAGAGGCCGAGGCCGCCTCGGCCT

FIG. 6A

CTGAGCTATTCCAGAAGTAGTGAGGAGGCTTTTTTGGAGGCCTAGGCTTTT
GCAAAGATCGATCAAGAGACAGGATGAGGATCGTTTCGCATGGCCAAGTT
GACCAGTGCCGTTCCGGTGCTCACCGCGCGACGTCGCCGGAGCGGTCG
AGTTCTGGACCGACCGGCTCGGGTTCTCCCGGGACTTCGTGGAGGACGAC
TTCGCCGGTGTGGTCCGGGACGACGTGACCCTGTTCATCAGCGCGGTCCA
GGACCAGGTGGTGCCGGACAACACCCTGGCCTGGGTGTGGGTGCGCGGCC
TGGACGAGCTGTACGCCGAGTGGTCGGAGGTCGTGTCCACGAACTTCCGG
GACGCCTCCGGGACGGCCATGACCGAGATCGGCGAGCAGCCGTGGGGGC
GGGAGTTCGCCCTGCGCGACCCGGCCGGCAACTGCGTGCACTTCGTGGCC
GAGGAGCAGGACTGAAATAAAAATAAAAAGCTT

Hygro:
GGCCGGCCAGATCTACTAGTCTCGAGGCTAGCCTGCAGGAGACTCTAGAT
CATAATCAGCCATACCACATTTGTAGAGGTTTTACTTGCTTTAAAAAACCT
CCCACACCTCCCCCTGAACCTGAAACATAAAATGAATGCAATTGTTGTTGT
TAACTTGTTTATTGCAGCTTATAATGGTTACAAATAAAGCAATAGCATCAC
AAATTTCACAAATAAAGCATTTTTTCACTGCATTCTAGTTGTGGTTTGTC
CAAACTCATCAATGTATCTCAGGTGGCACTTTTCGGGGAAATGTGCGCGG
AACCCCTATTTGTTTATTTTTCTAAATACATTCAAATATGTATCCGCTCATG
AGACAATAACCCTGATAAATGCTTCAATAATATTGAAAAAGGAAGAGTCC
TGAGGCGGAAAGAACCAGCTGTGGAATGTGTGTCAGTTAGGGTGTGGAA
AGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAA
GTATGCAAAGCATGCATCTCAATTAGTCAGCAACCATAGTCCCGCCCCTA
ACTCCGCCCATCCCGCCCCTAACTCCGCCCAGTTCCGCCCATTCTCCGCCC
CATGCTGACTAATTTTTTTATTTATGCAGAGGCCGAGGCCGCCTCGGCCT
CTGAGCTATTCCAGAAGTAGTGAGGAGGCTTTTTTGGAGGCCTAGGCTTTT
GCAAAGATCGATCAAGAGACAGGATGAGGATCGTTTCGCATGGGTAAAA
AGCCTGAACTCACCGCGACGTCTGTCGAGAAGTTTCTGATCGAAAAGTTC
GACAGCGTCTCCGACCTGATGCAGCTCTCGGAGGGCGAAGAATCTCGTGC
TTTCAGCTTCGATGTAGGAGGGCGTGGATATGTCCTGCGGGTAAATAGCT
GCGCCGATGGTTTCTACAAAGATCGTTATGTTTATCGGCACTTTGCATCGG
CCGCGCTCCCGATTCCGGAAGTGCTTGACATTGGGGAATTCAGCGAGAGC
CTGACCTATTGCATCTCCCGCCGTGCACAGGGTGTCACGTTGCAAGACCTG
CCTGAAACCGAACTGCCCGCTGTTCTGCAGCCGGTCGCGGAGGCTATGGA
TGCGATCGCTGCGGCCGATCTTAGCCAGACGAGCGGGTTCGGCCCATTCG
GACCGCAAGGAATCGGTCAATACACTACATGGCGTGATTTCATATGCGCG
ATTGCTGATCCCCATGTGTATCACTGGCAAACTGTGATGGACGACACCGT
CAGTGCGTCCGTCGCGCAGGCTCTCGATGAGCTGATGCTTTGGGCCGAGG
ACTGCCCCGAAGTCCGGCACCTCGTGCACGCGGATTTCGGCTCCAACAAT
GTCCTGACGGACAATGGCCGCATAACAGCGGTCATTGACTGGAGCGAGGC
GATGTTCGGGGATTCCCAATACGAGGTCGCCAACATCTTCTTCTGGAGGC
CGTGGTTGGCTTGTATGGAGCAGCAGACGCGCTACTTCGAGCGGAGGCAT
CCGGAGCTTGCAGGATCGCCGCGGCTCCGGGCGTATATGCTCCGCATTGG
TCTTGACCAACTCTATCAGAGCTTGGTTGACGGCAATTTCGATGATGCAGC
TTGGGCGCAGGGTCGATGCGACGCAATCGTCCGATCCGGAGCCGGGACTG
TCGGGCGTACACAAATCGCCCGCAGAAGCGCGGCCGTCTGGACCGATGGC
TGTGTAGAAGTACTCGCCGATAGTGGAAACCGACGCCCCAGCACTCGTCC
GAGGGCAAAGGAATAAAATAAAAATAAAAAGCTT

GAATTCCCTAGGTCAGTGTTCCTCCCAGTTACAGTCTAAACTGGAATGGCA
GGCAAAGCCCCTGTGGAAGGGGAAGGTGAAGGCTCAATCAAAGGATCCC
CAGAGACTTTCCAGATATCTGAAGAAGTCCTGATGTCACTGCCCCGGTCCT
TCCCAGGTAGAGCAACACTCCTCGTCGCAACCCAACTGGCTCCCCTTACC
TTCTACACACACACACACACACACACACACACACACACACACACACACAA
ATCCAAGACAACACTACTAAGGCTTCTTTGGGAAGGGGAAGTAGGGATAG
GTAAGAGGAAAGTAAGGGACCTCCTATCCAGCCTCCATGGAATCCTGACT
TCTTTTCCTTGTTATTTCAACTTCTTCCACCCCATCTTTTAAACTTTAGACT
CCAGCCACAGAAGCTTACAACTAAAAGAAACTCAAGGCCAATTTAATCC
AAGGTTTCATTCTATGTGCTGGAGATGGTGTACAGTAGGGTGAGGAAACC
AAATTCTCAGTTGGCACTGGTGTACCCTTGTACAGGTGATGTAATATCTCT
GTGCCTCAGTTTGCTCACTATAAAATAGAGACGGTAGGGTCATGGTGAG
CACTACCTGACTAGCATATAAGAAGCTTTCAGCAAGTGCAGACTACTCTT
ACCCACTTCCCCCAAGCACAGTTGGGGTGGGGACAGCTGAAGAGGTGG
AAACATGTGCCGGAGAATCCTAATGAAATCGGGTAAAGGAGCCTGGAA
CACATCCTGTGACCCCGCCTGTACTGTAGGAAGCCAGTCTCTGGAAAGTA
AAATGGAAGGGCTGCTTGGGAACTTTGAGGATATTTAGCCCACCCCCTCA
TTTTTACTTGGGGAAACTAAGGCCCAGAGACCTAAGGTGACTGCCTAAGT
TAGCAAGGAGAAGTCTTGGGTATTCATCCCAGGTTGGGGGGACCCAATTA
TTTCTCAATCCCATTGTATTCTGGAATGGGCAATTTGTCCACGTCACTGTG
ACCTAGGAACACGCGAATGAGAACCCACAGCTGAGGGCCTCTGCGCACA
GAACAGCTGTTCTCCCCAGGAAATCAACTTTTTTTAATTGAGAAGCTAAA
AAATTATTCTAAGAGAGGTAGCCCATCCTAAAAATAGCTGTAATGCAGAA
GTTCATGTTCAACCAATCATTTTTGCTTACGATGCAAAAATTGAAAACTAA
GTTTATTAGAGAGGTTAGAGAAGGAGGAGCTCTAAGCAGAAAAAATCCT
GTGCCGGGAAACCTTGATTGTGGCTTTTAATGAATGAAGAGGCCTCCCT
GAGCTTACAATATAAAGGGGGAGAGAGAGGTGAAGGGTCGAC

CCL20:
GAATTCGTTATTTGACATTTGCTGTGCTGACTAGCTACTGCTGATAGGTTT
TCTTTCCCTCAACAATTCTGAGGCTCTATATTGAGTTATATTAGTACATCA
TCATGGAGAGTTAAAGGTAGGTAAGGATTATTTTCTGAACTGCAATATTG
ATTAAAGCCATGTGAATGTATAAGATTCTTAGAAGAGTTGACATTAAATC
AAGGTGAAGCTGAGGTTTGAGCCTTACTTAAAGGCTGATATTTTCCACTCT
AACTGCGGACAGTACTGTAGCACTGTTATAGTACCTGCTCTGAATGTTAGT
CTAGCAACTCAGGGTCTTCTTCATGACAGCTGAACCTCAACCATGTGATG
GTAAATGTGTAGCAGAGTATGCCTGGCATCCCACCTGCTCCTCCTCCCCT
CCTCCTTGACTGGTTCTGGAAAGCAAATAGGGTGTAACAATAGGAGTTCT
GGAATGTTCCTGTGTGGGGCTGACCTTTGTATCGCTGTTAATCCTCTATTTT
CAGACACAAAAATGATTAAGTTAAAACTGGATGAAAGTCTTTTCTGGGTC
ACAGGGCTGAGCTGCTTTTGCTCTTTGCAAATACAAAGAATTTAACAGGA
TTCTCCCCTTCTCAACTTCCTGTCCCCACCCTGACCTTCGCACCTTCCCAA
TATGAGGAAAAAGCAGGAAGTTTTCCTTGCGGGTTTTTTTATGATGACAT
GATGGGGCCAGTTGATCAATGGGGAAAACCCCATGTGGCAACACGCCTTC
TGTGTACATTCCCAATATTTGCTATAAATAGGGCCATCCCAGGCTGCTGTC
AGAATATAACAGCACTCCCAAAGAACTGGGTACTCAACACTGAGCAGATC
TGTTCTTTGAGCTAAAAACCATGGGATCC

FIG. 6C

ICAM-1

```
GTCGACGGTACCTGTAGTCTCAGCTACCTGGGAGGCTGAGGCAAGAGAAT
CGCTTGAACCTGGGAAGTAGAGGTTGCAGTGAGCCGAGATTGCACCACTG
CACTCCAGCCTGGGCGACGGAGTGAGACGACCTCACAAAAATTTACATAA
ATAAAATGAAAAGTAAAATAAAAATACAAAAGTTGGCCGGGTGCGTTTG
CTCACGCCTGTAATCCCAGCACTTTGGGAGGGTGAGGCAGGCAGATAATG
AGGTAAGAAGATCGAGACCATCCTGGCTAACACGGTGAAACCCTGTCTCT
ACTAAAAATACAAAAAATTAGCTGTGCGTGGTGACACGCACCTGTAGTCC
CAGCTATTTGGGAGGCTGAGGCAGGAGAATCACTTGAACCTGGGAGGTGG
AGGTTGCAGTGAGCCGAGATCGCACCACTGCACTCCAGCCTGGGCCACAG
AGTGAGACTCCATCTTGAAAAAAAAAAAAAATACAAAAGTTAGCCAGGG
GTGTTGGTGGGTGCCTGTAATCCCAGCTATTTGGGAGGCTAAGGCAGAAG
AATTTCTTGAACCTAGGAAACGGAGGTTGCAGTGAGCCGAGATCACACCT
CTGTACTCCAGCCTGGACAACAGAGCGAGACTTTGTCTCAAAAAAAAAAA
AAAAAAAAAACTAAATAGGCCGGGAGCAGTGGCTCATGCCTATAATCCC
AGCCTTTGGGAGGCCAAGGCAGGTGGATCACTTGAGGTCAGGAGTTTGAG
ACCAGGCTGGCCAACATGGTGTAACCCCGTCTCTACTAAAAACACAAAAA
TTAGCCGGGTCTGGTGGCGTATGTCTGTAATCCCAGCTACTCGGGAGGCT
GAGGCAGGAGAATCACTTAAACCTGGGAGGCAGGGGTTGCAGTGAGCTG
AGATCGTGCCACTGCACTCTAGCCAGGGTGACAGAGTGAAACTCTGTCTC
AAAAAATTAAAAAAGAAATTCAGCAAGTAATGAGTTAAGGAATTCGAAT
ATTAAGGCGAGTGACAAGGAACGCCCAGGATGTGGCCCAGGATGGAGTA
GGGGGGACACTCATTTAGGAGAAAGCTCAGGCCACAAGACAGGAGGAGC
CAGCCTTGTTGGGGTTGAAGGGAAGAGCATTCCAGGCTGAGGGAACTGCA
AGGCGTTTGCATGGGACACTATGGGATGGCTTCTGCCCTTGGTGGGCAGC
CTCTGGTCTGAGGCCATTCTTTGGCCTGCCTGACTGTCTGGCAACCGGGAG
GAAGCCCTGCCCTTCCTGGAGACAGAAACAAAGGTCTAGGAAATATCTGC
TTCCCTTTTCCTTGAAAAACGCTTAAGGGAACGGAGGACTGGGAGGTGCC
GTCTCTCTGCCAGCCTGCCCCCTACCATAGCCATCCCACTCCCATCTCA
GAAAGTGACCCGCCATCCTCCAAAAGGCTCGGACCCTGATCAAGGAGTCA
TCCCCCTTGTCCCAGCACCTCCAGTTGGCCCAGCCTCCAAAACGGATGTCA
AATTCAGCCCTTTCTCCAAGGACACTGCCCAGTCCAGGCCCCACTATCATT
CATCTGGACTAGAACAGTCACCTCCTCTCCCATCTCCTGGCTGCAGCTCTT
GAAGCCTCAACTGGGCCCCTGTGAACACTTGAGTTAGGGCAAGGTCCTTC
CTCTGCTCAGAACCCTCTATACCTCCCACCTCGCTGGGCATAAAAGCCAA
AGTCCTGGCCAGGCACGGTGGCTCACATCTGTTATCCCAGCACTTTGGGA
GGCCAAGGGGGCGGATCACTAGAGGTCAGGAGTTAGAGACCAACATGG
TGAAACCCCATCTCTACTAAAAATACAAAAATTAGCTAGGCGTGGTGACG
CACCCCTGTAGTACCAGCTACTCGGTAGGCTGAGGTGGGAGAATCGCTTG
AACCTGGGAGGCAGAGTTTGCAGTGAGCCGAGATCACACCACTGTGCTCC
AGCCTGGGTGACAGAACGAGACTGGGGTTCAGAAACAAACAAACAAAAC
AACAAAGTCCTCCTCAGGTGACAGGAACTTGCACCTATCTGCCCTGTCATC
TCCCTGCCCGCTCCTCTCCTCGAATCTCTCCTTTGCTAAGCCTGCTCCAGCC
ACACTGTTCTCCTGGCTGTTCCTTTTTTTTTTTTTGAGTCTCACTCTCACC
CAGGCTGGAGTGCAGTGCCTCTATCTTGGCTCACTGCAACCTCCGCTGCCG
GGTTCAAGAGATTCTCCTGCATCAGCCTCCCAAGTAGGTGGAATTACAGG
TGTGCACCACCACACCCGGCTAATTTTTGTATTTTGCATAGAGATGGGGT
CTCCCTATGTTGCCCAGGCTGGTCTTGAACTCCTGGGCTCAAGTGATCCTC
CCATCTCGGCCTCCCAAAATGCTGGGATTACAGGTGGGAGCCGCGCCCAG
```

FIG. 6D

GTGGATTTTGTCTGACTCTGTTCATTCCTGTGTCCCCAGTACCTGAAGGAC
GCCAAGCACACAGTAGGCGCTTAAAAAACATTGAGCCACATGTTGAGAA
AAGAACGGCACCATTGTGGCTGCAAGTGGGACTTGGGCCGCGCGGGGGA
CGTCGCGCACCTCGGGCCGGGGCAAGAGCTCAGTGGAACCCGCCCGAGG
AAGAACCCGTGGCGCAGGATTTTCCCAGGCCTTCTGAGGACCAGGGGCGT
CCCCCGTCCCACCCTGTGACTTTGCTCAGGCGTTCCGGGGCGGGAATTCAG
AACTGGATCC

TGF-beta
GAATTCGGCAGGAATTTTTGTCTGCCATCCATGTTCATGTCTGCCGTGTCC
CCAGCTAGCTAGAACAGAGTCTAGCACAGGAGAAGGGATCAGCATGAGA
TGAGATGGGGCTGGATCTCCAAGGGCTTTGACTACCAGACTGAGGAGCTG
AACTGTGTTCTGAGGACATGGGCAAAGCTATGGAAGGAGAGAAAGATGC
TTCCAGATGCCAGGTGGAAGGTGGATTAGAGAGGGGCAAGAAAGAAGGC
CCTGGGCCCAAAGGGAGCAGGGCAGGGACATGAGGAGGGAAGGCAGGA
GGTGTCCCTGACAAGGCCCATGATGGTTACCTGGGGACTGGAGGAGCAAT
GGGCTGCCCTGACATGGGTCATGGAGGAGGATAACACAGAGAGGAAAT
TCAGCAGAGGTCTGATTAGAAGGGCCTTGAATGTTGAAGAGGTTGGACTT
TATACTGAGGGCACTGGGGAGCTATGGAAGGATCCTTAGCAGGGAGTA
ACATGGATTTGGAAAGATCACTTTGGCTGCTGTGTGGGGATAGATAAGAC
GGTGGGAGCCTAGAAAGGAGGCTGGGTTGGAAACTCTGGGACAGAAACC
CAGAGAGGAAAAGACTGGGCCTGGGGTCTCCAGTGAGTATCAGGGAGTG
GGGAATCAGCAGGAGTCTGGTCCCCACCCATCCCTCCTTTCCCTCTCTCT
CCTTTCCTGCAGGCTGGCCCCGGCTCCATTTCCAGGTGTGGTCCCAGGACA
GCTTTGGCCGCTGCCAGCTTGCAGGCTATGGATTTTGCCATGTGCCCAGTA
GCCCGGGCACCCACCAGCTGGCCTGCCCCACGTGGCGGCCCCTGGGCAGT
TGGCGAGAACAGTTGGCACGGGCTTTCGTGGGTGGTGGGCCGCAGCTGCT
GCATGGGGACACCATCTACAGTGGGGCCGACCGCTATCGCCTGCACACAG
CTGCTGGTGGCACCGTGCACCTGGAGATCGGCCTGCTGCTCCGCAACTTC
GACCGCTACGGCGTGGAGTGCTGAGGGACTCTGCCTCCAACGTCACCACC
ATCCACACCCCGGACACCCAGTGATGGGGAGGATGGCACAGTGGTCAA
GAGCACAGACTCTAGAGACTGTCAGAGCTGACCCCAGCTAAGGCATGGCA
CCGCTTCTGTCCTTTCTAGGACCTCGGGGTCCCTCTGGGCCCAGTTTCCCT
ATCTGTAAATTGGGGACAGTAAATGTATGGGTCGCAGGGTGTTGAGTGA
CAGGAGGCTGCTTAGCCACATGGGAGGTGCTCAGTAAAGGAGAGCAATTC
TTACAGGTGTCTGCCTCCTGACCCTTCCATCCCTCAGGTGTCCTGTTGCCC
CCTCCTCCCACTGACACCCTCCGGAGGCCCCCATGTTGACAGACCCTCTTC
TCCTACCTTGTTTCCCAGCCTGACTCTCCTTCCGTTCTGGGTCCCCCTCCTC
TGGTCGGCTCCCCTGTGTCTCATCCCCCGGATTAAGCCTTCTCCGCCTGGT
CCTCTTTCTCTGGTGACCCACACCGCCCGCAAAGCCACAGCGCATCTGGAT
CACCCGCTTTGGTGGCGCTTGGCCGCCAGGAGGCAGCACCCTGTTTGCGG
GGCGGAGCCGGGGTGCCCGCCCCTTTCCCCCAGGGCTGAAGGGACCCCC
CTCGGAGCCCGCCCACGCGAGATGAGGACGGTGGCCCAGCCCCCCATGC
CCTCCCCCTGGGGGCCGCCCCGCTCCCGCCCCGTGCGCTTCCTGGGTGGG
GCCGGGGGCGGCTTCAAAACCCCCTGCCGACCCAGCCGGTCCCCGCCGCC
GCCGCCCTTCGCGCCCTGGGCCATCTCCCTCCCGTCGAC

FIG. 6E c-fos :
GAATTCGCAGCCGGGCGGCCGCAGAAGCGCCCAGGCCCGCGCGCCACCC
CTCTGGCGCCACCGTGGTTGAGCCCGTGACGTTTACACTCATTCATAAAAC
GCTTGTTATAAAAGCAGTGGCTGCGGCGCCTCGTACTCCAACCGCATCTG
CAGCGAGCAACTGAGAAGCCAAGACTGAGCCGGCGGCCGCGGCGCAGCG
AACGAGCAGTGACCGTGCTCCTACCCAGCTCTGCTTCACAGCGCCCACCT
GTCTCCGCCCTCGGCCCCTCGCCCGGCTTTGCCTAACCGCCACGATGATG
TTCTCGGGCTTCAACGCAGACTACGAGGCGTCATCCTCCGCTGCAGCAG
CGCGTCCCCGGCCGGGGATAGCCTCTCTTACTACCACTCACCCGCAGACTC
CTTCTCCAGCATGGGCTCGCCTGTCAACGCGCAGGTAAGGCTGGCTTCCC
GTCGCCGCGGGGCCGGGGGCTTGGGGTCGCGGAGGAGGAGACACCGGGC
GGGACGCTCCAGTAGATGAGTAGGGGGCTCCCTTGTGCCTGGAGGGAGGC
TGCCGTGGCCGGAGCGGTGCCGGCTCGGGGCTCGGGACTTGCTCTGAGC
GCACGCACGCTTGCCATAGTAAGAATTGGTTCCCCCTTCGGGAGGCAGGT
TCGTTCTGAGCAACCTCTGGTCTGCACTCCAGGACGGATCTCTGACATTAG
CTGGAGCAGACGTGTCCCAAGCACAAACTCGCTAACTAGAGCCTGGCTTC
TTCGGGGAGGTGGCGGATCC

AB-repeat:
GTCGACTTCTCTTCAAACTTTTCCGCTTTTAGAGAGAGCGCCAAAACCTAT
TATCTTAAGTCGCTGCCGATTCTCTTCAAACTTTTCCGCTTTTGGTCGATGC
GCCAAAACCTATTATCTTAAGTCCTGGATTGTTCTCTTCAAACTTTTCCGCT
TTTGCCTGGAACGCCAAAACCTATTATCTTAAGTCGGCGTTAATTCTCTTC
AAACTTTTCCGCTTTTTTAAAGGCGCCAAAACCTATTATCTTAAGTCATT
TGCGGTTCTCTTCAAACTTTTCCGCTTTTGATGGCCACGCCAAAACCTATT
ATCTTAAGTCTGAACGCTCTCGAG

AC-repeat:
GTCGACTTCTCTTCAAACTTTTCCGCTTTTAGAGAGAGGAGTTGTGTTT
GTGGACGTGCCAGCATTCTCTTCAAACTTTTCCGCTTTTGGTCGATGAGGA
GTTGTGTTTGTGGACTAGCGTACTTCTCTTCAAACTTTTCCGCTTTTGCCTG
GAAAGGAGTTGTGTTTGTGGACAAATCGCATTCTCTTCAAACTTTTCCGCT
TTTTTAAAGGAGGAGTTGTGTTTGTGGACCATTGAAGTTCTCTTCAAACT
TTTCCGCTTTTCTGACGGCAGGAGTTGTGTTTGTGGACGGGGTCAGCTCGA
G

CB-repeat:
GTCGACAGGAGTTGTGTTTGTGGACGTGCCAGCCGCCAAAACCTATTATC
TTAAGTCGTGGTCATAGGAGTTGTGTTTGTGGACTAGCGTACCGCCAAAA
CCTATTATCTTAAGTCTAAAGATGAGGAGTTGTGTTTGTGGACAAATCGCA
CGCCAAAACCTATTATCTTAAGTCGTGGATGTAGGAGTTGTGTTTGTGGAC
ATTCACCTCGCCAAAACCTATTATCTTAAGTCCCGCGCTTAGGAGTTGTGT
TTGTGGACCATTGAAGCGCCAAAACCTATTATCTTAAGTCTGAACGCTCTC
GAG

FIG. 6F

SEQUENCE LISTING

```
<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ttctcttcaa actttccgc tttt                                              24

<210> SEQ ID NO 2
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 2
cgccaaaacc tattatctta agtc                                              24

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
ctcacctgct cttctcagac c                                                 21

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
gctatagcac taaggtaaga ccc                                               23

<210> SEQ ID NO 5
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 5
gcugcaaaag cggaaaaguu ugaagagaag cagc                                   34

<210> SEQ ID NO 6
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 6
cgaccgacuu aagauaauag guuuuggcgg gucg                                   34

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
ttctcttcaa actttccgc tttt                                               24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
```
cgccaaaacc tattatctta agtc                                            24

<210> SEQ ID NO 9
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 9
acgcgtcgac ttctcttcaa acttttccgc ttttagagag agcgccaaaa cctattatct    60
taagtcctcg agggatccgc g                                               81

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 10
cactgaatta atgaaagtgt gatgactcag gtttgccc                              38

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 11
tcagtggcta gcgaagcttg tgtgctctgc tgtct                                 35

<210> SEQ ID NO 12
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 12
gcugcaaaag cggaaaaguu ugaagagaag cagc                                  34

<210> SEQ ID NO 13
<211> LENGTH: 34
<212> TYPE: RNA
<213> ORGANISM: Artificial Sequence
<220> FEATURE:
<223> OTHER INFORMATION: Synthetic oligonucleotide

<400> SEQUENCE: 13
cgaccgacuu aagauaauag guuuuggcgg gucg                                  34

<210> SEQ ID NO 14
<211> LENGTH: 1609
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(1609)
<223> OTHER INFORMATION: Kana

<400> SEQUENCE: 14
ggccggccag atctactagt ctcgaggcta gcctgcagga gactctagat cataatcagc    60

```
cataccacat tgtagaggt tttacttgct ttaaaaaacc tcccacacct cccctgaac      120 ctgaaacata aaatgaatgc aattgttgtt gttaacttgt ttattgcagc ttataatggt    180
tacaaataaa gcaatagcat cacaaatttc acaaataaag catttttttc actgcattct    240
agttgtggtt tgtccaaact catcaatgta tctcaggtgg cacttttcgg ggaaatgtgc    300
gcggaacccc tatttgttta ttttctaaa tacattcaaa tatgtatccg ctcatgagac     360
aataaccctg ataaatgctt caataatatt gaaaaggaa gagtcctgag gcggaaagaa     420
ccagctgtgg aatgtgtgtc agttaggtgt ggaaagtcc ccaggctccc cagcaggcag     480
aagtatgcaa agcatgcatc tcaattagtc agcaaccagg tgtggaaagt ccccaggctc    540
cccagcaggc agaagtatgc aaagcatgca tctcaattag tcagcaacca tagtcccgcc    600
cctaactccg cccatcccgc ccctaactcc gcccagttcc gcccattctc cgccccatgc    660
tgactaattt tttttatta tgcagaggcc gaggccgcct cggcctctga gctattccag     720
aagtagtgag gaggcttttt tggaggccta ggcttttgca aagatcgatc aagagacagg    780
atgaggatcg tttcgcatga ttgaacaaga tggattgcac gcaggttctc cggccgcttg    840
ggtggagagg ctattcggct atgactgggc acaacagaca atcggctgct ctgatgccgc    900
cgtgttccgg ctgtcagcgc aggggcgccc ggttcttttt gtcaagaccg acctgtccgg   960
tgccctgaat gaactgcaag acgaggcagc gcggctatcg tggctggcca cgacgggcgt   1020
tccttgcgca gctgtgctcg acgttgtcac tgaagcggga agggactggc tgctattggg   1080
cgaagtgccg gggcaggatc tcctgtcatc tcaccttgct cctgccgaga aagtatccat   1140
catggctgat gcaatgcggc ggctgcatac gcttgatccg gctacctgcc cattcgacca   1200
ccaagcgaaa catcgcatcg agcgagcacg tactcggatg gaagccggtc ttgtcgatca   1260
ggatgatctg gacgaagagc atcagggct cgcgccagcc gaactgttcg ccaggctcaa    1320
ggcgagcatg cccgacggcg aggatctcgt cgtgacccac ggcgatgcct gcttgccgaa   1380
tatcatggtg gaaaatggcc gcttttctgg attcatcgac tgtggccggc tgggtgtggc   1440
ggaccgctat caggacatag cgttggctac ccgtgatatt gctgaagagc ttggcggcga   1500
atgggctgac cgcttcctcg tgctttacgg tatcgccgct cccgattcgc agcgcatcgc   1560
cttctatcgc cttcttgacg agttcttctg aaataaaaat aaaaagctt              1609
```

<210> SEQ ID NO 15
<211> LENGTH: 1189
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(1189)
<223> OTHER INFORMATION: Zeo

<400> SEQUENCE: 15

```
ggccggccag atctactagt ctcgaggcta gcctgcagga gactctagat cataatcagc     60
cataccacat tgtagaggt tttacttgct ttaaaaaacc tcccacacct cccctgaac      120 ctgaaacata aaatgaatgc aattgttgtt gttaacttgt ttattgcagc ttataatggt    180
tacaaataaa gcaatagcat cacaaatttc acaaataaag catttttttc actgcattct    240
agttgtggtt tgtccaaact catcaatgta tctcaggtgg cacttttcgg ggaaatgtgc    300
gcggaacccc tatttgttta ttttctaaa tacattcaaa tatgtatccg ctcatgagac     360
```

| | |
|---|---|
| aataaccctg ataaatgctt caataatatt gaaaaaggaa gagtcctgag gcggaaagaa | 420 |
| ccagctgtgg aatgtgtgtc agttagggtg tggaaagtcc ccaggctccc cagcaggcag | 480 |
| aagtatgcaa agcatgcatc tcaattagtc agcaaccagg tgtggaaagt ccccaggctc | 540 |
| cccagcaggc agaagtatgc aaagcatgca tctcaattag tcagcaacca tagtcccgcc | 600 |
| cctaactccg cccatcccgc ccctaactcc gcccagttcc gcccattctc cgccccatgc | 660 |
| tgactaattt ttttattta tgcagaggcc gaggccgcct cggcctctga gctattccag | 720 |
| aagtagtgag gaggcttttt tggaggccta ggcttttgca aagatcgatc aagagacagg | 780 |
| atgaggatcg tttcgcatgg ccaagttgac cagtgccgtt ccggtgctca ccgcgcgcga | 840 |
| cgtcgccgga gcggtcgagt tctggaccga ccggctcggg ttctcccggg acttcgtgga | 900 |
| ggacgacttc gccggtgtgg tccgggacga cgtgaccctg ttcatcagcg cggtccagga | 960 |
| ccaggtggtg ccggacaaca ccctggcctg gtgtgggtg cgcggcctgg acgagctgta | 1020 |
| cgccgagtgg tcggaggtcg tgtccacgaa cttccgggac gcctccggga cggccatgac | 1080 |
| cgagatcggc gagcagccgt gggggcggga gttcgccctg cgcgacccgg ccggcaactg | 1140 |
| cgtgcacttc gtggccgagg agcaggactg aaataaaaat aaaaagctt | 1189 |

<210> SEQ ID NO 16
<211> LENGTH: 1843
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(1843)
<223> OTHER INFORMATION: Hygro

<400> SEQUENCE: 16

| | |
|---|---|
| ggccggccag atctactagt ctcgaggcta gcctgcagga gactctagat cataatcagc | 60 |
| cataccacat ttgtagaggt tttacttgct ttaaaaaacc tcccacacct cccccctgaac | 120 |
| ctgaaacata aaatgaatgc aattgttgtt gttaacttgt ttattgcagc ttataatggt | 180 |
| tacaaataaa gcaatagcat cacaaatttc acaaataaag cattttttc actgcattct | 240 |
| agttgtggtt tgtccaaact catcaatgta tctcaggtgg cacttttcgg ggaaatgtgc | 300 |
| gcggaacccc tatttgttta ttttctaaa tacattcaaa tatgtatccg ctcatgagac | 360 |
| aataaccctg ataaatgctt caataatatt gaaaaaggaa gagtcctgag gcggaaagaa | 420 |
| ccagctgtgg aatgtgtgtc agttagggtg tggaaagtcc ccaggctccc cagcaggcag | 480 |
| aagtatgcaa agcatgcatc tcaattagtc agcaaccagg tgtggaaagt ccccaggctc | 540 |
| cccagcaggc agaagtatgc aaagcatgca tctcaattag tcagcaacca tagtcccgcc | 600 |
| cctaactccg cccatcccgc ccctaactcc gcccagttcc gcccattctc cgccccatgc | 660 |
| tgactaattt ttttattta tgcagaggcc gaggccgcct cggcctctga gctattccag | 720 |
| aagtagtgag gaggcttttt tggaggccta ggcttttgca aagatcgatc aagagacagg | 780 |
| atgaggatcg tttcgcatgg gtaaaaagcc tgaactcacc gcgacgtctg tcgagaagtt | 840 |
| tctgatcgaa aagttcgaca gcgtctccga cctgatgcag ctctcggagg gcgaagaatc | 900 |
| tcgtgctttc agcttcgatg taggagggcg tggatatgtc ctgcgggtaa atagctgcgc | 960 |
| cgatggtttc tacaaagatc gttatgttta tcggcacttt gcatcggccg cgctcccgat | 1020 |
| tccggaagtg cttgacattg gggaattcag cgagagcctg acctattgca tctcccgccg | 1080 |
| tgcacagggt gtcacgttgc aagacctgcc tgaaaccgaa ctgcccgctg ttctgcagcc | 1140 |

```
ggtcgcggag gctatggatg cgatcgctgc ggccgatctt agccagacga gcgggttcgg    1200
cccattcgga ccgcaaggaa tcggtcaata cactacatgg cgtgatttca tatgcgcgat    1260
tgctgatccc catgtgtatc actggcaaac tgtgatggac gacaccgtca gtgcgtccgt    1320
cgcgcaggct ctcgatgagc tgatgctttg gccgaggact gccccgaag tccggcacct     1380 cgtgcacgcg gatttcggct ccaacaatgt cctgacggac aatggccgca taacagcggt    1440
cattgactgg agcgaggcga tgttcgggga ttcccaatac gaggtcgcca acatcttctt    1500
ctggaggccg tggttggctt gtatggagca gcagacgcgc tacttcgagc ggaggcatcc    1560
ggagcttgca ggatcgccgc ggctccgggc gtatatgctc cgcattggtc ttgaccaact    1620
ctatcagagc ttggttgacg gcaatttcga tgatgcagct tgggcgcagg tcgatgcga    1680 cgcaatcgtc cgatccggag ccgggactgt cgggcgtaca caaatcgccc gcagaagcgc    1740
ggccgtctgg accgatggct gtgtagaagt actcgccgat agtggaaacc gacgcccag     1800 cactcgtccg agggcaaagg aataaaataa aaataaaaag ctt                     1843
```

<210> SEQ ID NO 17
<211> LENGTH: 1346
<212> TYPE: DNA
<213> ORGANISM: Artificial Sequence
<220> FEATURE:
<223> OTHER INFORMATION: Chemically synthesized promoter - nucleotide
      sequence
<220> FEATURE:
<221> NAME/KEY: misc_feature
<222> LOCATION: (1)..(1346)
<223> OTHER INFORMATION: IL10

<400> SEQUENCE: 17

```
gaattcccta ggtcagtgtt cctcccagtt acagtctaaa ctggaatggc aggcaaagcc      60
cctgtggaag gggaaggtga aggctcaatc aaaggatccc cagagacttt ccagatatct     120
gaagaagtcc tgatgtcact gccccggtcc ttccccaggt agagcaacac tcctcgtcgc     180
aacccaactg gctccccttac cttctacac acacacacac acacacacac acacacacac     240
acacacacac aaatccaaga caacactact aaggcttctt tgggaagggg aagtagggat     300
aggtaagagg aaagtaaggg acctcctatc cagcctccat ggaatcctga cttctttttcc    360 ttgttatttc aacttcttcc accccatctt ttaaacttta gactccagcc acagaagctt     420
acaactaaaa gaaactctaa ggccaattta atccaaggtt tcattctatg tgctggagat     480
ggtgtacagt agggtgagga aaccaaattc tcagttggca ctggtgtacc cttgtacagg    540
tgatgtaata tctctgtgcc tcagtttgct cactataaaa tagagacggt aggggtcatg    600
gtgagcacta cctgactagc atataagaag ctttcagcaa gtgcagacta ctcttaccca    660 cttccccaa gcacagttgg ggtgggggac agctgaagag gtggaaacat gtgccggaga     720
atcctaatga aatcggggta aaggagcctg aacacatcc tgtgacccg cctgtactgt      780 aggaagccag tctctggaaa gtaaaatgga agggctgctt ggaactttg aggatattta     840 gcccaccccc tcattttttac ttggggaaac taaggcccag agacctaagg tgactgccta    900
agttagcaag gagaagtctt gggtattcat cccaggttgg ggggacccaa ttatttctca    960
atcccattgt attctggaat gggcaatttg tccacgtcac tgtgacctag aacacgcga    1020 atgagaaccc acagctgagg gcctctgcgc acagaacagc tgttctcccc aggaaatcaa    1080
ctttttttaa ttgagaagct aaaaaattat tctaagagag gtagcccatc ctaaaaatag    1140
ctgtaatgca gaagttcatg ttcaaccaat cattttttgct tacgatgcaa aaattgaaaa    1200
```

```
ctaagtttat tagagaggtt agagaaggag gagctctaag cagaaaaaat cctgtgccgg    1260
gaaaccttga ttgtggcttt ttaatgaatg aagaggcctc cctgagctta caatataaaa    1320
gggggagaga gaggtgaagg gtcgac                                         1346

<210> SEQ ID NO 18
<211> LENGTH: 890
<212> TYPE: DNA
<213> ORGANISM: Artificial Sequence
<220> FEATURE:
<223> OTHER INFORMATION: Chemically synthesized promoter - nucleotide
      sequence
<220> FEATURE:
<221> NAME/KEY: misc_feature
<222> LOCATION: (1)..(890)
<223> OTHER INFORMATION: CCL20

<400> SEQUENCE: 18
gaattcgtta tttgacattt gctgtgctga ctagctactg ctgataggtt ttctttccct      60
caacaattct gaggctctat attgagttat attagtacat catcatggag agttaaaggt     120
aggtaaggat tattttctga actgcaatat tgattaaagc catgtgaatg tataagattc     180
ttagaagagt tgacattaaa tcaaggtgaa gctgaggttt gagccttact taaaggctga     240
tattttccac tctaactgcg gacagtactg tagcactgtt atagtacctg ctctgaatgt     300
tagtctagca actcagggtc ttcttcatga cagctgaacc tcaaccatgt gatggtaaat     360
gtgtagcaga gtatgcctgg catcccacct gctcctcctc cccctcctcc ttgactggtt     420
ctggaaagca aatagggtgt aacaatagga gttctgaat gttcctgtgt ggggctgacc      480
tttgtatcgc tgttaatcct ctattttcag acacaaaaat gattaagtta aaactggatg     540
aaagtctttt ctgggtcaca gggctgagct gcttttgctc tttgcaaata caagaatttt     600
aacaggattc tccccttctc aacttcctgt ccccaccct gaccttcgca ccttcccaat      660
atgaggaaaa agcaggaagt tttccttgcg ggttttttt atgatgacat gatgggcca      720 gttgatcaat ggggaaaacc ccatgtggca acacgcttc tgtgtacatt cccaatattt      780
gctataaata gggccatccc aggctgctgt cagaatataa cagcactccc aaagaactgg     840
gtactcaaca ctgagcagat ctgttctttg agctaaaaac catgggatcc                890

<210> SEQ ID NO 19
<211> LENGTH: 2714
<212> TYPE: DNA
<213> ORGANISM: Artificial Sequence
<220> FEATURE:
<223> OTHER INFORMATION: Chemically synthesized promoter - nucleotide
      sequence
<220> FEATURE:
<221> NAME/KEY: misc_feature
<222> LOCATION: (1)..(2714)
<223> OTHER INFORMATION: ICAM-1

<400> SEQUENCE: 19
gtcgacggta cctgtagtct cagctacctg ggaggctgag gcaagagaat cgcttgaacc      60
tgggaagtag aggttgcagt gagccgagat tgcaccactg cactccagcc tgggcgacgg    120
agtgagacga cctcacaaaa atttacataa ataaaatgaa aagtaaaata aaatacaaa     180 agttggccgg gtgcgtttgc tcacgcctgt aatcccagca ctttgggagg gtgaggcagg    240
cagataatga ggtaagaaga tcgagaccat cctggctaac acggtgaaac cctgtctcta    300
ctaaaaatac aaaaaattag ctgtgcgtgg tgacacgcac ctgtagtccc agctatttgg    360
```

```
gaggctgagg caggagaatc acttgaacct gggaggtgga ggttgcagtg agccgagatc    420
gcaccactgc actccagcct gggccacaga gtgagactcc atcttgaaaa aaaaaaaaa    480 tacaaaagtt agccagggt gttggtgggt gcctgtaatc ccagctattt gggaggctaa    540
ggcagaagaa tttcttgaac ctaggaaacg gaggttgcag tgagccgaga tcacacctct    600
gtactccagc ctggacaaca gagcgagact ttgtctcaaa aaaaaaaaaa aaaaaaaact    660
aaataggccg ggagcagtgg ctcatgccta atcccagcc ctttgggagg ccaaggcagg    720
tggatcactt gaggtcagga gtttgagacc aggctggcca catggtgta accccgtctc    780 tactaaaaac acaaaattta gccgggtctg gtggcgtatg tctgtaatcc cagctactcg    840
ggaggctgag gcaggagaat cacttaaacc tgggaggcag gggttgcagt gagctgagat    900
cgtgccactg cactctagcc agggtgacag agtgaaactc tgtctcaaaa aattaaaaaa    960
gaaattcagc aagtaatgag ttaaggaatt cgaatattaa ggcgagtgac aaggaacgcc   1020
caggatgtgg cccaggatgg agtagggggg acactcattt aggagaaagc tcaggccaca   1080
agacaggagg agccagcctt gttggggttg aagggaagag cattccaggc tgagggaact   1140
gcaaggcgtt tgcatgggac actatgggat ggcttctgcc cttggtgggc agcctctggt   1200
ctgaggccat tctttggcct gcctgactgt ctggcaaccg ggaggaagcc ctgcccttcc   1260
tggagacaga acaaaggtc taggaaatat ctgcttccct tttccttgaa aaacgcttaa   1320
gggaacggag gactggagg tgccgtctct ctctgccagc ctgcccccta ccatagccat   1380
cccactccca tctcagaaag tgacccgcca tcctccaaaa ggctcggacc ctgatcaagg   1440
agtcatcccc cttgtcccag cacctccagt tggcccagcc tccaaaacgg atgtcaaatt   1500 cagcccttc ccaaggaca ctgcccagtc caggccccac tatcattcat ctggactaga   1560
acagtcacct cctctcccat ctcctggctg cagctcttga agcctcaact gggcccctgt   1620
gaacacttga gttagggcaa ggtccttcct ctgctcagaa ccctctatac ctcccacctc   1680
gctgggcata aaagccaaag tcctggccag gcacggtggc tcacatctgt tatcccagca   1740
ctttgggagg ccaaggggg cggatcacta gaggtcagga gttagagacc aacatggtga   1800
aaccccatct ctactaaaaa tacaaaaatt agctaggcgt ggtgacgcac ccctgtagta   1860
ccagctactc ggtaggctga ggtgggagaa tcgcttgaac ctgggaggca gagtttgcag   1920
tgagccgaga tcacaccact gtgctccagc ctgggtgaca aacgagact ggggttcaga   1980 aacaaacaaa caaaacaaca aagtcctcct caggtgacag gaacttgcac ctatctgccc   2040
tgtcatctcc ctgcccgctc ctctcctcga atctctcctt tgctaagcct gctccagcca   2100
cactgttctc ctggctgttc cttttttttt tttttgagt ctcactctca cccaggctgg   2160
agtgcagtgc ctctatcttg gctcactgca acctccgctg ccgggttcaa gagattctcc   2220
tgcatcagcc tcccaagtag gtggaattac aggtgtgcac caccacaccc ggctaatttt   2280 tgtatttgc atagagatgg gggtctccct atgttgccca ggctggtctt gaactcctgg   2340
gctcaagtga tcctcccatc tcggcctccc aaaatgctgg gattacaggt gggagccgcg   2400
cccaggtgga ttttgtctga ctctgttcat tcctgtgtcc ccagtacctg aaggacgcca   2460
agcacacagt aggcgcttaa aaaacattga gccacatgtt gagaaaagaa cggcaccatt   2520
gtggctgcaa gtgggacttg ggccgcgcgg gggacgtcgc gcacctcggg ccggggcaag   2580
agctcagtgg aacccgcccg aggaagaacc cgtggcgcag gattttccca ggccttctga   2640
ggaccagggg cgtccccgt cccaccctgt gactttgctc aggcgttccg gggcgggaat   2700
tcagaactgg atcc                                                    2714
```

<210> SEQ ID NO 20
<211> LENGTH: 1841
<212> TYPE: DNA
<213> ORGANISM: Artificial Sequence
<220> FEATURE:
<223> OTHER INFORMATION: Chemically synthesized promoter - nucleotide sequence
<220> FEATURE:
<221> NAME/KEY: misc_feature
<222> LOCATION: (1)..(1841)
<223> OTHER INFORMATION: TGF-beta

<400> SEQUENCE: 20

```
gaattcggca ggaatttttg tctgccatcc atgttcatgt ctgccgtgtc cccagctagc      60
tagaacagag tctagcacag gagaagggat cagcatgaga tgagatgggg ctggatctcc     120
aagggctttg actaccagac tgaggagctg aactgtgttc tgaggacatg ggcaaagcta     180
tggaaggaga gaaagatgct tccagatgcc aggtggaagg tggattagag aggggcaaga     240
aagaaggccc tgggcccaaa gggagcaggg caggacatg aggagggaag gcaggaggtg      300
tccctgacaa ggcccatgat ggttacctgg ggactggagg agcaatgggc tgccctgaca     360
tggggtcatg gaggaggata acacagagag gaaattcagc agaggtctga ttagaagggc     420
cttgaatgtt gaagaggttg gactttatac tgagggcact ggggagctat ggaaggatcc     480
ttagcagggg agtaacatgg atttggaaag atcactttgg ctgctgtgtg gggatagata     540
agacggtggg agcctagaaa ggaggctggg ttggaaactc tgggacagaa acccagagag     600
gaaaagactg ggcctggggt ctccagtgag tatcagggag tggggaatca gcaggagtct     660
ggtccccacc catccctcct ttccctctc tctcctttcc tgcaggctgg ccccggctcc     720
atttccaggt gtggtcccag gacagctttg ccgctgcca gcttgcaggc tatggatttt     780
gccatgtgcc cagtagcccg ggcacccacc agctggcctg ccccacgtgg cggcccctgg     840
gcagttggcg agaacagttg gcacgggctt cgtgggtgg tgggccgcag ctgctgcatg     900
gggacaccat ctacagtggg gccgaccgct atcgcctgca cacagctgct ggtggcaccg     960
tgcacctgga gatcggcctg ctgctccgca acttcgaccg ctacggcgtg gagtgctgag    1020
ggactctgcc tccaacgtca ccaccatcca caccccggac acccagtgat gggggaggat    1080
ggcacagtgg tcaagagcac agactctaga gactgtcaga gctgacccca gctaaggcat    1140
ggcaccgctt ctgtcctttc taggacctcg gggtccctct gggcccagtt tccctatctg    1200
taaattgggg acagtaaatg tatggggtcg cagggtgttg agtgacagga ggctgcttag    1260
ccacatggga ggtgctcagt aaaggagagc aattcttaca ggtgtctgcc tcctgaccct    1320
tccatccctc aggtgtcctg ttgccccctc ctcccactga caccctccgg aggcccccat    1380
gttgacagac cctcttctcc taccttgttt cccagcctga ctctccttcc gttctgggtc    1440
cccctcctct ggtcggctcc cctgtgtctc atccccggga ttaagccttc tccgcctggt    1500
cctctttctc tggtgaccca caccgcccgc aaagccacag cgcatctgga tcaccccgctt   1560
tggtggcgct tggccgccag gaggcagcac cctgtttgcg gggcggagcc ggggtgcccg    1620
ccccctttcc cccagggctg aagggacccc ctcggagcc cgcccacgcg agatgaggac     1680
ggtggcccag cccccccatg ccctccccct ggggccgcc ccgctcccg cccgtgcgc       1740
ttcctgggtg gggccggggg cggcttcaaa ccccctgcc gacccagccg gtccccgccg    1800
ccgccgccct tcgcgccctg ggccatctcc ctcccgtcga c                        1841
```

```
<210> SEQ ID NO 21
<211> LENGTH: 771
<212> TYPE: DNA
<213> ORGANISM: Artificial Sequence
<220> FEATURE:
<223> OTHER INFORMATION: Chemically synthesized promoter - nucleotide
      sequence
<220> FEATURE:
<221> NAME/KEY: misc_feature
<222> LOCATION: (1)..(771)
<223> OTHER INFORMATION: c-fos

<400> SEQUENCE: 21
gaattcgcag ccgggcggcc gcagaagcgc ccaggcccgc gcgccacccc tctggcgcca      60
ccgtggttga gcccgtgacg tttacactca ttcataaaac gcttgttata aaagcagtgg     120
ctgcggcgcc tcgtactcca accgcatctg cagcgagcaa ctgagaagcc aagactgagc     180
cggcggccgc ggcgcagcga acgagcagtg accgtgctcc tacccagctc tgcttcacag     240
cgcccacctg tctccgcccc tcggcccctc gccggctttt gcctaaccgc cacgatgatg     300
ttctcgggct tcaacgcaga ctacgaggcg tcatcctccc gctgcagcag cgcgtccccg     360
gccggggata gcctctctta ctaccactca cccgcagact ccttctccag catgggctcg     420
cctgtcaacg cgcaggtaag gctggcttcc cgtcgccgcg gggccggggg cttgggtcg     480 cggaggagga gacaccgggc gggacgctcc agtagatgag taggggctc ccttgtgcct      540 ggagggaggc tgccgtggcc ggagcggtgc cggctcgggg gctcgggact tgctctgagc     600
gcacgcacgc ttgccatagt aagaattggt tccccttcg ggaggcaggt tcgttctgag      660
caacctctgg tctgcactcc aggacggatc tctgacatta gctggagcag acgtgtccca     720
agcacaaact cgctaactag agcctggctt cttcggggag gtggcggatc c              771

<210> SEQ ID NO 22
<211> LENGTH: 332
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(332)
<223> OTHER INFORMATION: AB-repeat

<400> SEQUENCE: 22
gtcgacttct cttcaaactt ttccgctttt agagagagcg ccaaaaccta ttatcttaag      60
tcgctgccga ttctcttcaa acttttccgc ttttggtcga tgcgccaaaa cctattatct     120
taagtcctgg attgttctct tcaaactttt ccgcttttgc ctggaacgcc aaaacctatt     180
atcttaagtc ggcgttaatt ctcttcaaac ttttccgctt tttttaaagg cgccaaaacc     240
tattatctta agtcatttgc ggttctcttc aaacttttcc gcttttgatg gccacgccaa     300
aacctattat cttaagtctg aacgctctcg ag                                   332

<210> SEQ ID NO 23
<211> LENGTH: 308
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(308)
<223> OTHER INFORMATION: AC-repeat

<400> SEQUENCE: 23
```

```
gtcgacttct cttcaaactt ttccgctttt agagagagag gagttgtgtt tgtggacgtg      60
ccagcattct cttcaaactt ttccgctttt ggtcgatgag gagttgtgtt tgtggactag     120
cgtacttctc ttcaaacttt tccgcttttg cctggaaagg agttgtgttt gtggacaaat     180
cgcattctct tcaaacttt ccgcttttt taaaggagga gttgtgtttg tggaccattg       240
aagttctctt caaactttc cgcttttctg acggcaggag ttgtgtttgt ggacggggtc     300
agctcgag                                                              308

<210> SEQ ID NO 24
<211> LENGTH: 307
<212> TYPE: DNA
<213> ORGANISM: Artificial Sequence
<220> FEATURE:
<223> OTHER INFORMATION: Chemically synthesized nucleotide sequence
<220> FEATURE:
<221> NAME/KEY: misc_feature
<222> LOCATION: (1)..(307)
<223> OTHER INFORMATION: CB-repeat

<400> SEQUENCE: 24
gtcgacagga gttgtgtttg tggacgtgcc agccgccaaa acctattatc ttaagtcgtg      60
gtcataggag ttgtgtttgt ggactagcgt accgccaaaa cctattatct taagtctaaa    120
gatgaggagt tgtgtttgtg gacaaatcgc acgccaaaac ctattatctt aagtcgtgga    180
tgtaggagtt gtgtttgtgg acattcacct cgccaaaacc tattatctta agtcccgcgc    240
ttaggagttg tgtttgtgga ccattgaagc gccaaaacct attatcttaa gtctgaacgc    300
tctcgag                                                              307
```

SINGLE CELL BASED REPORTER ASSAY TO MONITOR GENE EXPRESSION PATTERNS WITH HIGH SPATIO-TEMPORAL RESOLUTION

The invention relates to an assay to monitor gene expression patterns, especially in a living cell, having recourse to a transcription reporter system. The assay of the invention offers means suitable for a rapid and high spatio-temporal resolution of said patterns. The assay of the invention may further be used for quantitative monitoring of gene transcription.

The invention provides especially the possibility to perform the designed assay in single cells. It provides also especially the possibility to perform the designed assay in a living cell.

Thus, the invention provides an assay that enables one to monitor RNA production, if appropriate a particular mRNA, in a living cell.

The field of applications of the invention encompasses monitoring gene expression in order to determine or monitor regulation of cell homeostasis, cell activity or deregulation of cell homeostasis or activity or other cellular processes.

The invention enables in particular monitoring gene expression in cells that have been challenged by extracellular events such as stress caused by pathogen agents or organisms, drugs, or chemicals. Cells for use according to the invention encompass any kind of prokaryotic or eukaryotic cells. In a particular aspect of the invention these cells may be obtained from a host, especially a mammalian host, in particular a patient affected with a pathological condition. It also encompasses the determination of host/pathogen interactions, in living cell.

The invention thus provides means suitable for high throughput and high content screening.

It thus provides tools for use in drug development strategies, and more generally enables monitoring gene expression in living cells and enables gene profiling for screening purposes. Particular applications of the invention include monitoring cells of a patient infected with pathogenic organisms or agents, such as bacteria, viruses, parasites. The assayed cells may as such be infected or not. The invention also provides means for monitoring immunological reactions in a cell or for monitoring the development or establishment of tumor cells.

Living cells are in constant communication with their environment requiring the adaptation of their physiology to the specific circumstances. These communication events play an important role (i) for the crosstalk between individual cells of one organism (for example during development), or (ii) for the effective response to stress from the outside. Stress can be physical (for example heat), chemical (for example toxic chemicals), or biochemical (for example pathogenic bacteria).

In general, cells alter the expression of specific genes to adjust themselves during the situations described above. Particularly, gene expression is highly temporally regulated allowing a balanced cellular response to stress. Disruption of this balance leads to disease.

In the case of stress caused by pathogens, these stressors have developed strategies to specifically target and disrupt host cellular gene expression (Arbibe, L. et al. An injected bacterial effector targets chromatin access for transcription factor NF-kappaB to alter transcription of host genes involved in immune responses. *Nat Immunol* 8, 47-56 (2007)). This can lead to an interference with the host immune response, and to the escape of the pathogen of the host immune surveillance (for example *Mycobacterium tuberculosis*) (Monack D M, Mueller A, Falkow S. Persistent bacterial infections: the interface of the pathogen and the host immune system. Nat Rev Microbiol. 2004 September; 2(9):747-65). Similar distortions occur during misregulation in auto-immune diseases (for example Arthritis or Lupus) (Kyttaris V C, et al. Immune cells and cytokines in systemic lupus erythematosus: an update. Curr Opin Rheumatol. 2005 September; 17(5):518-22).

Therefore, a precise understanding of the finely tuned gene expression responses is pivotal to understand the molecular basis of cellular reactions to stress, or the specificities of the regulated cellular steps during development.

The post-genomic era has provided us with a wealth of information from various genomic systems, enabling analysis of the complexity of biological processes on a large scale, and with high throughput (Barabasi, A. L. & Oltvai, Z. N. Network biology: understanding the cell's functional organization. *Nat Rev Genet.* 5, 101-113 (2004)). Examples of these are protein analysis by mass spectrometry, and transcription and expression profiling by protein and DNA microarrays (Pepperkok, R. & Ellenberg, J. High-throughput fluorescence microscopy for systems biology. *Nat Rev Mol Cell Biol* 7, 690-696 (2006)).

Understanding the interactions between the components of a biological system and how they give rise to function is a key aim when studying systems biology. Most of our current information on the activation of downstream genes in many signal transduction cascades is derived from microarray data or protein gene reporter assays (Pepperkok, R. & Ellenberg, J. High-throughput fluorescence microscopy for systems biology. *Nat Rev Mol Cell Biol* 7, 690-696 (2006)). Microarray approaches are able to provide population or "census" information for the behaviour of millions of cells. However each cell is most likely engaged in a different phase of response to the signalling cascade and what is measured is a more global and general picture. Within this mosaic picture lies information as to when specific cells are engaged in specific phases of their gene response. Theoretically this can be temporally related to when the pathway is activated and assist in building mechanistic models of how such dynamic signal transduction cascades function. However accurate temporal information on such transcriptional response is masked in the "noise" or stochastic variations of the microarray data.

Exploring macromolecules in their natural environment with high spatial and temporal resolution has become possible through the use of fluorescence-based imaging assays in living cells (Pepperkok, R. & Ellenberg, J. High-throughput fluorescence microscopy for systems biology. *Nat Rev Mol Cell Biol* 7, 690-696 (2006), Bastiaens, P. I. & Pepperkok, R. Observing proteins in their natural habitat: the living cell. *Trends Biochem. Sci.* 25, 631-637 (2000); Meyer, T. & Teruel, M. N. Fluorescence imaging of signaling networks. *Trends Cell Biol.* 13, 101-106 (2003); Wouters, F. S., Verveer, P. J. & Bastiaens, P. I. Imaging biochemistry inside cells. *Trends Cell Biol.* 11, 203-211 (2001). In principle, they can be used to explore proteins in their natural habitat, interrogating their biochemical interactions. However this has not been easily extended to imaging dynamics of gene expression, for example through observation of transcription of messenger RNA. Examining this activity on the single cell level would permit the temporal relationship between activation of a signal transduction cascade (the biochemical events) and a specific transcriptional response to be accurately related.

Though this has been attempted with gene reporter assays such as fluorescent protein or luciferase assays, what is measured is the translational and not transcriptional readout of a single gene in what is most likely hundreds of genes engaged in a transcriptional response. The kinetics of gene expression however cannot be directly inferred by the appearance of a protein as there is a lag between transcription of mRNA and translation to protein. Since translation is delayed from transcription, the ability to draw exact temporal relationships between genes may remain unsuccessful. As a result despite copious amounts of data, the temporal relationship between functional pathways activation remains unclear. These deficiencies have especially been observed when studying temporal relationships between immune pathways and inflammatory pathways (Karin, M. Nuclear factor-kappaB in cancer development and progression. *Nature* 441, 431-436 (2006); Karin, M., Lawrence, T. & Nizet, V. Innate immunity gone awry: linking microbial infections to chronic inflammation and cancer. *Cell* 124, 823-835 (2006)). To date, no genetically encoded tag exists that could be used to label mRNA in a similar way as GFP and comparable proteins.

High content screening allows for the evaluation of multiple biochemical and morphological parameters in cellular systems, if biological readouts in the system are amenable to quantitative data collection in vivo. By combining the imaging of single cells with image analysis algorithms, individual components of the biological system are assigned quantitative properties (Genovesio, A., Belhassine, Z. & Olivo-Marin, J. Adaptive gating in Gaussian Bayesian multi-target tracking. *Image Processing*, 2004. ICIP '04. 2004 *International Conference on* 1 (2004), Bork, P. & Serrano, L. Towards cellular systems in 4D. *Cell* 121, 507-509 (2005); Genovesio, A., Zhang, B. & Olivo-Marin, J. Interacting multiple model based method to track moving fluorescent biological spots. *Biomedical Imaging: Macro to Nano*, 2004. *IEEE International Symposium on*, 1239-1242 (2004); Olivo-Marin, J. Extraction of spots in biological images using multiscale products. *Pattern Recognition* 35, 1989-1996 (2002)). Thus, the nature of the dynamic system can be modelled, permitting true systems biology.

Currently we are able to collect quantitative information for protein interactions in signal transduction pathways in living cells using image-based approaches (Starkuviene, V. High-content screening microscopy identifies novel proteins with a putative role in secretory membrane traffic. *Genome Res.* 14, 1948-1956 (2004); Liebel, U. A microscope-based screening platform for large-scale functional protein analysis in intact cells. *FEBS Lett.* 554, 394-398 (2003); Bastiaens, P. I. & Pepperkok, R. Observing proteins in their natural habitat: the living cell. *Trends Biochem. Sci.* 25, 631-637 (2000)). However, in vivo single cell based transcriptional information at the mRNA level that reports quantitative levels of transcriptional activity in a signal transduction cascade, in response to a given stimulus or in differing genetic backgrounds, is not yet a reality. Achieving this goal will enable the accurate modeling of transcription in signal transduction cascades.

The ability to follow and track individual mRNA complexes in vivo (i.e., in a living cell) has undergone significant advances. Most approaches suffer however from an inability to covisualize proteins involved in signal transduction cascade events simultaneously with the mRNA that is being tracked in space and in real-time. A further advance would enable spatiotemporally resolved studies to understand the orchestrated relationship between signal transduction proteins involved in gene expression, and would allow the precise determination of the time points at which gene expression begins, the quantification of that expression and the development of quantitative models of gene expression.

Transport of individual transcripts has recently become possible using the MS2 reporter system. For this approach, one plasmid encodes a green fluorescent protein (GFP) fused to the coding sequence for the single-stranded phage RNA phage capsid protein, MS2. The MS2 capsid protein has a high affinity for a specific RNA sequence with a short stem-loop structure (MS2 binding sequence) encoded by the phage. The second plasmid contains the MS2 binding sequence multimerized in either 6, 12 or 24 copies. Both plasmids are cotransfected into cells or alternatively cell lines for the inducible expression of GFP-MS2. Even though, individual transcripts can be tracked with this approach, monitoring the rate of transcription is problematic because the GFP-MS2 protein fluoresces also in the absence of transcripts. Therefore, it is not suited for quantitative studies of transcriptional profiling (Bertrand, E. et al. Localization of ASH1 mRNA particles in living yeast. *Mol Cell* 2, 437-445 (1998); Shav-Tal, Y. et al. Dynamics of single mRNPs in nuclei of living cells. *Science* 304, 1797-1800 (2004)).

Molecular beacons, nucleotide probes that fluoresce only upon hybridizing specifically to complementary mRNA sequences, present a general solution to the problem of visualizing gene expression (Tyagi, S. & Kramer, F. R. Molecular beacons: probes that fluoresce upon hybridization. *Nat Biotechnol* 14, 303-308 (1996)). In conjunction with fluorescent proteins and differing light microscopy and image analysis techniques they offer a possibility to be used in quantitative biology. Improvements are however still needed to enable relevant visualization and analysis of the signal delivered by these probes, especially when quantitative determination of hybridized probes is contemplated.

Several constraints exist to performing similar hybridization assays in living cells, chief among them, the ability of the probe to successfully pair with mRNA sequences which are found in complex secondary structures in vivo. In addition since the target nucleic acid is not immobilized or fixed prior to the introduction of the probe, dynamic interactions of mRNA with proteins and ribosomes are constantly occurring, meaning that many regions of the mRNA polymer are engaged in interactions with other cellular actors.

Previously, individual mRNA transcripts were tracked inside living cells using a construction that contained 96 beacon binding sites that were fused to a modified tetracycline response element in conjunction with a minimal CMV promoter (Vargas D. Y. et al, Mechanism of mRNA transport in the nucleus, PNAS vol. 102, no. 47, 17008-17013 (2005)). Such construction is not recognized by the transcriptional machinery inside eukaryotic cells to induce the reporter. Rather, this reporter system requires the presence of an engineered factor, the tetracycline-controlled transactivator. This transactivator consists of an engineered version of the bacterial Tet repressor molecule and repeats of a minimal VP16 transactivation domain. This reporter system is used to guaranty tightly regulated transcription depending on the amount of tetracycline added to the cells. Taken together, this reporter system does not allow the study of the expression of endogenous genes in eukaryotic cells from their natural promoter, and it requires the presence of (i) engineered factors to activate transcription, and of (ii) tetracycline as inducer of transcription.

The invention provides an assay that overcomes the drawbacks of known assays as described above based on reporter proteins, for example fluorescent reporter proteins, which introduce an unpredictable experimental time-delay caused by protein maturation. In this context, the inventors have developed a method and suitable tools and products to investigate the transcriptional changes in real time at the single cell level that is based on highly sensitive nucleic acid based reporters.

The invention provides means suitable to enhance the study of systems biology, by developing an imaging technology that represents a breakthrough in the imaging of gene expression in vivo i.e., in living cells, especially suitable for gene profiling in individual, i.e., single cells.

The methods, assays and products of the invention offer a way for systematic tagging of mRNAs in living cells, especially in routine practice.

The tags used to perform the invention are nucleic acid based tags, empirically defined and nevertheless suitable for systematic use for profiling of many genes.

The methods, assays and products of the invention are designed to permit not only the advancement of systems biology but most importantly, basic and clinical research.

All cellular processes in living cells are regulated via the tightly orchestrated expression of specific subsets of genes. De-regulation of gene expression leads to a disruption of the homeostasis of gene expression and eventually to disease. This may be monitored having recourse to the invention.

Importantly, pathogens or drugs often interfere with signalling pathways potentially altering the cellular gene expression pattern. The invention enables monitoring such interferences on cellular gene expression on the transcriptional level.

Gene expression programs change rapidly in living cells provoking tremendous technical challenges for their study. Fully realized, the invention enables the routine study of cell homeostasis and, according to one aspect, identification of transcriptional responses associated with infection and disease, development and immune response. It may especially assist in the identification of pathways and regulatory networks of genes that are expressed in diseases, immune response and during growth and development.

In order to fulfil this aim, the invention provides a double-stranded polynucleotide comprising on its positive strand considered from its 5' end to its 3' end, (i) a promoter of a gene of interest or several promoters of various genes of interest, and, (ii) one or several so-called barcode(s) wherein each barcode contains at least one barcode unit formed of at least one and preferably multiple recognition binding sites, each recognition binding site being composed of a nucleotide sequence, and wherein each of said barcode is under the control of at least one of said promoter(s) for transcription.

The recognition binding site(s) or the complementary nucleotide sequence may be recognized and bound by a single detection probe, i.e., a molecular probe (nucleic acid based probe).

In a particular embodiment, the number of recognition binding sites may be more than 1 and up to 500. It may especially be above 100.

Accordingly, when the barcode comprises 2 or more recognition binding units, each binding unit is recognized by a single detection probe.

In a particular embodiment, the barcode unit or at least one of the several barcode units of the barcode is constituted by a plurality of recognition binding sites which are all identical to each other.

In accordance with the invention, the transcripts of the nucleic acid constituting the barcode expressed under the control of the promoter(s), are detected with a detection probe, especially a nucleic acid based detection probe (molecular probe). Said detection probe recognizes the transcript of the recognition sites of the barcode(s).

What is disclosed herein with reference to a promoter, a recognition binding site, a barcode unit, a barcode, a gene of interest in the polynucleotide, may similarly apply to several or to all these entities when associated in one polynucleotide or when present in various polynucleotides.

The features of the polynucleotide defined herein are possibly present in the polynucleotide independently of each other or in any possible combinations with each other.

It is especially pointed out that, except where expressly excluded, any of these features, including the features disclosed in the examples, may be combined to provide a particular embodiment of the defined polynucleotide.

The promoter contained in the polynucleotide is one of a gene of interest selected among genes which are endogenous to a determined cell wherein gene profiling is studied in accordance with the invention.

A particular polynucleotide is designed in such a way that in a barcode, at least 2 of the recognition binding sites are contiguous and/or at least 2 of the barcode units are contiguous.

In another particular polynucleotide, in a barcode unit, at least 2 of the recognition binding sites are separated by a spacer and/or at least 2 of the barcode units are separated by a spacer.

These definitions of particular polynucleotide constructs encompass any possibility of combination of contiguous and/or separated recognition binding sites or barcode units or barcodes, provided the obtained construct enables the detection signal to be detected and especially switched on when the barcodes especially its transcript, hybridizes with a nucleic acid based detection probe, in appropriate conditions.

When used to assay gene profiling in a cell, by studying transcription of mRNA driven by the promoter of the polynucleotide of the invention, the hybridization reaction with the detection probe occurs with the RNA transcript of the polynucleotide, or part thereof.

For determination of the detection probe ability to be used in the assay of the invention, hybridization capacity may be tested with the polynucleotide of the invention, provided as single-stranded molecule. For convenience, if reference is made in the present application to hybridization with the polynucleotide it should be understood as encompassing hybridization with one strand of the polynucleotide, or in the context of the performance of the gene profiling expression assay of the invention, with its transcript.

The double-stranded polynucleotide is a DNA sequence which, at some stage in the applications of the invention, especially to achieve test hybridization, may be present, transcribed or used as a single-stranded DNA or RNA polynucleotide. To the extent that it is technically relevant, the features disclosed with respect to the double-stranded polynucleotide apply to its single-stranded DNA or RNA version.

The double-stranded polynucleotide of interest is suitable and used in a cell which naturally harbours and possibly expresses the gene of interest whose promoter is used in the polynucleotide construct.

In a particular embodiment of the invention, the double-stranded polynucleotide is designed in such a way that its 5' end (on its positive strand) essentially starts with a promoter sequence of a gene of interest and its 3' end essentially terminates with the sequence of a recognition binding site. Accordingly, such a particular polynucleotide of the invention is framed by the herein disclosed promoter and recognition binding site and either does not contain any further 5' and 3' sequences or only contains further 5' and/or 3' nucleotides which represent endonuclease restriction site(s) or a part thereof, useful for a cloning step. Between said starting promoter and terminating recognition binding site, the polynucleotide may comprise additional successive recognition binding site(s) and promoter sequence(s) so that a barcode made of recognition binding sites, possibly arranged in barcode units, is necessarily under the expression control of a promoter located upstream. It is also possible that the polynucleotide contains further 3' sequences, such as, for illustration, a poly A tail and/or a 3'-transcription termination signal. The polynucleotide may also comprise sequences of the gene of interest which are more distal sequences to the promoter, such as that of an enhancer region and/or other expression regulatory sequences. The promoter sequence is, according to the standard definition, a region in the gene that determines the starting point of the transcription and enables the recognition and binding of the transcription factor(s) and, directly or indirectly, the recognition and binding of the polymerase(s) of the cell, enabling RNA extension. The promoter generally comprises a TATA box sequence.

In a particular embodiment, the promoter is one from a eukaryotic gene.

Furthermore, polynucleotides or fragments of a polynucleotide of the invention made of a promoter and a barcode may further contain coding DNA sequences of interest, including sequences for expression of a reporter protein, and/or a coding sequence of the gene providing the promoter. Such polynucleotide fragments may be adjacent to each other in the polynucleotide or may be spaced by further nucleic acid sequences.

A recognition binding site as herein disclosed comprises or consists in a nucleotide sequence, especially a DNA sequence, which, especially whose transcript, is suitable for recognition by another polynucleotide constituting a nucleotide-based probe, such as a complementary nucleotide sequence capable of base pairing with said recognition binding site, especially with its transcript. When the polynucleotide of the invention is used, the transcript of the recognition binding site is expressed and is recognized by the probe in a manner sufficient to allow base pairing with the probe to give rise to a measurable change at the level of the transcript of the polynucleotide that may be detected.

In a particular aspect of the invention, the recognition binding site(s) of the barcode is (are) beacon binding site(s), i.e., sites which are recognized and suitable for binding with beacon probes. According to this aspect, the barcode is a beacon barcode recognized by one or several beacon probe(s). Beacon probes are disclosed with more details hereafter.

According to the invention, the expression "a gene of interest" pertains to a nucleotide sequence or construct, including a transcription unit, which can be transcribed and translated in appropriate environmental conditions especially in a cell, to encode a polypeptide (whatever its length). In a preferred embodiment, a gene of interest is a cellular structural gene, an accessory gene or regulatory gene or any other gene relevant for the homeostasis, the regulation or metabolism of the cell.

The gene of interest providing the promoter of the polynucleotide of the invention is endogenous in the cell wherein the polynucleotide is introduced for polynucleotide transcription study and thus provides a native promoter, i.e., one naturally harbouring the capacity to function as a promoter in a gene of a cell. Accordingly, the promoter is said to be endogenous to said cell. By this expression it is also meant that the promoter is recognized by the internal transcription machinery of the cell (especially of the eukaryotic cell), including the transcription factor(s) and polymerase(s) of the cell, without the need for bringing external transcription factors or other expression regulatory components. In other words, the promoter is a natural promoter of the cell wherein its transcription activity is studied or is derived from such a promoter as disclosed herein. For the purpose of the invention such a native or natural promoter may be altered and especially mutated by addition, deletion, insertion of one or several nucleotides, to study the impact of such alteration when using such a variant promoter in the polynucleotide.

Examples of genes of interest according to the invention are especially genes involved in a therapeutic strategy. In a particular embodiment, they may be a target for or activated or inhibited by, either directly or indirectly, a pathogenic organism or agent, or a target for or activated or inhibited by, either directly or indirectly, a drug. They may be as such a drug or a drug candidate.

Within this definition of a "gene of interest" and therefore of the promoter inserted in the double-stranded polynucleotide of the invention, endogenous genes of a cell, either a prokaryotic or a eukaryotic cell, useful to carry out the invention, are the genes which are involved, either directly or indirectly, in a response to extracellular stimuli, especially to extracellular stress, such as that induced by pathogen organisms or agents or by physical stimuli such as heat or toxic chemical or biochemical compounds or pathological conditions.

In a particular embodiment genes of a determined cell that are affected by the disruption of cell gene expression or involved in dis-regulation of gene expression may be genes of interest.

Examples of endogenous genes of specific cells of interest are genes involved in the homeostasis or in the development of the particular studied cells or of the entire organism comprising these cells, including but not limited to genes involved in the immune system, genes induced or silenced in pathologic conditions such as in tumor or cancer states.

Particular examples for such genes are genes encoding immunoglobulins or antigen-binding fragments thereof, especially genes encoding variable fragments of heavy chains of antibodies having an antigen-binding capacity.

Other examples include genes encoding receptors, either cellular receptors or soluble receptors, including receptors found on T lymphocytes.

Particular examples of genes of the immune system that may be targeted for gene profiling encompass TgF-β, C-fos, ICAM, in particular ICAM-1, CCL20, Interferon gamma genes.

Other genes of interest for gene profiling include interleukin genes, e.g. IL10 and IL8 genes.

Further examples of genes of interest are genes encoding Tumor Associated Antigens., particularly genes involved in Leukemia as listed below:

For illustration purpose, the following genes indicative of adoption of LSC Fate, may be studied:
L-GMP Marker Genes ('Early') Mouse: Meis1, HoxA9, HoxA10, MYLK, HoxA5, Stau2; and for MLL-AML Marker Genes Human: Meis1, HoxA9, HoxA10, HoxA5. In another example, highly expressed genes in ALL, MLL and AML leukemias as the following may be profiled:
ALL Marker Genes: MME (CD10), CD24, DYRK3, FOXO1A.

MLL Marker Genes: FLT3, KIAA0428, NKG2D, ADAM-10, PROML-1, KIAA1025, LGALS-1, CCNA-1, DKFZp586O0120, ITPA, CDNAag36C04, KIAA0920, LMO-2.

AML Marker Genes: GJB-1, BSG, ENSA, CTSD, DF, TFDP-2, DRAP-1, NF2, CDNA20C10, PDE3B, ANPEP, Chrm19clone, Chrm22q11clone, RTN2, CRYAA.

The expression "promoter" or "promoter sequence" thus designates, according to the invention, a DNA sequence present in a construct which is suitable to provide, in a cell wherein a gene comprising such a promoter is normally endogenous and native, activation of transcription of a DNA sequence placed under its control in the polynucleotide of the invention, as a result of recognition and binding of cellular transcription factor(s) and polymerase(s) of said cell. The promoter of the gene is naturally capable of being recognized and activated by the machinery of the cell wherein transcription or expression is assayed after transfection of said cell with the polynucleotide construct.

A promoter sequence appropriate to carry out the invention, can be a natural promoter of a native gene of interest. Alternatively it may be derived from an endogenous promoter as described herein and accordingly is a modified promoter, especially having a mutated sequence for example by deletion, insertion and/or substitution of one or several, of its nucleotides, and whose transcription activity should be examined. Accordingly, for the purpose of the invention, access to the endogenous promoter of the gene of interest or to the information provided by its nucleotide sequence, is required to allow its identification in view of its preparation to test the activity of the promoter or to test the activity of a modified counterpart of said promoter, whereas access to the entire sequence of the gene or even to its coding sequence may be not necessary. More generally the invention provides means to assay the putative transcriptional activity of any nucleotide fragment in a cell that may be a candidate promoter. The sequences replying to these various definitions for the promoter may be prepared by synthesis (chemical synthesis or amplification, e.g. by PCR) or may be cloned according to any available technique.

The endogenous promoter is advantageously a promoter of a eukaryotic gene. The cell wherein transcription or expression is studied is thus advantageously a eukaryotic cell.

A promoter such as a doxycycline responsive promoter as disclosed in Vargas D. Y. et al, PNAS, 2005 is neither a native promoter according to the invention nor a variant promoter as defined herein.

The "promoter" as defined herein consists of the DNA fragment having the disclosed activity to trigger transcription activation or comprises said DNA fragment. Preferably it is devoid of the whole coding sequence (i.e., the sequence which is transcribed as a premature mRNA or as a mRNA) of the gene of interest, or it only comprises less than 20% of the coding sequence of the gene of interest. The promoter sequence is especially not a DNA sequence that is transcribed as a pre-mRNA in a cell expressing the gene.

According to a particular embodiment of the invention, the promoter activity is tested without elicitation or interaction of any molecule heterologous to or molecule brought in contact with the cell wherein the transcription is studied. By "heterologous" it is intended a molecule which is not naturally expressed by said cell. A molecule brought into contact with the cell is added for the purpose of the assay.

According to another embodiment, the transcription activity of the promoter of the double-stranded polynucleotide construct is tested under elicitation or influence of a molecule which is heterologous to the cell or a molecule brought in contact with the cell and whose interaction capacity, either direct or indirect, with the transcription activity of the promoter of the gene of interest in the polynucleotide of the invention is studied. Such molecules are provided for illustration in the examples and especially comprise cytokines, interleukins or chemokines, such as interleukins TNFα, IL-1.

In a particular embodiment of the invention, the promoter of a gene of interest is selected from the group of promoters of endogenous genes such as chemokine genes, especially promoters of the interleukin 8 gene or of the interleukin 10 gene or of the CCL20 gene, promoters of interferon genes, especially promoter of the gamma interferon gene, or a promoter of a gene of a tumor associated protein.

Other promoters cited as examples are promoters of TGFβ, ICAM or c-fos genes.

In a particular embodiment of the invention, the promoter of a gene of interest is elicited via a molecule present or expressed inside the assayed cells via an autocrine mechanism.

According to another embodiment, the transcription activity of the promoter of the double-stranded polynucleotide construct is elicited or influenced by an agent, especially a pathogenic agent that is studied for its possible, direct or indirect, interaction with said promoter activity.

According to the invention, a "barcode" is a DNA construct which contains at least one recognition binding site, i.e., a site suitable for being recognized and for hybridizing, especially by its transcript, to a molecular probe, i.e., to a nucleic acid based probe, e.g., a DNA based probe, including for example a probe of the beacon type as explained herein. Preferably a barcode of the invention comprises more than 2 or more than 3 recognition binding sites and/or more preferably more than 2 barcode units or more than 3 barcode units, wherein each unit comprises or consists of multiple repeats of one or several (for example 3 or more) recognition binding sites.

In a particular embodiment of the invention, the probe is a beacon and the barcode is a beacon barcode with beacon binding site(s).

In an embodiment where several recognition binding sites or several barcode units are present into a barcode, at least some of said binding sites or barcode units are separated by a spacer.

Accordingly, the recognition binding sites and/or the barcode units may be separated by intervening nucleotides or nucleotide sequences of 1 to 250, especially 1, 2, 3, 4, 5, 6, 7, 8 nucleotides.

The barcode and/or the barcode units of the invention may additionally be preceded or followed or framed by one or more restriction sites which are located at its 5'- and/or 3'-ends. Apart from these different types of sequences, in a particular embodiment, the barcode may be devoid of further functional sequences involved in transcription including sequences eliciting or subject to transcription.

In a particular embodiment of the invention, the polynucleotide comprises several barcodes which are separated from each other at least by a functional promoter construct. Accordingly, each barcode is placed under the control of a particular transcriptional promoter as defined herein.

In a particular embodiment of the invention, each barcode and/or each barcode unit comprises tandem repeats of at least one sequence suitable to allow hybridization of its transcript with the probe sequence when contacted with said probe in appropriate conditions.

In a particular embodiment, each barcode and/or each barcode unit comprises repeats of two different recognition binding sites or repeats of more than two recognition binding sites, especially 3 or more, each recognition binding site being suitable when transcribed, to hybridize with a specific probe sequence.

In a particular embodiment of the invention, the barcode and/or the barcode unit comprises tandem repeats of at least two, especially 3, 4, 5 or more different sequences which, when transcribed, are suitable for hybridization with different probe sequences when contacted with said probes in appropriate conditions.

The invention especially relates to the beacon binding sites illustrated by their nucleotide sequences in FIG. 6 and designated as AB, BC, or AC, or to repeats of these binding sites whether used as AB repeat, BC repeat, AC repeat, or AB inverse, AC inverse or BC inverse when inserted in the other orientation in the core vector. The invention also relates to the A, B and C binding sites derivable from the sequences of FIG. 6.

In another embodiment of the invention, the sequences of the recognition binding sites of one barcode or of one barcode unit are identical but are appropriate, when transcribed, to hybridize with different specific probes wherein the difference between the various probes results in a different measurable change of the recognized and hybridized polynucleotide giving rise to a different signal molecule such as different fluorescence moieties or light emitting compounds.

Identification of appropriate nucleotide fragments suitable to constitute recognition binding sites is context dependant with respect to the assay to be carried out according to the invention. In another embodiment such nucleotide fragments may be standardized.

In a particular embodiment, the sequences used to prepare the recognition binding sites are not found in the transcriptome of the cell in which the polynucleotide is introduced, and especially are not found in the mammalian transcriptomes, especially in the human transcriptome as represented in available databases at the time of screening. Especially, the sequences used to prepare the recognition binding sites are derived from non-mammal organisms. A particular example of such organism is *Drosophila* which provides a source for the identification of appropriate sequences.

A preliminary selection of sequences may be made having recourse to available algorithms, such as "mfold" providing data on sequences which are deemed to harbour accessible binding sites when comprised in RNA sequences. The secondary structure of the mRNA is accordingly determined by identifying potential hybridization sites that are accessible to binding by nucleic acid hybridization probes. There is a large body of evidence suggesting that heteroduplex formation is primarily constrained by local secondary structure and folding of RNA. The composition and length of the nucleic acid probes appears to be of less importance. Candidate probes identified by algorithm are then tested in vitro for their ability to bind an in vitro transcribed mRNA. Those able to best form heteroduplexes are retained and used as nucleic acid probes.

Another solution to address this question of designing probes has focused on the selection of nucleic acid probes by empirical approaches, using oligonucleotide scanning arrays, for example. Using such arrays has reinforced the strength of empirical approaches over prediction algorithms.

Comparisons between empirical methods to determine regions accessible to hybridization, versus those theoretically determined by the prediction algorithm, have consistently highlighted the superior strength of empirical approaches. In fact the most appropriate oligonucleotides (selected for hybridization to single stranded regions) do not correspond to the positions predicted as loops by the algorithm. Moreover it is far from clear that the single stranded regions predicted by prediction algorithms are indeed more accessible to heteroduplex formation, than stem-loops.

The following description for preparation of molecular beacon is adapted from Bratu D. (Molecular beacons: Fluorescent probes for detection of endogenous mRNAs in living cells. *Methods Mol Biol* 319, 1-14 (2006)). Theoretically, any sequence within a target RNA can be chosen as a site for molecular beacon binding. The endless possibilities give one the confidence that such regions are easily identified. However, the extent of target accessibility is primarily a consequence of complex secondary and tertiary intramolecular structures, which are difficult to predict and which can mask many of these regions. Furthermore, inside the cell, mRNAs exist in association with proteins that further occlude parts of the mRNA. Although regions involved in protein binding can only be identified by experimental analysis, reasonable attempts can be made to predict the regions that are not involved in tight secondary structures. So far, several in vitro assays and theoretical algorithms are available to help identify putative target sites within mRNA sequences, as well as probes with high affinity for binding (Tyagi, S. & Kramer, F. R. Molecular beacons: probes that fluoresce upon hybridization. *Nat Biotechnol* 14, 303-308 (1996); Mir, K. U. & Southern, E. M. Determining the influence of structure on hybridization using oligonucleotide arrays. *Nat Biotechnol* 17, 788-792 (1999); Matsuo, T. (1998). In situ visualization of messenger RNA for basic fibroblast growth factor in living cells. *Biochim Biophys Acta* 1379, 178-84; Sokol, D. L., Zhang, X., Lu, P. & Gewirtz, A. M. (1998). Real time detection of DNA.RNA hybridization in living cells. *Proc Natl Acad Sci USA* 95, 11538-43). The mfold RNA folding algorithm is used to predict the most thermodynamically stable secondary structure along with an ensemble of suboptimal structures (Southern, E. M., Milner, N. & Mir, K. U. (1997). Discovering antisense reagents by hybridization of RNA to oligonucleotide arrays. *Ciba Found Symp* 209, 38-44; discussion 44-6; Ho, S. P., Bao, Y., Lesher, T., Malhotra, R., Ma, L. Y., Fluharty, S. J. & Sakai, R. R. (1998). Mapping of RNA accessible sites for antisense experiments with oligonucleotide libraries. *Nat Biotechnol* 16, 59-63). Since none of these structures can be considered to represent the naturally occurring conformation, the parameters that describe the entire ensemble are analyzed. The number of candidate sites is winnowed down by employing a second algorithm. OligoWalk scans the folded RNA sequence for regions to which various length oligonucleotides are capable of binding. With consideration of the base composition of each oligonucleotide, and of the predicted secondary structure of the RNA, the output provides information about the stability of the expected hybrid, and thus identifies potential target regions. Once identified, molecular beacons specific for those regions are designed and synthesized and tested empirically with in vitro synthesized RNA in a spectrofluorometer.

Particular polynucleotides or barcode units of the polynucleotide of the invention comprise one of the following binding sites, especially suitable for recognition by beacon probes:

```
                                          (SEQ ID NO: 1)
5'-TTCTCTTCAAACTTTTCCGCTTTT-3',
or (SEQ ID NO: 2)
5'-CGCCAAAACCTATTATCTTAAGTC-3';
or
```

```
                                                (SEQ ID NO: 3)
5'-CTCACCTGCTCTTCTCAGACC-3'
as binding site 1
and (SEQ ID NO: 4)
5'-GCTATAGCACTAAGGTAAGACCC-3'
as second binding site.
```

These sequences are derived from *Drosophila* and are not present in the genome of mammals.

In a particular embodiment of the invention, these nucleotide fragments are used together in one barcode unit. Said barcode unit may contain further recognition binding site(s) and may be repeated in the barcode.

In a particular polynucleotide, each tandem repeat sequence of the barcode is framed by one or several restriction sites.

Generally, the length of the double-stranded polynucleotide of the invention is determined by the length of the barcode(s) and the length and number of promoter sequences and of the optional additional sequences (including cloning sites or part of restriction sites) and is thus adapted to the need of the intended applications. The general length of the polynucleotide construct of the invention may be adapted to the requirement that said polynucleotide stably integrates in a particular host cell, especially in the genome of said host cell.

To illustrate, the polynucleotide of the invention may be such that the barcode unit or each barcode unit has a length in a range of 16 to 200 nucleotides.

Also, for illustration purposes, the overall length of the polynucleotide of the invention may be comprised in a range of 80 to 30 000 nucleotides.

For illustration purpose, the following is a disclosure of global structures that may be found in polynucleotides of the invention: polynucleotides may comprise or contain, when read from 5' to 3' end:
- a promoter followed by a barcode;
- a promoter followed by the coding sequence including intron(s) of the gene providing said promoter or followed by part or all of the introns, followed by a barcode;
- an entire gene of interest or a part of said gene including its promoter followed by a barcode;
- a promoter followed by a cDNA of the gene of interest providing the promoter followed by a barcode.

These various constructs may further comprise, after the promoter or at the end of the construct, a reporter molecule especially a reporter DNA. They may also comprise additional sequences such as restriction sites, 3' transcription termination sequences, poly A tail, microRNA or non coding RNA as disclosed herein when considering the polynucleotide of the invention.

It is emphasized that all the definitions which are provided herein in relation to barcode, barcode units, and recognition sites in the polynucleotide, applies in particular to beacon binding sites, barcode units and beacon barcodes i.e., constructs that are suitable for recognition by beacon probes.

In a specific embodiment of the invention, the polynucleotide further comprises, downstream of the promoter sequence and upstream or downstream of the barcode sequence, a DNA coding for a marker protein, wherein said coding DNA is placed under the control of expression regulatory elements, including under the control of said promoter controlling transcription of the barcode.

The presence of a coding sequence for a reporter or marker protein may add some level of determination of the functionality of the promoter of the polynucleotide and especially may enable the detection of the expression capacity of the polynucleotide construct of the invention. The marker protein may be any type of known marker used for expression study in a cell, such as the Green Fluorescent Protein (GFP), luciferase or chloramphenicol acethyltranferase (CAT), and preferably marker proteins which have no endogenous expression activity.

The polynucleotide of the invention may further comprise a coding sequence of a gene of interest either in a version containing introns or as a cDNA, and/or the DNA coding for a reporter or marker protein, under the control of said promoter for transcription of the barcode.

As stated above, the gene of interest providing the promoter of the polynucleotide of the invention encompasses genes involved in the homeostasis of cells, and especially genes of interest in the design of a therapeutic strategy or genes involved in the maintenance of the cell structure or in the regulation of the cell metabolism, including genes involved in the pathological conditions in a host, or activated as a result of such a condition, especially in a human host. The gene of interest may especially be any native mammalian gene, especially a native human gene, whose expression profile or regulation in a cell has to be studied and especially whose transcription should be studied. The gene of interest may also be a mutated version of a native gene, especially of a native mammalian, in particular human gene, whose presence and interest for cellular gene expression profiling and especially for such profiling at the transcript level should be investigated. The gene of interest may also be a gene whose expression is induced or regulated in a host cell, especially a mammal cell or a human cell, as a result of a pathogen infection of the mammal or human host. The gene of interest may especially be a gene regulated by or regulating immunological reactions in a host.

For illustration, a gene of interest may be one involved in the immune response, in particular in the innate immune response, such as interleukins including IL10 or IL8, or cell adhesion molecules like ICAM or genes such as TgF-β, C-fos or CCL20.

Particular genes of interest may be genes which are deregulated in a host, or which are induced in a host, especially a mammalian, in particular a human host, when said host is affected by a pathological condition, including for example pathologies leading to uncontrolled cell proliferation, especially cancer, or pathologies accompanied with deregulation of the immune system of the host.

According to a particular embodiment, a gene of interest may be selected among genes which are sensitive to drugs or to other external stress factors (including pathogen organisms or agents) in a studied cell.

According to a particular embodiment, the gene of interest may represent a candidate compound or target for a therapeutic treatment, whose expression profiling, either on or off and especially transcription profiling has to be determined after administration of this drug or stress factor.

In a particular embodiment, gene profiling may involve screening compounds libraries to determine the interaction of the compounds with the genes of the cell. The invention thus relates to the use of the polynucleotide of the invention to monitor gene profiling in a cell, by screening a library such as a DNA library, a RNAi library, a chemical library, a library of pathogens.

Gene profiling according to the invention encompasses monitoring of gene expression, through the observation of the transcription of the polynucleotide of the invention comprising the promoter of the gene, including for determining the conditions to activate or elicit gene transcription (profiling on) or to inactivate gene or silence transcription (profiling off). It also relates to modulation of gene expression either to upregulate or to downregulate expression from a starting level of tanscription. This may be studied at the level of one or several genes in a cell.

The invention also relates to the polynucleotide as defined in the present application when cloned into a vector that enables propagation inside the cell to be monitored and possibly enables the stable insertion of said polynucleotide into the genome of the cell.

Alternatively, the polynucleotide may remain as an episome in the cell.

Particular vectors, suitable for performing the invention are especially plasmids, cosmids, viruses or bacs (bacterial artificial chromosome).

The invention also relates to a set of different polynucleotides of the invention.

The invention also relates to a cell especially a living cell and in particular an individual cell or a cell line comprising, especially stably integrating (i.e., integrated in the cell genome) the polynucleotide of the invention. The cell may be a primary cell or a cell line.

A particular cell or cell line is made of eukaryotic cell(s) or prokaryotic cells. Especially, it is a mammalian cell or cell line especially a human cell or cell line. Alternatively, the cells are from a rodent, especially a mouse or another appropriate model animal, or from a zebra fish or from *Drosophila*.

In a particular aspect of the invention, the mammalian cell or mammalian cell line is a non-human mammalian cell or cell line.

In a particular embodiment, the cell is a differentiated cell or the cell line is derived from differentiated cells.

In another embodiment cells are de-differentiated cells. Particular de-differentiated cells are cells that have escaped proliferation control in vivo.

In another embodiment the cell or the cell line is derived from pluripotent cells or from stem cells, especially human pluripotent cells or stem cells, either embryonic or adult pluripotent or stem cells.

Particular examples of cells that may be used to perform the invention encompass cells involved in the immune system such as macrophages, dendritic cells, monocytes or epithelial cells. Other cells are cancer cells such as cells developing in breast cancer.

Cells to perform the invention may be non-polar cells such as non-polar HeLa cells, or may be polarized cells. Examples of cells used to derive cell lines include CaCo2 cells (of heterogenous human epithelial colorectal adenocarcinoma cells), U937 cells (established from a diffuse histiocytic lymphoma and displaying monocytic characteristics) or THP-1 cells (derived from monocytic leukemia).

It has been shown that the introduction and especially the integration in the genome, of a polynucleotide of the invention provided in a cell, may be achieved through different ways, including by injection in a cell or preferably by transfection of the cell with said polynucleotide. A description of a transfection protocol is given in the example provided below and which can be applied to various cells and various polynucleotides of the invention.

The invention also concerns a cell or cell line as defined above and illustrated in the examples, which further comprises one or several molecular detection probes as defined in the present application. As for the polynucleotide of the invention, said molecular probe(s) is (are) introduced in the cell by injection or preferably by transfection.

The invention also relates to a set of cells or to a set of cell lines, wherein each set of cells or cell lines comprises especially integrated therein, one or several polynucleotide(s) as defined herein, each cell or cell line having a composition in said polynucleotide(s) which is different from that of the other cell(s) or cell line(s).

As disclosed herewith, the monitoring of gene expression in a cell, which has been modified by insertion of the polynucleotide of the invention requires means to detect the transcription of said polynucleotide. The detection may be performed by using probes (molecular probes) that are able to detect measurable changes at the level of transcripts. Measurable changes may be changes in the conformation of the nucleic acid as a result of probe hybridization or changes in light emission (such as fluorescence) as a result of probe hybridization.

Suitable probes to detect expression of the polynucleotide of the invention may be linear probes, or non linear probes such as beacon probes. They are nucleic acid based probes, especially DNA base probes.

In a particular embodiment, the invention thus concerns a molecular beacon and its use as a probe to detect transcription of the polynucleotide of the invention. Molecular beacons are DNA based molecules suitable for hybridizing with their complementary sequences in the sequences transcribed from beacon binding site(s) of the beacon barcode(s) in the polynucleotides of the invention, said molecular beacon(s) having a stem-and-loop polynucleotide structure and being suitable for visualisation when hybridized to their target sequence, especially in a reversible manner.

A particular molecular beacon is defined as a stem-and-loop polynucleotide structure wherein the loop portion of the polynucleotide is the probe sequence suitable to hybridize specifically to a beacon binding site of the polynucleotide and the stem portion consists of two arms formed of sequences complementary to each other, each of the arm sequence harbouring, attached to its free extremity which is adverse to the loop portion of the polynucleotide, either a fluorescent moiety or a non-fluorescent quenching moiety wherein said moieties, when attached to said arm sequences, are sufficiently close to each other to cause the fluorescence of the fluorescent moiety to be quenched by fluorescence resonance energy transfer, and further said loop portion of the polynucleotide is at least twice longer in nucleotides than each arm polynucleotide structure.

According to their definition, the molecular beacons defined herewith have a probe sequence which is complementary to beacon binding site(s) of a beacon barcode of the polynucleotide or especially to its transcript.

The expression "complementary" means that the molecular beacon is suitable to hybridize in defined hybridization conditions, especially in physiological conditions, by base pairing with the complementary sequence of a molecular beacon binding site. In the context of gene profiling in a cell according to the invention, hybridization of the beacon probe is achieved with the transcript of the polynucleotide of the invention, at the level of the beacon binding sites.

Preferably, the probe sequence of the molecular beacon is perfectly complementary to the targeted molecular beacon binding sites or its transcript in a cell, and thereby is suitable to form a stable hybrid with said transcript in a cell so that their hybridization allows a measurable change, e.g., a conformational change, to occur in the molecular beacon, thereby enabling them to raise a signal, especially to emit light and especially to fluoresce.

As known in the art, fluorescence of molecular beacon results from the ability of the fluorophore (fluorescent moiety) and quencher (non-fluorescent quenching moiety) to move away from each other, as a result of hybridization, thereby allowing fluorescence.

The design rules for preparation of molecular beacons are well-known from the skilled person. Such beacon probes are illustrated in the examples.

In a particular embodiment, the molecular beacons are such that the fluorescent moiety and non-fluorescent quenching moiety are covalently linked to the arm sequences of the stem-and-loop polynucleotide structure.

In a particular molecular beacon of the invention, the polynucleotide structure of the beacon probe has from 8 to 100 nucleotides.

Many different fluorescent moieties may be used in order to prepare molecular beacons of the invention in association with a quenching moiety for illustration. The following examples are provided. According to particular embodiments, the fluorescent moiety (fluorophore) is selected in the group of Quantum Dots and derivatives, Alexafluor family of dyes, FAM, TET or CAL FluorGold 540, HEX or JOE, VIC$^B$, CAL Fluor Orange 560$^A$; Cy3$^C$ or NED$^B$, Quasar 570$^A$, Oyster 556$^D$; TMR or CAL Fluor Red 590$^A$; ROX or LC red 610$^E$, CAL FLuor Red 610$^A$; Texas red or LC red 610$^E$, CAL Fluor Red 610$^A$; LC red 640$^E$ or CAL Fluor Red 635$^A$; Cy5$^C$ or LC red 670$^E$, Quasar 670$^A$, Oyster 645$^D$; LC red 705$^E$ or Cy5.5$^C$ or 5-(2'-aminoethyl)aminonaphthalene-1-sulfonic acid (EDANS), fluorescein, anthranilamide, coumarin, and terbium chelates, and the quenching moiety (quencher) is selected in the group of DDQ-I$^A$ (absorption max 430 μm), Dabcyl (absorption max 475), Eclipse$^B$ (absorption max 530), Iowa Black FQ$^C$ (absorption max 532), BHQ-1$^D$ (absorption max 534), QSY-7$^E$ (absorption max 571), BHQ-2$^D$ (absorption max 580), DDQ-II$^A$ (absorption max 630), Iowa Black RQ$^C$ (absorption max 645), QSY-21$^E$ (absorption max 660), BHQ-3$^D$ (absorption max 670), Gold, Rare Earth Metals or 4-(4'-dimethylaminophenylazo)benzoic acid (DABCYL), rhodamin, pyrenebutyrate, eosine, nitrotyrosine, ethidium and tetramethylrhodamine.

Particular pairs of fluorophore/quencher are those resulting from the above lists by association of the respective fluorophore/Quencher marked by the same capital letter (A, B, C, D or E) or other pairs selected in the group of the following combinations: CY5 with BlackHole Quencher 3, CY3 with BlackHole Quencher 2,5-(2'-aminoethyl)aminonaphthalene-1-sulfonic acid (EDANS) with 4-(4'-dimethylaminophenylazo)benzoic acid (DABCYL), fluorescein with rhodamin, fluorescein with pyrenebutyrate, fluorescein with eosine, anthranilamide with nitrotyrosine, coumarin with ethidium, and terbium chelates with tetramethylrhodamine.

Alternative probes are other nucleic acid based probes. These probes upon hybridization to the recognition site elicit a measurable change such that it can be measured by differing instruments. Examples are linear nucleic acid probes, strand displacement probes, scorpion probes, adjacent probes, cyclicon probes, HyBeacons, minor groove binder probes, molecular beacon probes (including wavelength shifting molecular beacon probes), 5' nuclease probes, and amplifluor probes.

Adjacent probes such as described in Wittwer, C. T., Herrmann, M. G., Moss, A. A. & Rasmussen, R. P. Continuous fluorescence monitoring of rapid cycle DNA amplification. *Biotechniques* 22, 130-131, 134-138 (1997) are suitable for the detection of the transcripts of the polynucleotides according to the invention. These probes utilize two single-stranded hybridization probes that bind to neighboring sites on a target nucleic acid. One probe can be labeled with a donor fluorophore and the other with an acceptor. The distance between the two probes once hybridized is chosen such that efficient fluorescent energy transfer can occur from donor to acceptor. Energy transfer should be minimal when probes are not hybridized to their target. Besides changes in fluorescence signal, other measurable changes can be used to indicate hybridization by adjacent probes to neighboring sites. Thus these probes are not only FRET based probes.

Strand displacement probes, including scorpion probes disclosed in Solinas, A. et al. Duplex Scorpion primers in SNP analysis and FRET applications. *Nucleic Acids Res* 29, E96 (2001) are further probes suitable to perform the detection of the polynucleotide of the invention. These probes utilize two complementary oligonucleotide probes, one probe labeled with a fluorophore and the other labeled with a non-fluorescent quencher moiety. When the two probes are hybridized to each other the fluorophore and quencher are in close proximity resulting in contact quenching occurring and low fluorescence emission. In the presence of a target nucleic acid one of the probes forms a more stable probe target hybrid resulting in the two probes being separated. As a consequence of this displacement, fluorophore and quencher are no longer in close proximity and fluorescence increases. Besides changes in fluorescence signal, other measurable changes can be used to indicate changes in strand displacement. Therefore these probes are not only fluorophore-quencher based.

It is possible to use multiple distinct nucleic acid recognition binding barcodes, wherein each of them is fused to one specific endogenous promoter sequence, to provide multiple polynucleotide constructs for use in a single cell simultaneously. In this case, the detection probes can be designed with molecules yielding distinguishable signals. Therefore, this allows the profiling of multiple genes in single cells in real time. For example, this is possible via the usage of multicolored beacons, that is different beacons with different colors, that hybridize specifically to the various nucleic acid binding sites.

In a particular embodiment, the polynucleotides of the invention are designed in such a way that, when their transcript hybridize with a detection probe and especially with the molecular beacons, they provide a gene expression profile that enables visualisation of more than 1, especially up to 4, or more especially up to 6, and if appropriate up to 15, 20 or up to 32 transcripts of the polynucleotides of the invention. This may be achieved by combining in a barcode, a set of beacon binding sites, which, when hybridized, provide a spectrum with a combination of colours that may be decomposed to provide a fingerprint of the transcript of the polynucleotide.

For illustration purpose, when different colours of fluorophores are available, they may be used in combination to elicit a spectrum having more than one colour. If such spectra can be decomposed in their various components when visualized, it provides possibilities to enable visualisation of more transcripts than the number corresponding to the available basic colours of the fluorophores. In order to achieve such spectrum with combinations of colours, the beacon barcode that should give rise to the multicolour spectrum should comprise beacon binding sites complementary to beacons having fluorophores of different colours.

As illustrated in the figures, combinations of fluorescent colors of the probes bound to each barcode unit can be used to profile multiple genes in a single cell.

Especially, when a barcode unit comprises 2 recognition binding sites, each of which being labelled with a different tag, especially a different colour, it is possible, having recourse to six different tags such as colours or fluorescent moieties, to profile up to 15 genes in a single cell.

When a barcode unit comprises 3 recognition binding sites, each of which being labelled with a different tag, it is possible, having recourse to six different tags such as colours or fluorescent moieties, to profile up to 20 genes in a single cell.

The thus defined detection probes are complementary to the sequence of the transcript that is transcribed from the barcode or to a part thereof sufficient to characterize said transcript. In a particular embodiment, the complementarity is such that the two sequences perfectly basepair.

In a particular embodiment of the invention, the detection probe is a molecular beacon and its loop portion has from 10 to 55 nucleotides and each arm polynucleotide structure has from 4 to 16 nucleotides.

Particular molecular beacons suitable to perform the invention have one of the following nucleotide sequence:

```
                                           (SEQ ID NO: 5)
    5'-GCUGC AAAAGCGGAAAAGUUUGAAGAGAA GCAGC-3'

(SEQ ID NO: 6)
    5'-CGACC GACUUAAGAUAAUAGGUUUUGGCG GGUCG-3'
```

The invention also provides a kit comprising (i) a polynucleotide as defined herein and (ii) cells or cell line suitable for integration of said polynucleotide and/or one or more molecular detection probes.

In a particular embodiment, the kit comprises a polynucleotide as described in the present application and a cell or a cell line suitable for integration of said polynucleotide or a set of said polynucleotides and a set of said cells or cell lines.

According to another embodiment, the kit alternatively or further comprises cell lines with barcode polynucleotide stably integrated downstream of the gene or promoter of interest.

In a particular embodiment the kit further comprises one or several molecular detection probe(s) suitable for hybridizing with the recognition binding site(s) of the barcode(s).

The invention also relates to a kit which comprises a polynucleotide as described in the present application and one or several molecular detection probe(s) suitable for hybridizing with the recognition binding site(s) or the barcode(s) or its transcript.

In a particular embodiment, the kit comprises a polynucleotide as described in the present application and one or several molecular detection probe(s) suitable for hybridizing with the recognition binding site(s) of the barcode(s), or to its transcript, a cell or a cell line suitable for integration of said polynucleotide or a set of said polynucleotides and a set of said cells or cell lines.

In a particular embodiment of the invention, the kit herein described comprises molecular beacons having the following nucleotide sequences.

```
                                           (SEQ ID NO: 5)
    5'-GCUGC AAAAGCGGAAAAGUUUGAAGAGAA GCAGC-3'
    or
                                           (SEQ ID NO: 6)
    5'-CGACC GACUUAAGAUAAUAGGUUUUGGCG GGUCG-3'.
```

The molecular detection probes are designed in such a way that the visualisation of their hybridization with their target is obtained as a result of a measurable change, such as a fluorescence which is switched on, when the molecular detection probe binds to its target sequence.

Optionally, the kit defined further comprises a plasmid with a barcode polynucleotide cloned downstream of the gene or promoter of interest, and/or probes (for example molecular beacons) able to recognize the barcode polynucleotide, and/or reagents (peptides, lipids, chemicals etc.) able to introduce probes and plasmids into cell lines especially by transfection or microinject them into the cell and/or positive and negative controls for each step in experimental procedure as required.

The invention is also directed to a process of studying gene transcription in a cell or in a cell line comprising the steps of:
(i) providing a cell or a cell line comprising, especially stably integrating a polynucleotide as defined in the invention,
(ii) eliciting, silencing or modulating transcription of the polynucleotide construct,
(iii) detecting a measurable change in the transcription of the polynucleotide.

The step of detecting the measurable change in the transcription of the polynucleotide may comprise:
contacting the cell or cell line wherein the polynucleotide has been introduced, with one or more detection probe(s) as defined herein;
detecting the hybridization between said detection probe(s) and the transcript of the recognition binding site(s) of the barcode, as a reporter of the transcription activity of the promoter of the polynucleotide construct.

The study of gene transcription enabled by the process of the invention is achieved as a result of promoter activation in the polynucleotide which gives rise to transcription of the molecular barcode, thereby allowing the production of multiple copies of said molecular barcode that leads to their binding to their specific complementary molecular detection probes.

Step (ii) of the process may be carried out by bringing the cell or cell line into contact with a molecule or agent of interest, whose impact on the transcription is studied.

Integration processes especially for stable integration of the polynucleotide of the invention into the cells are well known for the skilled person and generally encompass injection or transfection protocols. Such protocols are illustrated in the Examples having recourse to HeLa cells and particular polynucleotides. Similar techniques can be repeated for different cells and polynucleotides.

Similarly, contacting the cells with detection probes may be achieved by methods as those illustrated in the examples.

When a gene of interest and/or a sequence encoding a marker protein is also present in the polynucleotide of the invention, the transcription activity of the promoter also enables the transcription and expression of said gene and/or marker protein.

Thereby, the promoter activity may be detected at the level of transcription, resulting in measurable change, especially fluorescence or other light-emitting signal of the detection probe, and possibly at the level of expression of the product of the gene of interest and/or of the marker protein.

Any appropriate means for detection of the measurable changes, especially of the fluorescence, may be used in order to monitor the transcription activity of the promoter of the polynucleotide of the invention. Especially, high-content microscopy and live cell imaging techniques are suitable to carry out the detection.

One particular advantage of the invention, is that the process which is described enables study of gene transcription reflected by transcription of the polynucleotides comprising the promoters of said genes at the level of a single, living cell.

The process of the invention is especially adapted for polynucleotide transcription study in a real-time assay, or at an end point.

Another advantage of the process of the invention is that it can be carried out to study gene transcription on a single gene basis, especially on a single cell, or to study gene transcription on a multiple genes basis, especially in a single cell. It has been shown that transcription of multiple genes reflected by transcription of the polynucleotides comprising their promoters, can be studied for up to 35 genes in a single cell, and especially 2, 3, 4, 5, 6 genes can be studied in a single assay.

According to a particular embodiment of the invention, the step of eliciting, silencing or modulating the transcription of the polynucleotide is obtained after contacting the cell or cell line with an external factor.

Such an external factor may be a library of chemical compounds, interfering small RNAs or a library of organisms which is screened on the cell or cell line.

It is also especially appropriate and intended for quantitative detection of polynucleotide transcription, through quantitative detection of the binding events of the detection probes with their target sequences as a result of the transcription of the polynucleotides of the invention.

In a particular embodiment, the process of the invention further comprises the detection of an expressed reporter protein encoded by the polynucleotide construct and expressed under the control of the promoter contained in the polynucleotide construct.

Particular promoter constructs contained in the polynucleotide sequence of the invention, and whose activity is detected through the process of the invention are the promoters of genes that have been disclosed herein.

When the process of the invention is performed in order to assay the transcription activity of the IL8 promoter, said activity is elicited by infection of the cell or cell line with bacteria for example with strain *S. flexneri*.

In a particular embodiment of the process of the invention, the polynucleotide further expresses a reporter gene selected in the group of GFP, luciferase, SYBR green.

In another particular embodiment of the invention, the polynucleotide expresses one or many nucleotide sequence(s) providing antibiotic resistance(s). Examples of the antibiotic resistance genes are given in the examples and illustrated in FIG. 6.

Various applications of the process, kit, or polynucleotide of the invention are contemplated within the scope of the invention. According to an embodiment of the invention, they may be used for screening libraries, including RNAi libraries, DNA libraries, chemical libraries or libraries of pathogen organisms.

According to an embodiment of the invention, they may be used in a diagnosis process, especially as a part of said diagnosis, in order to detect a disease state, or especially an infection state such as a viral or bacterial infection in a host, in particular in a human host.

It may also be used to monitor immunological reactions at a cellular basis. This may involved assaying the transcription of a polynucleotide of the invention when the assayed cell is contacted with the compounds of a library to screen (including chemical library, RNAi library, DNA library or library of pathogens). The outcome of the assay is advantageously detected using high-content and high throughput microscopy.

Another application of the invention is the follow up of the outcome of a therapeutic treatment on a cellular basis.

The invention may especially be used in screening process of potential therapeutic compounds or therapeutic targets and especially in screening process of compounds, possibly interacting with the immune system.

Another application of the invention is for investigating cellular targets of a compound or of a pathogen organism or agent.

The invention also concerns monitoring the interactions between a pathogen and a host, at the level of a cell of the host or of a cell derived from said cells, especially when said cell is placed in conditions of being infected with said pathogen.

The invention is also directed to a transgenic non-human mammal that expresses in the genome of some or all of its cells, a polynucleotide construct of the invention, or cells transformed and especially transfected with said polynucleotide of the invention.

Further characteristics of the invention and properties will be made apparent from the examples and figures which follow: it is especially mentioned that the features disclosed in the examples and figures may be applied in a more general way to perform the invention and accordingly except wherever stated, are not limited to the particular products illustrated in the examples.

DESCRIPTION OF FIGURES

FIG. 1A shows the principle of molecular beacons.

FIG. 5A(1) and FIG. 5A(2): Dual color coding scheme. The different dots correspond to different colors of the fluorophores.

FIG. 5B: Triplex color coding scheme; one Beacon Barcode unit consists of 3 sequences Type I, Type II & Type III.

FIG. 6A-FIG. 6F: Nucleotide sequences of the inserts used for the preparation of core vectors.

FIG. 1. A. Principle of molecular beacons. Molecular beacons are internally quenched hairpin shaped oligonucleotides probes that become fluorescent upon hybridization with their target sequence such as RNA or DNA.

Figure 1B:
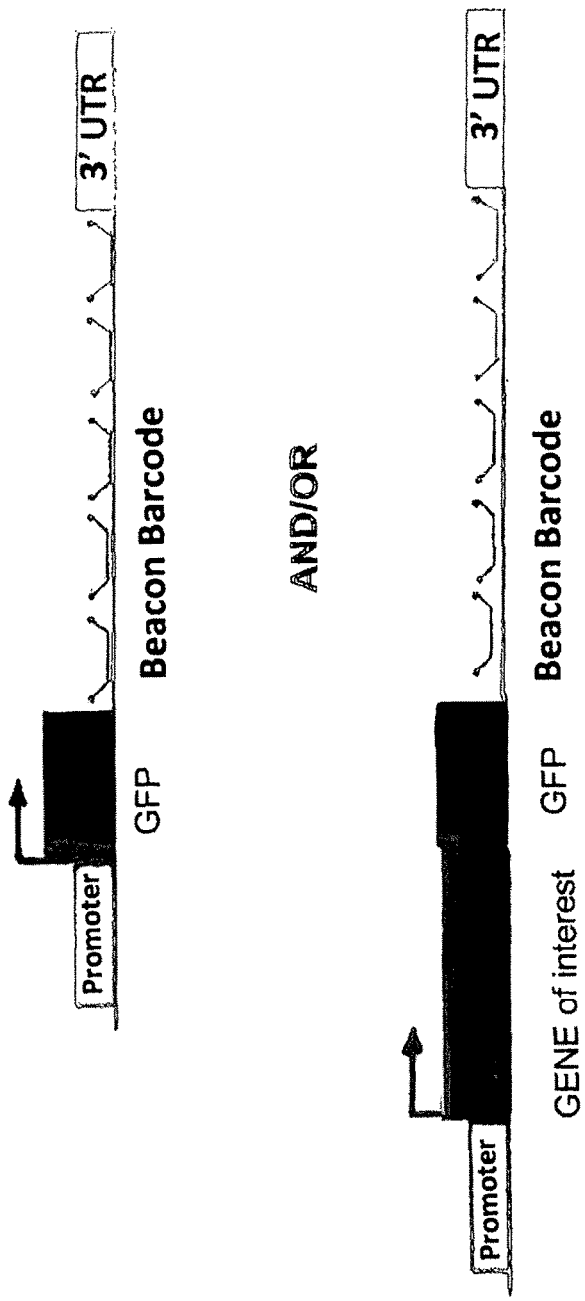
FIG. 1B shows the principle of molecular beacon barcode nucleotides.
Figure 1C:
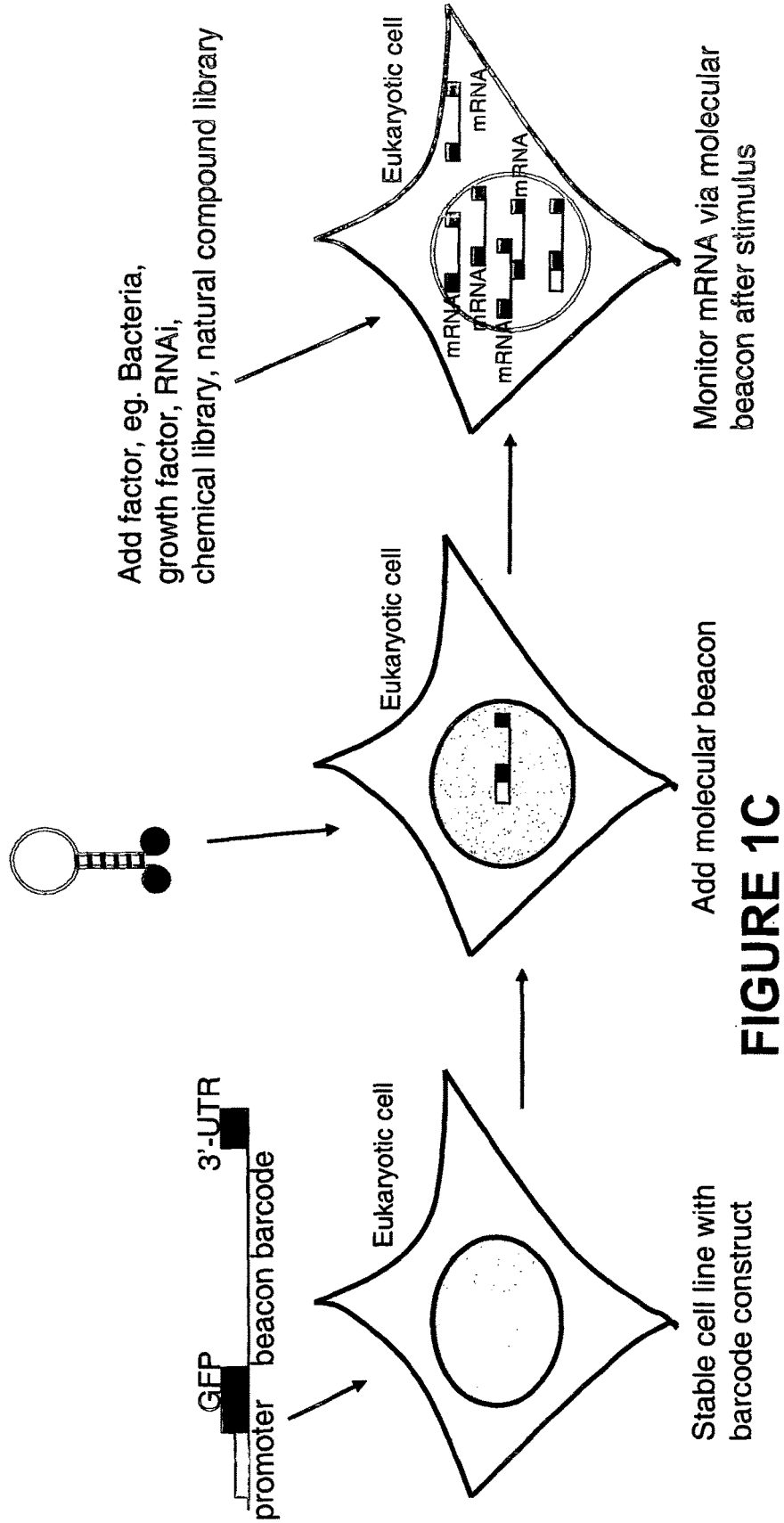
FIG. 1C shows the principle of live cell based assays using molecular beacons and beacon barcoded constructs.
Figure 2A:
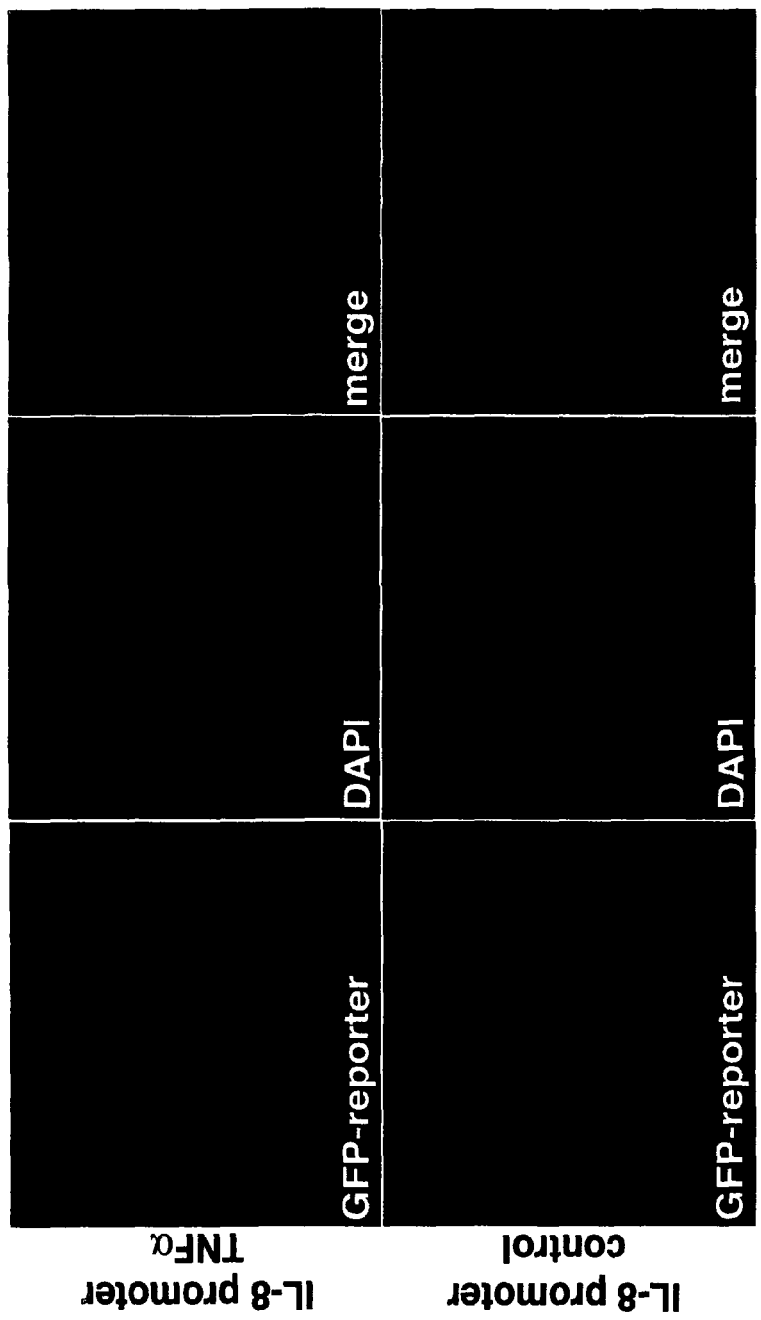
FIG. 2A: transcriptional response of the cell line IL8WT stimulated with TNFα.
Figure 2B:
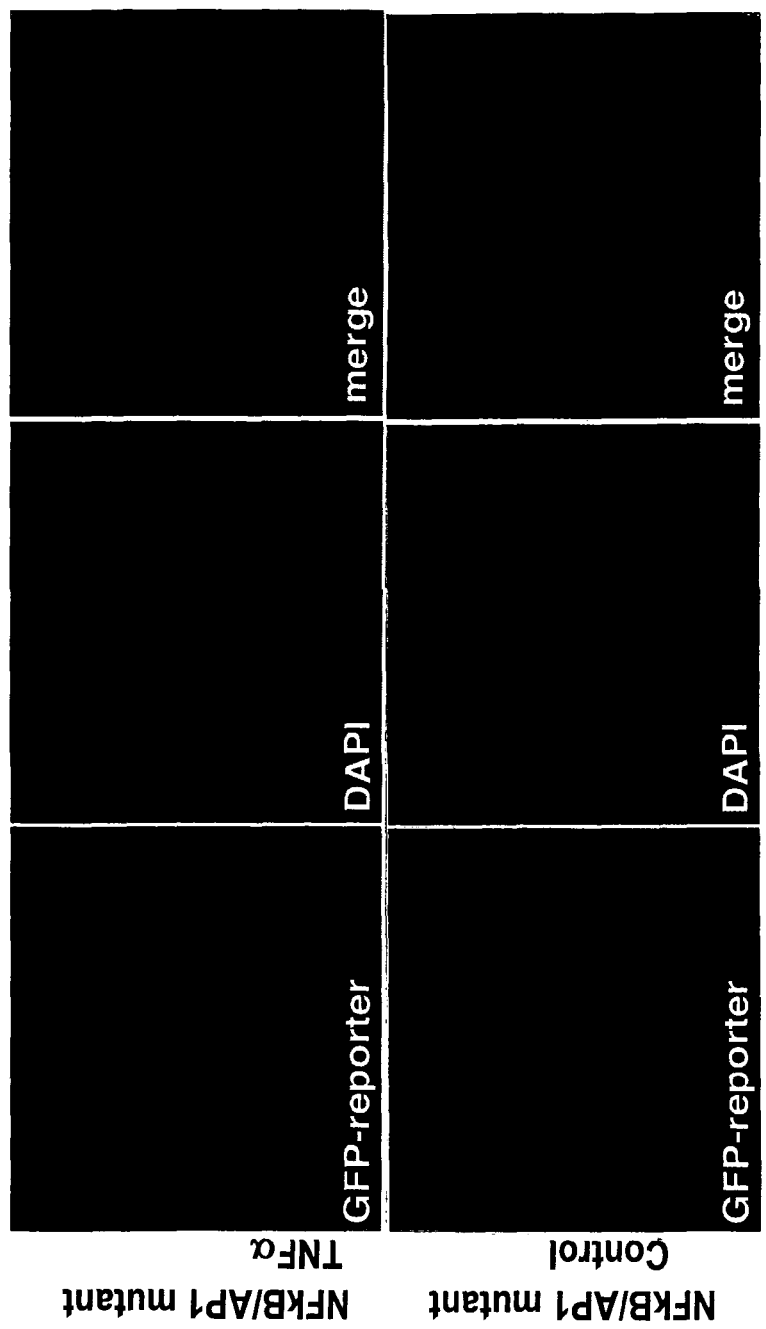
FIG. 2B: transcriptional response of the cell line IL8Mut (NFKB/AP1 mutant) stimulated with TNFα.
Figure 3:
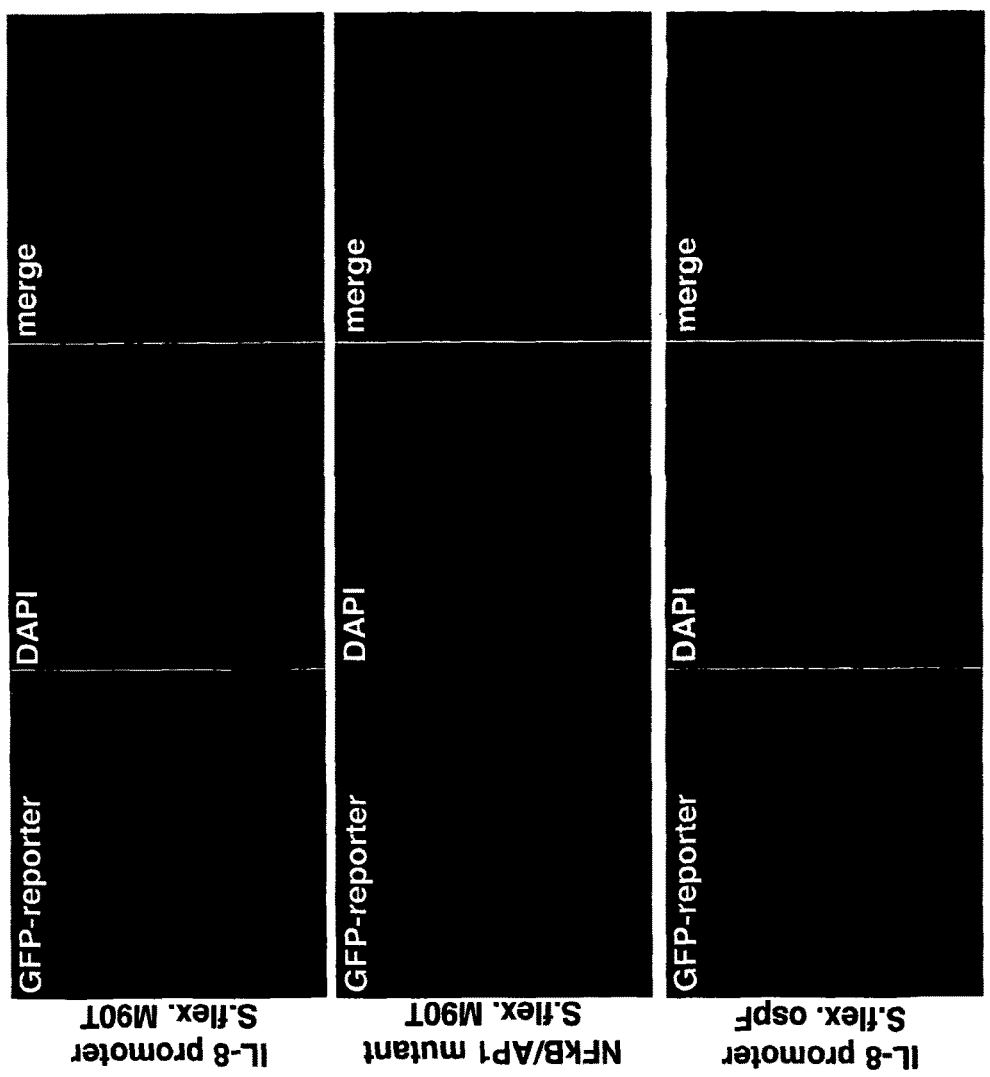
FIG. 3: challenge of cell lines IL8WT & IL8MUT with two different bacterial strains of *Shigella flexneri*.
Figure 4A:
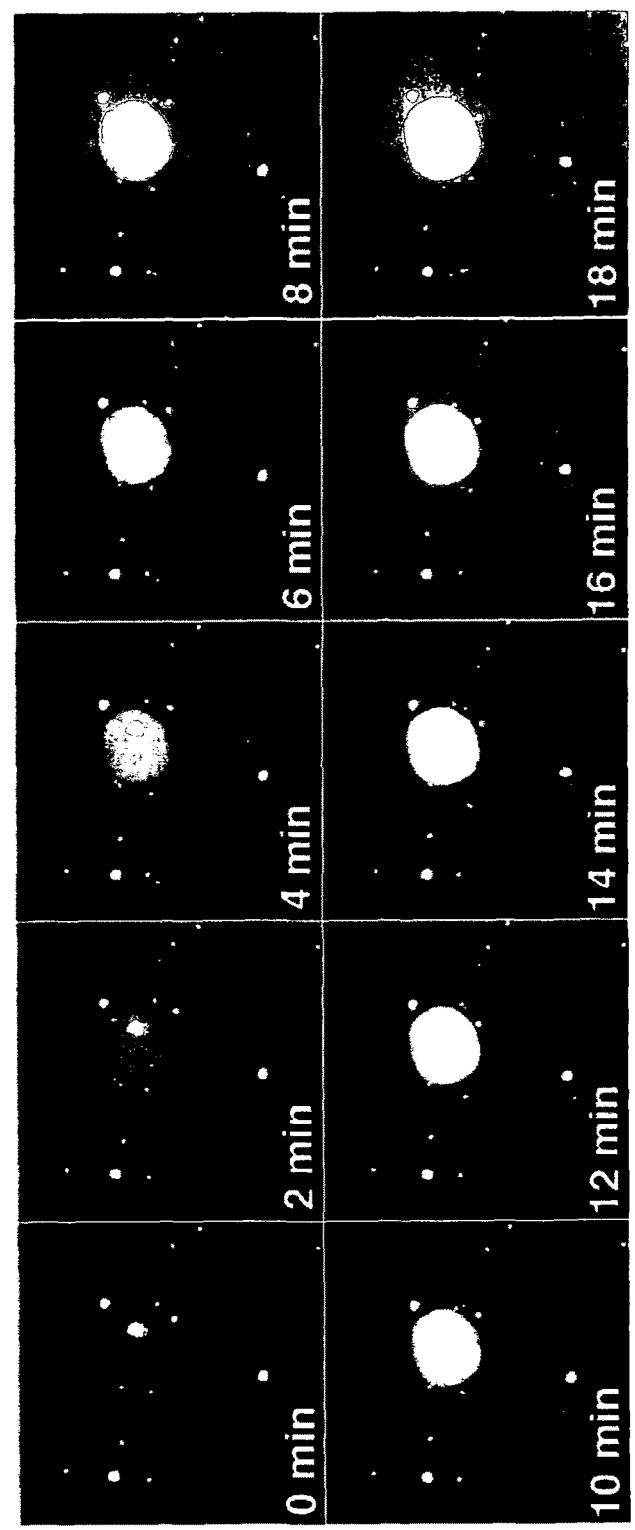
FIG. 4A: Cell line IL8WT transfected with molecular beacons complementary to the beacon barcode nucleotides encoded in each construct and incubated with *S. flexneri* M90T.
Figure 4B:
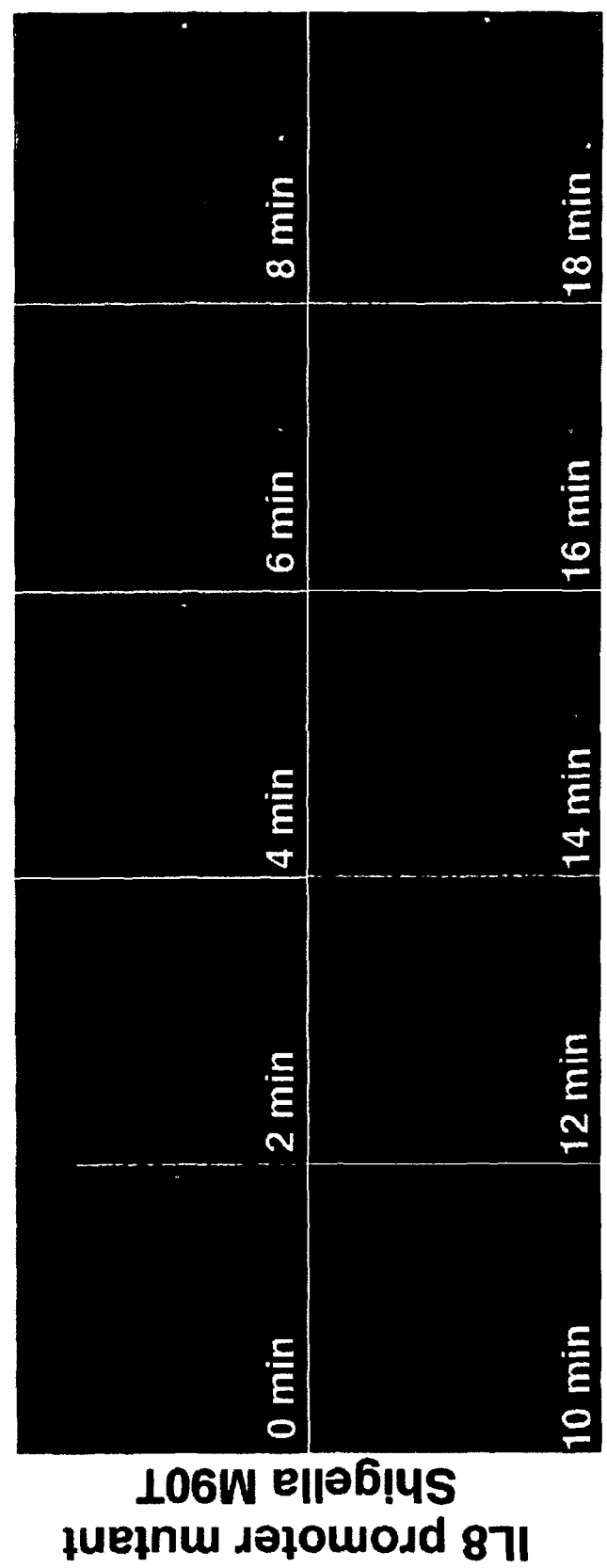
FIG. 4B: Cell line IL8MUT transfected with molecular beacons complementary to the beacon barcode nucleotides encoded in each construct and incubated with *S. flexneri* M90T.
Figure 4C:
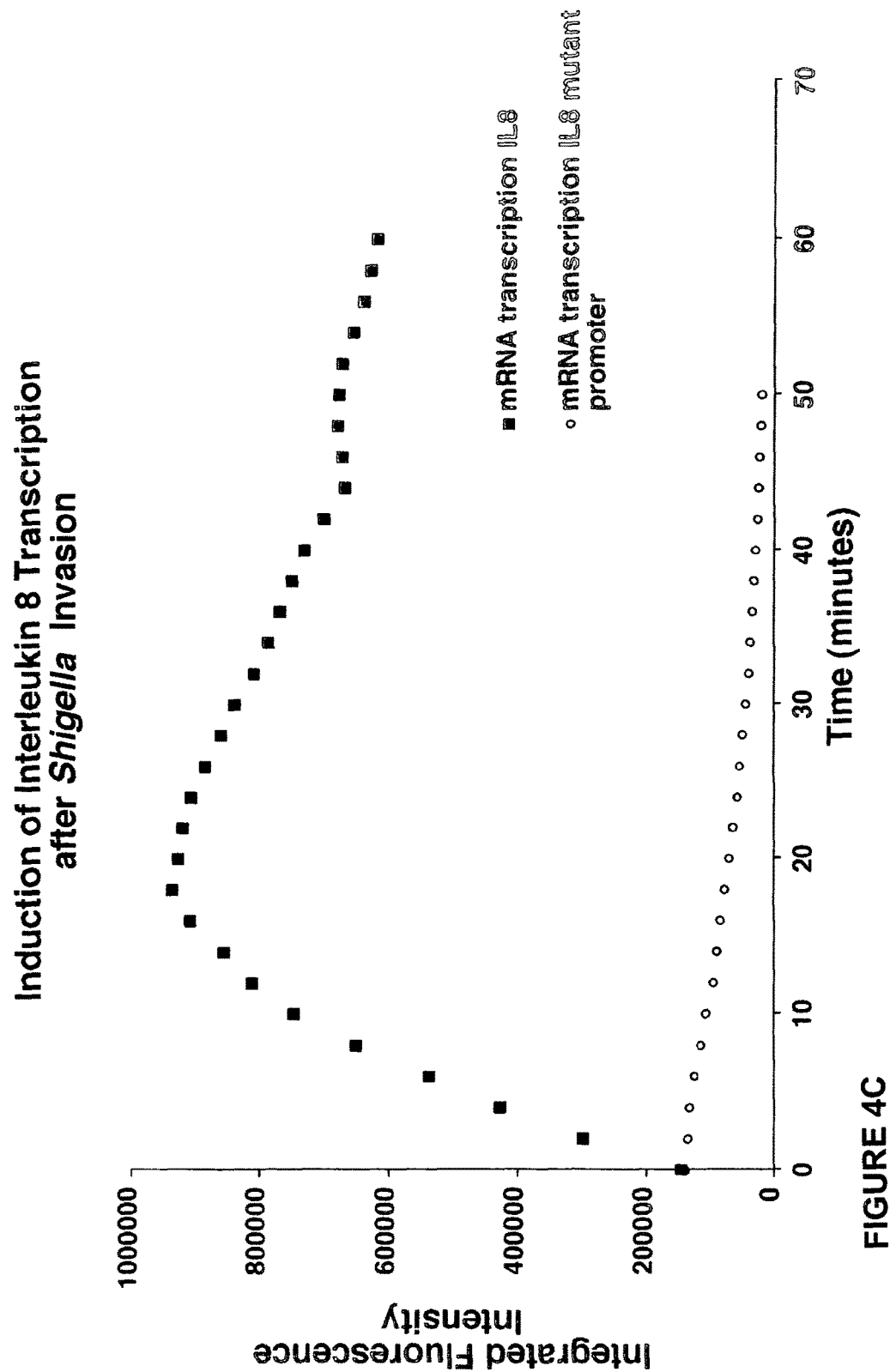
FIG. 4C: Kinetics of induction of IL8 transcription after *S. flexneri* M90T invasion.

B. Principle of molecular beacon barcode nucleotides. Barcode nucleotides can be constructed with a promoter of interest driving the expression of a fluorescent protein reporter upstream of the beacon barcode nucleotides. Alternatively they can contain a promoter driving a gene or interest fused to a fluorescent reporter upstream of the beacon barcode nucleotides. For experiments to monitor the pro-inflammatory response the first type of beacon barcode nucleotides was deployed. Two molecular beacon barcode constructs were made. IL8WT utilised the well-characterized minimal promoter of IL8 and was introduced upstream of green fluorescent protein (GFP) and a molecular beacon barcode nucleotides was introduced downstream of GFP with the 3' untranslated sequence. IL8MUT the second beacon barcode construct was identical in all respects to IL8WT, however, two mutations were introduced into the minimal promoter rendering it insensitive to activation. These constructs have been deposited as plasmids in *E. coli* strains, at the CNCM (located in Paris, France) under Number CNCM I-3818 (pJoMuIl8WT) and CNCM I-3819 (pJoMuIl8Mut) on Sep. 4, 2007.

The plasmids are in *E. coli* strain DH5α and are kanamicin-resistant.

The culture medium for growth is LB-medium with kanamycin and seeding is performed with LB-agar. Incubation is at 37° C. with constant shaking.

Storage is possible by freezing at −80° C. in suspending fluid of LB/50% glycerol with a cell concentration of $10^7$/ml.

C. Principle of live cell based assays using molecular beacons and beacon barcoded constructs. (From left to right) The beacon barcoded constructs IL8WT and IL8MUT are separately used to create two differing stable cell lines. These cell lines are checked for the stable integration of each construct. The cell based assay is performed by first introducing the appropriate molecular beacon via transfection or microinjection into the stable cell line. The cell is then incubated for a few hours prior to performing the experiment or screening assay. Different factors such as bacteria, tumor necrosis factor alpha (TNFα) or others are added to the cells. The transcriptional response of the cells is monitored via spinning disk confocal microscopy in appropriate environmental conditions (temperature & media). Molecular beacon fluorescence indicates the transcription of mRNA.

Hela cells lines stably transfected with pJoMu ll8WT or with pJoMuIl8Mut were deposited at the CNCM (Paris, France) on Sep. 4, 2007, under respective numbers CNCM I-3820 (JoMu) and CNCM I-3821 (JoMu mutant).

For each transfected cell line selection of stable transfectants was carried out with geneticin.

The culture medium of the transfected cell lines is DMEM "Dulbecco Modified Eagle Medium", +10% Fetal Bovine Calf Serum, +50 iu/ml Penicillin+Streptomycin, +2 mM L-glutamine; pH 7-4, optimal temperature 37° C., gaseous phase 5% $CO_2$.

The conditions for cultivation are for attached monolayer cells with a population doubling time of 16 h an optimal split ratio of once in 3-4 days and a lifespan corresponding to a cancer cell line. Sub-culture is achieved by simple trypsin treatment similar to the splitting of Hela cells.

Storage is possible in liquid nitrogen.

FIG. 2

Prior to performing assays to follow the transcriptional response of the cell lines IL8WT & IL8MUT we checked whether the construct was functional and responsive to standard stimuli of the IL8 promoter. TNFα is known to stimulate directly the IL8 promoter and we intentionally constructed the IL8MUT promoter to be refractive to TNFα that should cause IL8WT to drive expression of a GFP. We performed the experiment under four differing conditions to satisfy ourselves that the both beacon barcode nucleotides functioned as expected.

Condition 1: IL8WT with TNFα Induction

IL8WT construct containing cells stimulated with TNFα and monitored over several hours following the addition of TNFα. The cells were stained with DAPI to mark their presence in the microscopic field. Approximately four hours following TNFα stimulation GFP was seen in several of the cells in the field (Row 1 column 1 & 3).

Condition 2: IL8WT with No Induction

IL8WT construct containing cells monitored over several hours. Unless methods to which the IL8 promoter is responsive to are used to stimulate the pro-inflammatory response, no fluorescence in GFP is observed. A very low level of background fluorescence is observed indicating that in some cells a low level of pro-inflammatory stimulus may be active. (Row 2 column 1 & 3).

Condition 3: IL8Mut (NFKB/AP1 Mutant) with TNFα Induction

IL8MUT construct containing cells stimulated with TNFα and monitored over several hours following the addition of TNFα. No increase in fluorescence is observed and there is no visible level of background fluorescence that is observed in Condition 2. (Row 3 column 1 & 3).

Condition 4: IL8Mut (NFKB/AP1 Mutant) with No Induction

IL8MUT construct containing cells monitored over several hours. No increase in fluorescence is observed over the period of the assay. (Row 4 column 1 & 3).

FIG. 3

The cell lines IL8WT & IL8MUT were challenged with two different bacterial strains of *Shigella flexneri*. One strain, *S. flexneri* M90T is known to elicit a strong pro-inflammatory response in human cells. The second strain, *S. flexneri* OspF (Arbibe et al, 2007) was used since its activation of the pro-inflammatory response is ambiguous. In all cases the cells were incubated with either strain of *S. flexneri* for 30 minutes. The cells were then carefully washed and the media exchanged with one containing 10 μM gentomicin. The cells were then incubated at 37° C. for 3.5 hrs whilst monitoring them for activity via confocal microscopy. We performed the experiment under the following three differing conditions.

Condition 1: IL8WT with *S. flexneri* M90T

IL8WT construct containing cells incubated with *S. flexneri* M90T for 30 minutes were monitored over several hours via Nipkow disk confocal microscopy. The cells were stained with DAPI to mark their presence in the microscopic field. Approximately three hours following incubation GFP was seen in several of the cells in the field (Rox 1 column 1 & 3).

Condition 2: IL8MUT with *S. flexneri* M90T

IL8MUT construct containing cells monitored were incubated with *S. flexneri* M90T for 30 minutes. The cells were then monitored over several hours via Nipkow disk confocal microscopy. No GFP fluorescence was observed even after monitoring for several hours indicating the promoter was refractive to stimulation by the inflammatory response. (Row 2 column 1 & 3)

Condition 3: IL8WT with *S. flexneri* OspF

IL8WT construct containing cells incubated with *S. flexnery* OspF for 30 minutes were monitored over several hours via nipkow disk confocal microscopy. Almost 4 hrs after incubation a low level of GFP fluorescence was observed in some cells. The mechanism by which OspF variants induce the inflammatory response is ambiguous. OspF has been implemented in causing specific chromatin remodelling events in the host leading to stimulation of the pro-inflammatory response (Row 3 column 1 & 3).

FIG. 4

The cell lines IL8WT & IL8MUT were transfected with molecular beacons complementary to the beacon barcode nucleotides encoded in each construct. The transfected cells were incubated with the molecular beacons alone for at least 2 hours. The medium was then exchanged and the two cell lines were challenged with the bacterial strain *Shigella flexneri* M90T known to elicit a strong pro-inflammatory response in human cells. *S. flexneri* M90T was added to the cells whilst monitoring them for transcriptional activity via Nipkow disk confocal microscopy.

A. IL8WT cells incubated with *S. flexneri* M90T. Within a few minutes of the addition of the bacteria a rapid rise in molecular beacon fluorescence is observed. IL8 induction is seen to rise rapidly (C) to a level that saturates the CCD detector after 20 minutes. See Movie 1. We observed several in various levels of induction and have selected a cell within the field for which we observe such induction from its "off" state to transcription.

B. IL8MUT cells incubated with *S. flexneri* M90T. After monitoring the cells over 50 minutes no gain in fluorescent intensity is observed indicating no activation of the IL8MUT construct in the cells. Here the level of fluorescence is shown over a similar period as in A. See Movie 2.

Kinetics of induction of IL8 transcription after *S. flexneri* M90T invasion. The Y axis indicates Integrated Fluorescence while the X axis is time. The graph shows the rapid induction of IL8 which is induced by two-fold in as little as 8 minutes. The peak in fluorescent intensity reached after 20 minutes is indicative of saturation of the CCD detector and not necessarily of the arrest in induction of the pathway.

FIG. 5:

Color combination illustration to profile multiple genes.

Figure 5C:
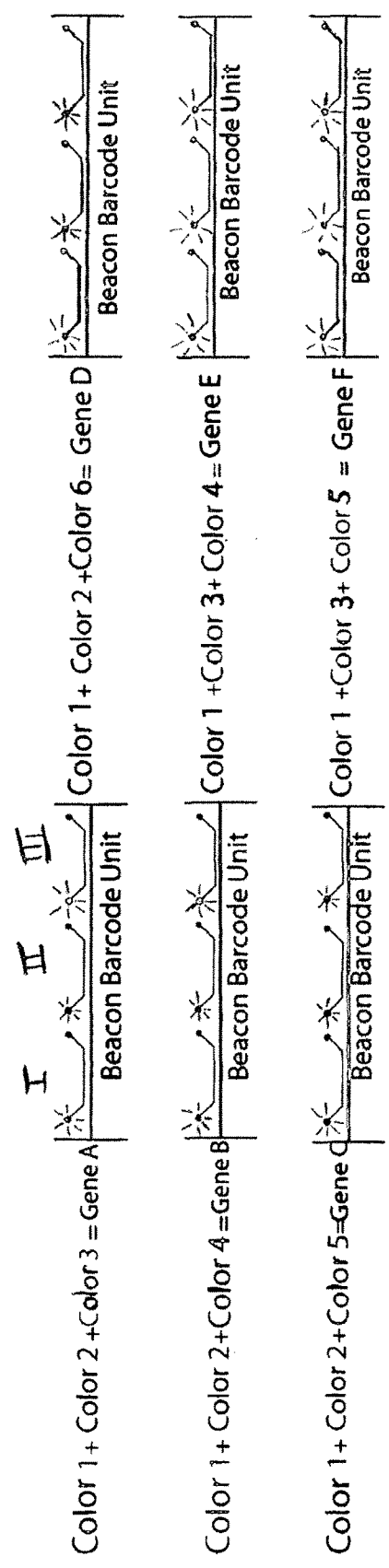
FIG. 5C: Color combinations to profile multiple genes in a single cell.

FIG. 5A: Dual color coding scheme. The different dots correspond to different colors of the fluorophores. One Beacon Barcode unit consists of 2 sequences Type I & Type II. Each Type can be bound to a molecular beacon or nucleic acid probe. Probes complementary to Type I can be of a similar or different color than Type II. By using two differing colors bound to each barcode unit, as outlined in this scheme, a combinatorial color code can be used to profile multiple genes in a single cell.

FIG. 5B: Triplex color coding scheme. In this scheme, one Beacon Barcode unit consists of 3 sequences Type I, Type II & Type III. Each Type can be bound to a molecular beacon or nucleic acid probe.

Probes complementary to Type I can be of a similar or different color than Type II and Type III. By using three differing colors bound to each barcode unit, as outlined in this scheme, a combinatorial color can be used to profile multiple genes (20 genes) in a single cell.

FIG. 6: Nucleotide sequences of the inserts used for the preparation of core vectors. "kana" (SEQ ID NO: 14), "zeo" (SEQ ID NO: 15), "hydro" (SEQ ID NO: 16) illustrate sequences of antibiotic resistance genes. "IL10" (SEQ ID NO: 17), "CCL20" (SEQ ID NO: 18), "ICAM-1" (SEQ ID NO: 19), "TGF-beta" (SEQ ID NO: 20) and "c-fos" (SEQ ID NO: 21) illustrate sequences of promoters suitable for the vectors.

AB-repeat (SEQ ID NO: 22), AC-repeat (SEQ ID NO: 23) and CB-repeat (SEQ ID NO: 24) are sequences of beacon binding sites.

Figure 7A:
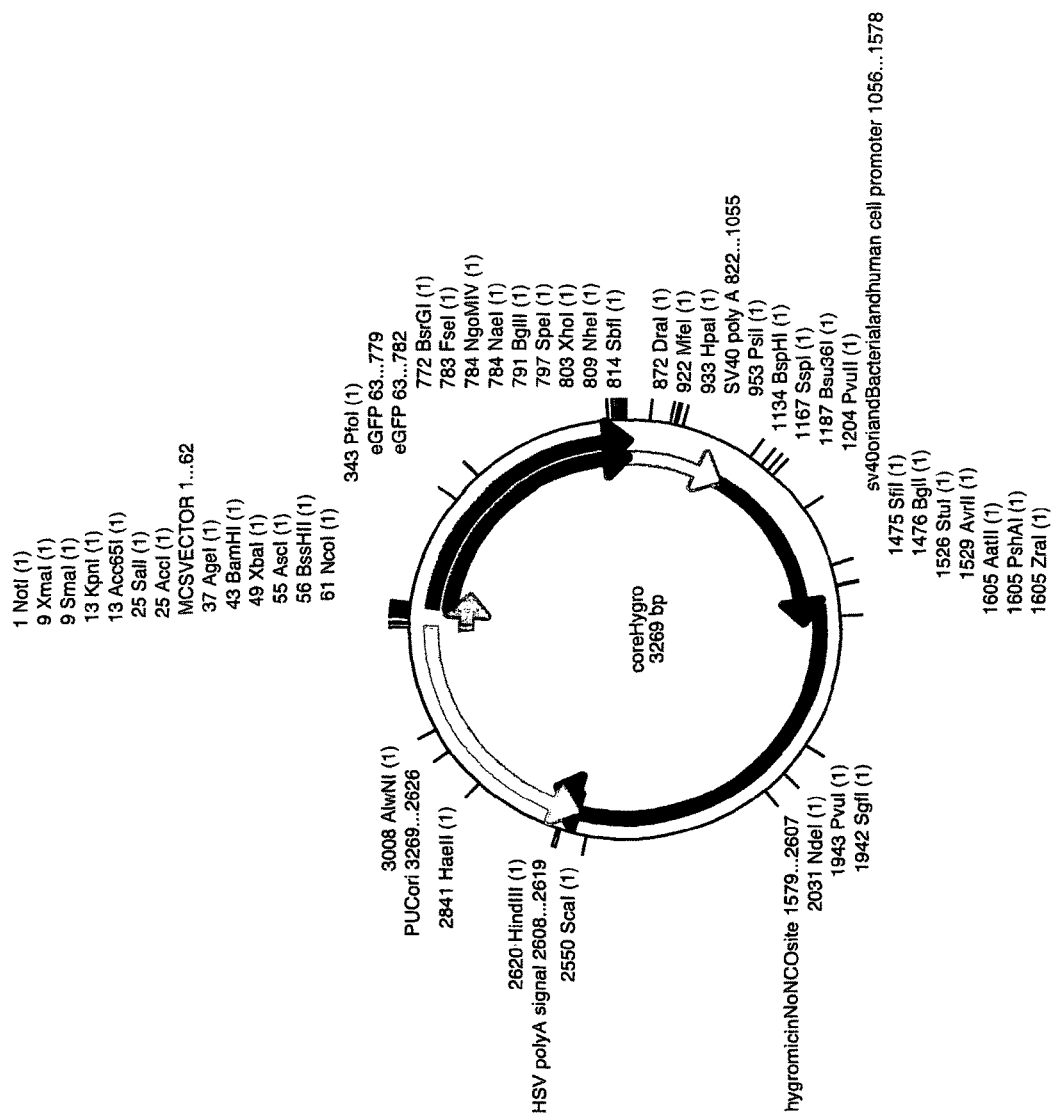
FIG. 7A: vector plasmid constructs expressing respectively hygromycin resistance gene.
Figure 7B:
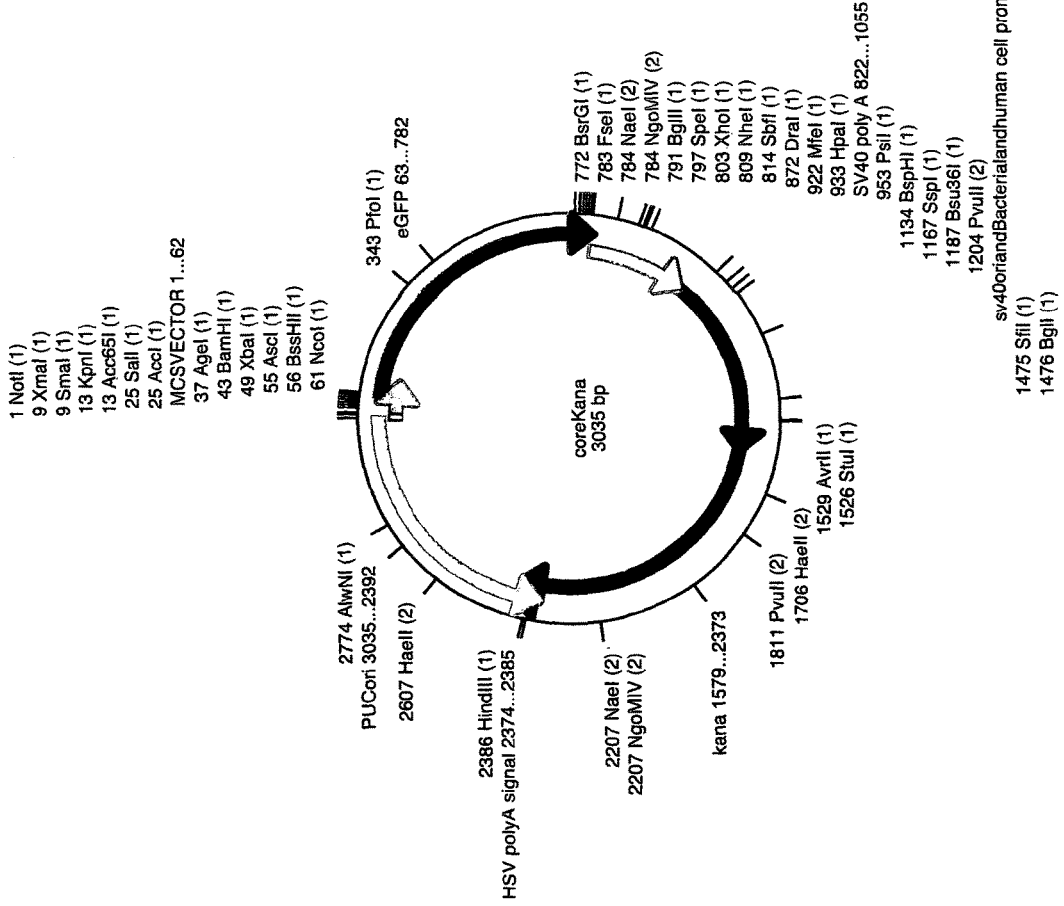
FIG. 7B: vector plasmid constructs expressing respectively kanamycin resistance gene.
Figure 7:
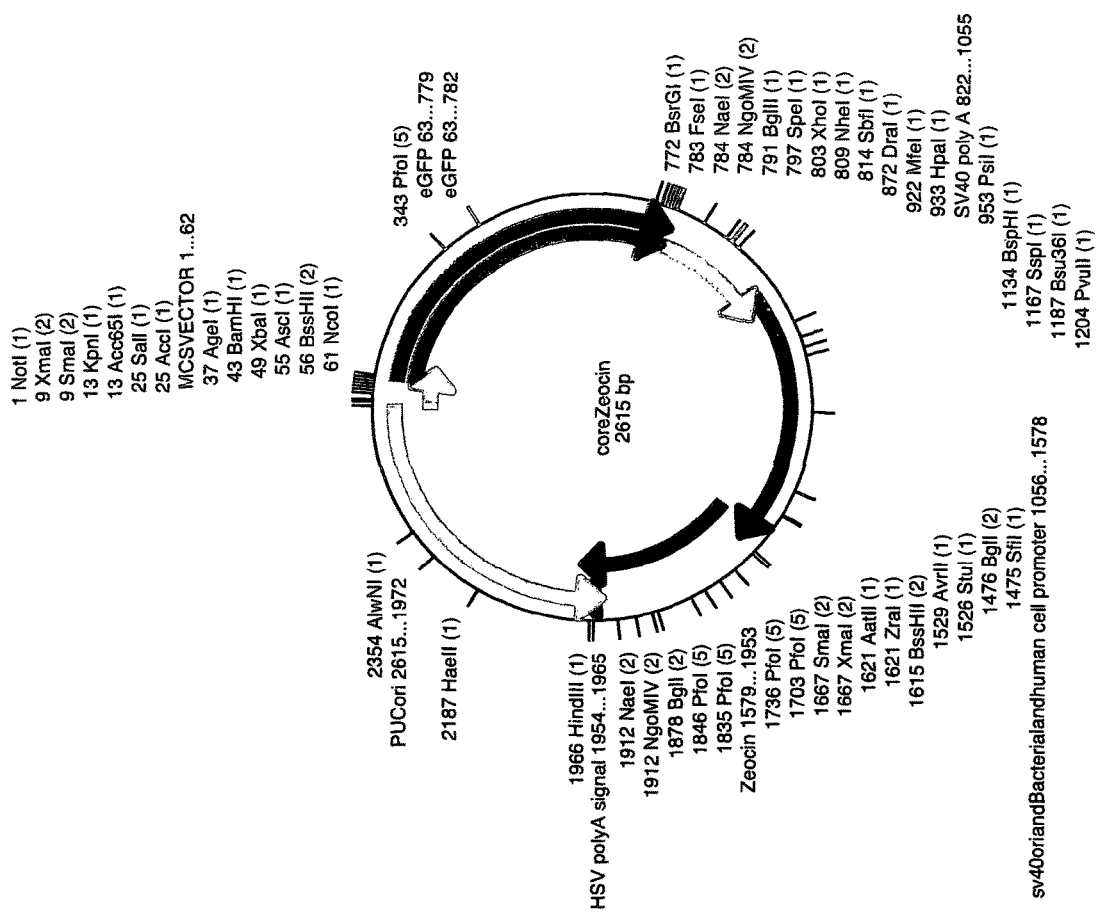
FIG. 7C: vector plasmid constructs expressing respectively Zeocin resistance gene.

FIG. 7: FIG. 7 illustrates the vector plasmid constructs expressing respectively hygromycin resistance gene, kanamycin resistance gene and Zeocin resistance gene. In the vectors, inserts corresponding to GFP sequence taken from Clontech vector pEGFP-N1 are used. The on sequence inserted comes from pBluescript. The invention relates to the use of any of these elements as inserts in a vector of the invention, containing a promoter and a polynucleotide for a resistance gene, and relates to any combination of a promoter and resistance gene polynucleotide in a vector.

I—PREPARATION AND USE OF MOLECULAR TOOLS TO STUDY TRANSCRIPTIONAL RESPONSE PATTERN IN A HOST CELL

Examples

To perform initial studies of single molecule gene expression it was chosen to examine pathogen induced transcription in host (human) cells. A particular model system is the invasion by *Shigella flexineri* of human cells. Recent work has postulated that *S. flexneri* specifically alters the transcriptional status of invaded cells, promoting immune responses opportunistic for the bacterium. Transcriptome analysis using microarrays has suggested specific host genes that *S. flexneri* targets during invasion of host cells, inducing a very specific pattern of transcriptional response. We have developed molecular tools to follow this transcriptional response in real-time. Combined with existing image-based methods to monitor biochemical, protein and morpholocial changes, we have built a platform that provides a revolutionary way to perform experimental biology. Experiments are carried out in single cells addressing a single host gene and its response to bacterial invasion are investigated in high-throughput fashion. Further the platform can be used to screen for chemical factors, *S. flexneri* mutants, or host mutants (using RNAi), that are able to alter host gene response favoring the host or the bacterium.

Molecular Biology

Two complementary oligonucleotide sequences of 81 nt were designed, containing two molecular beacon binding sites with an intervening sequence of 8nt. Sequence 1 (+ve strand) was 5'-TTCTCTTCAAACTTTTCCGCTTTT-3' (SEQ ID NO: 7) and Sequence 2 (+ve strand) was 5'-CGC-CAAAACCTATTATCTTAAGTC-3' (SEQ ID NO: 8). The entire positive strand of the oligonucleotide sequence was 5'-ACGCGTCGACTTCTCTTCAAACTTTTCC GCTTTTAGAGAGAGCGCCAAAACCTATTATCT-TAAGTC CTCGAG GGATCC GCG-3' (SEQ ID NO: 9) which included at the 5' end a SalI restriction enzyme recognition site, and at the 3' end XhoI and BamHI restriction enzyme recognition sites, respectively. The negative and positive oligonucleotide strands were solubilized in 20 mM Tris.HCL (pH 8.0), and 2.5 mM MgCl2 at room temperature before being heated to 95° C. and cooled on ice. The now double-stranded oligonucleotide was digested with Bam HI and Sal I and cloned into a pUC19 (Sambrook, J. et al, Molecular Cloning: A laboratory Manual. $2^{nd}$. New York: Cold Spring Harbor Laboratory 18, 58 (1989)) plasmid (containing G418 and Ampicilin selection markers) opened with Bam HI and Sal I to create pJOMU. pJOMU was then digested in two separate digests, Hind III with Xho I and Ecor RI with Sal I; the fragments from each digest were gel purified and both were cloned into pUC19 opened with Hind III and Eco RI to create pJOMU2. The latter two steps were repeated several times resulting in multimerization of Sequence 1 & 2 creating 64 molecular beacon binding sites in plasmid pJOMU64. Using forward and reverse PCR primers and the minimal human IL8 gene as a template (Hltmann et al. 1999), three variants of the IL8 promoter were amplified and subsequently cloned into a pGFP plasmid 5' of a Green Fluorescent Portein nucleotide coding sequence thus crating three variants of pIL8GFP (one wild type variant and two mutant variants); the primers for this amplification were IL8 Forward primer: 5'-CACTGAAT-TAATGAAAGTGTGATGACTCAGGTTTGCCC-3' (SEQ ID NO: 10) and IL8 reverse primer 5'-TCAGTGGCTAGC-GAAGCTTGTGTGCTCTGCTGTCT-3' (SEQ ID NO: 11). The IL8-GFP fusions with one wild type and two mutant variants, (promoter of IL8 inserted upstream of GFP) were excised from pIL8GFP using AseI and NotI sites and cloned 5' (upstream) of the 64 molecular beacon binding sites in pJOMU64 to create pJOMU-IL8 wt and pJOMUIL8mut1 and pJOMUIL8 mut2.

Molecular Beacon Design and Synthesis

Molecular beacons were synthesized on an Applied Biosystems 394 DNA synthesizer (Foster City, Calif.) using 2'-O-methylribonucleotide β-cyanoethyl phosphoramidites. The sequences of the molecular beacons were for MB 1: Cy5-5'-GCUGC AAAAGCGGAAAAGUUUGAAGAGAA GCAGC-3' (SEQ ID NO: 12)-BHQ3 complementary to Sequence 1 and for MB 2: CY5-5'-CGACC GAC-UUAAGAUAAUAGGUUUUGGCG GGUCG-3' (SEQ ID NO: 13)-BHQ3 complementary to Sequence 2. For both molecular beacons the underlined sequence represented the complementary ends of the molecular beacon. For the synthesis of molecular beacons that had a quencher at their 3' end, a controlled-pore glass column containing Black Hole Quencher 3 (BHQ3) was used. Each molecular beacon was purified by high-pressure liquid chromatography (HPLC) through a C-18 reverse-phase column. DNA synthesis reagents were obtained from Glen Research (Sterling, Va.) and Biosearch Technologies (Novato, Calif.) and activated fluorophores were obtained from Molecular Probes (Eugene, Oreg.).

Molecular Beacon-Barcode Binding In Vitro Assay

The signal-to background ratio of all molecular beacons was measured with a spectrofluorometer. First, the baseline fluorescence of the solution was determined. Subsequently, the fluorescence of a 200 µl solution containing 30 nM molecular beacons in 5 mM MgCl2 and 20 mM Tris-HCl (pH 8.0) was determined at 25° C. with a QuantaMaster spectrofluorometer (Photon Technology International, South Brunswick, N.J.) using maximal excitation and emission wavelengths. A two-fold molar excess of the in vitro transcribed mRNA of the pJOMU-IL8 target was added and the rise in fluorescence was monitored until it reached a stable level. The rise in fluorescence over the signal of the molecular beacon alone (without the addition of mRNA target) was calculated to determine the signal-to-background ratio and quenching efficiency of the molecular beacon.

Cell Culture

All cell culture reagents were purchased from Gibco-Invitrogen. Eukaryotic cells were cultured in DMEM supplemented with 10% v/v Foetal Bovine Calf Serum (FBS), 50 iu/ml Penicillin, 50 µg/ml Streptomycin and 2 mM L-glutamine at 37° C., 5% $CO_2$. All live cell fluorescent microscopy was performed in EM buffer (120 mM NaCl, 7 mM KCl, 1.8 mM $CaCl_2$, 0.8 mM $MgCl_2$, 5 mM Glucose, 25 mM Hepes at pH 7.3).

Establishing Stable Cell Lines

Cell lines stably expressing the molecular beacon 'barcode' constructs (see section on molecular biology) were established using standard protocols (Ref. Maniatis et al 1989). Briefly, $2.5 \times 10^5$ HeLa cells were transfected with the beacon barcode constructs (pJOMU-IL8 wt and pJOMUIL8mut1), using the Fugene (Roche, Switzerland) transfection reagent according to the manufacturer's protocols. 24 hrs after transfection, geneticin (G418) (Invitrogen, Carlsbad, Calif.) was added to the cells at a final concentration of 400 µg/ml. Then they were maintained for two weeks to eliminate cells that did not contain a stable integration of the promoter molecular beacon barcode construct. Subsequently, cells were split and diluted to allow the isolation of individual cell clones with stably integrated plasmids. After continuous selection with 400 µg/ml G418 for four more weeks, the obtained cell lines from individual clones were continued in the presence of G418, and were used for functional assays.

Bacterial Culture

M90T (Sansonetti P. J. et al, Infection and Immunity March 1982, p. 852-860) is the invasive wild-type strain of S. flexneri. M90TafaI is the wild type strain expressing the adhesin, afaI. BS176afaI is a non-invasive mutant of M90T cured of the virulence plasmid and expresses the adhesion, afaI. In the case of ospF, bacteria were treated with poly-L-lysine before invasion to increase bacterial infection. All bacterial strains used in this study were grown at 37° C. in Tryptic casein soy broth (TCSB) supplemented with 100 µg/ml ampicillin.

Injection and Transfection of Molecular Beacons

Molecular beacons were dissolved at a concentration of 2.5 ng/µl, and an approx 0.1- to 1-femtolitre solution was microinjected into each cell by using a FemtoJet microinjection apparatus (Eppendorf). In order to introduce molecular beacons into living cells via transfection, the cells were cultured to a 30 percent confluency and washed with serum free Opti-MEM1 (Invitrogen, Carsbad, Calif.). Transfection reagent oligofectamine (Invitrogen, Carlsbad, Calif.) was incubated for five minutes in serum free medium (1 µl reagent added to 9 µl Opti-MEM1) prior to mixing with molecular beacons (MB1 and MB2) (1 ng/µl in Opti-MEM1). The molecular beacons and the transfection reagent were incubated for 20 minutes at 25° C. to form complexes between them. After diluting these complexes with 200 µl serum free medium they were added to the cells. The cells were incubated for 3 hours in presence of these complexes. Finally, the cells were washed with EM medium and imaged.

Bacterial Infection

The cells with the stably integrated promoter beacon barcode reporters were seeded at a density of $2 \times 10^5$ cells per well in 35 nm MATTEK, glass-bottomed culture dishes (Mattek Cooperation, PA). 24 h prior to infection the required S. flexneri cultures were inoculated in TCSB and grown overnight at 37° C. Overnight bacterial cultures were inoculated at a 1/100 dilution in TCSB and grown to an optical density at 600 nm ($OD_{600}$) of ~0.3. Prior to infection, bacteria were washed twice with PBS (phosphate buffered saline) and resuspended in EM. The molecular beacon injected or transfected cells were washed twice with PBS and maintained in EM. Finally, the cells were directly infected with bacteria at a MOI (multiplicity of infection) of 10, and maintained at 37° C. using a heating chamber. Bacterial invasion was followed by multi-dimensional time-lapse microscopy.

Microscopy and Live Cell Imaging

Bacterial invasion was followed using a Perkin Elmer Nipkow disk confocal microscope (Perkin Elmer, UK) with a 40× objective. For live cell imaging, we used MATTEK glass-bottom culture dishes (Mattek Cooperation, PA) possessing a 0.17 mm cover glass with a coating of conductive material at their bottom to permit controlled heating. These dishes were coated with gelatine prior to plating the cells. The temperature of the MATTEK culture dishes and the microscope objective was maintained at 37° C. During microinjection and imaging, the cells were maintained in EM media. Microscopy was performed in multiple dimensions using a ZEISS (Zeiss, Germany) microscope equipped with Ar and He/Ne laser connected to a Perkin Elmer Nipkow Disk.

Data Analysis

All data analysis and quantification was performed using the freeware ImageJ. For quantification, images were thresholded above the cytosolic background of molecular beacon containing cells. Then, the integrated density of the fluorescence inside the cell nucleus was measured over the timecourse of bacterial invasion. Results of this quantification were plotted using Excel (Microsoft, Seattle, Wash.).

II—DESIGN OF OPTIMIZED VECTORS WITH PROMOTER-BEACON BARCODE SYSTEM

We have generated a set of novel vectors for optimized usage of the promoter-beacon barcode system. The core vector contains extended repeats of the beacon binding sites. The exact beacon binding sites are made of the binding sites A and B, B and C, and A and C as illustrated in FIG. 6. Furthermore, we generated vectors containing the inverse binding sequences that will bind to different molecular beacons. Together, this generated 6 different beacon binding sites. The novel designed vectors can easily be modified with molecular biological techniques, to change or to add some inserts, for example to change the promoter sequences, or to change the antibiotic resistance for selection. The vectors are illustrated in FIG. 7.

In addition, we generated vectors that contain sequences for a number of promoters. In addition to the interleukin 8 minimal promoter, vectors containing a promoter selected from the CCL20 promoter, and the interleukin 10 promoter have been prepared. Cell lines containing these new promoter-reporter fusions are developed. This will lead to cell lines that can respond to signals leading to an induction of interleukin 10 or CCL20.

In order to spread the spectrum of eukaryotic cells containing our promoter-reporter constructions further cells were used. In addition to non-polar HeLa cells, we have generated cell lines with the promoter-reporters in polarized cells and in cells of the immune system. These cell lines were derived from Caco2 cells and from U937 cells. So far, we have generated cell lines with the interleukin 8 promoter connected with the AB repeat sites.

Methods for the Vector and Cell Line Construction

All procedures for the construction of the novel vectors and the cell lines are described in detail in "Molecular Cloning: A Laboratory Manual" by Joseph Sambrook and David Russell (CSHL press, 2001). For better understanding a short description is added below:

Three vectors (attached maps in FIG. 7) have been conceived that are named "Core Vectors" containing an OR1, a GFP sequence and an antibiotic resistance (either kanamycin, zeozin, or hygromycin) and have been constructed by PCR cloning (Maniatis). Subsequently, one of the following promoter has been introduced upstream of the GFP sequence: IL10, CCL20, cfos, TGFbeta, ICAM-1 to generate 5 vectors. These five vectors express GFP from the five different promoters. Afterwards multimerized beacon binding sequences (either AB, AC, or BC) have been introduced downstream the GFP sequence, but upstream the 3'-UTR sequence, so that induction of the promoters leads to transcripts containing the GFP sequence and the beacon binding repeats.

For the beacon binding repeats, either 120 or 160 repeat sites were generated by multi-step cloning (see Maniatis). The promoter-reporter containing vectors either contain therefore 120 or 160 repeats. For introducing the repeat sites, we opened the vector only with one single restriction enzyme, resulting in the insertion of the repeats with the possibility to be inserted in one direction or the other direction. With this trick, we generated six different beacon binding sites: AB, BC, AC, ABinverse, AC inverse, and BC inverse.

Globally, this procedure led to vectors containing from upstream to downstream 5 elements: An ori, a promoter, a GFP sequence, the beacon binding repeats and an antibiotic resistance.

These vectors are suitable for use for the generation of stable cell lines by transfection (see Maniatis), and can be used in conjunction with the beacon reporter system. The transfection procedures for stable cell line generation use standard transfection procedures, and beacon transfection has been described in detail above.

REFERENCES

1. Arbibe, L. et al. An injected bacterial effector targets chromatin access for transcription factor NF-kappaB to alter transcription of host genes involved in immune responses. *Nat Immunol* 8, 47-56 (2007).
2. Monack D M, Mueller A, Falkow S. Persistent bacterial infections: the interface of the pathogen and the host immune system. Nat Rev Microbiol. 2004 September; 2(9):747-65.
3. Kyttaris V C, Juang Y T, Tsokos G C. Immune cells and cytokines in systemic lupus erythematosus: an update. Curr Opin Rheumatol. 2005 September; 17(5):518-22
4. Barabasi, A. L. & Oltvai, Z. N. Network biology: understanding the cell's functional organization. *Nat Rev Genet.* 5, 101-113 (2004).
5. Pepperkok, R. & Ellenberg, J. High-throughput fluorescence microscopy for systems biology. *Nat Rev Mol Cell Biol* 7, 690-696 (2006).
6. Bastiaens, P. I. & Pepperkok, R. Observing proteins in their natural habitat: the living cell. *Trends Biochem. Sci.* 25, 631-637 (2000).
7. Meyer, T. & Teruel, M. N. Fluorescence imaging of signaling networks. *Trends Cell Biol.* 13, 101-106 (2003).
8. Wouters, F. S., Verveer, P. J. & Bastiaens, P. I. Imaging biochemistry inside cells. *Trends Cell Biol.* 11, 203-211 (2001).
9. Karin, M. Nuclear factor-kappaB in cancer development and progression. *Nature* 441, 431-436 (2006).
10. Karin, M., Lawrence, T. & Nizet, V. Innate immunity gone awry: linking microbial infections to chronic inflammation and cancer. *Cell* 124, 823-835 (2006).

11. Genovesio, A., Belhassine, Z. & Olivo-Marin, J. Adaptive gating in Gaussian Bayesian multi-target tracking. *Image Processing, 2004. ICIP '04. 2004 International Conference on* 1 (2004).
12. Bork, P. & Serrano, L. Towards cellular systems in 4D. *Cell* 121, 507-509 (2005).
13. Genovesio, A., Zhang, B. & Olivo-Marin, J. Interacting multiple model based method to track moving fluorescent biological spots. *Biomedical Imaging: Macro to Nano, 2004. IEEE International Symposium on,* 1239-1242 (2004).
14. Olivo-Marin, J. Extraction of spots in biological images using multiscale products. *Pattern Recognition* 35, 1989-1996 (2002).
15. Starkuviene, V. High-content screening microscopy identifies novel proteins with a putative role in secretory membrane traffic. *Genome Res.* 14, 1948-1956 (2004).
16. Liebel, U. A microscope-based screening platform for large-scale functional protein analysis in intact cells. *FEBS Lett.* 554, 394-398 (2003).
17. Shav-Tal, Y. et al. Dynamics of single mRNPs in nuclei of living cells. *Science* 304, 1797-1800 (2004).
18. Mhlanga, M. M., Vargas, D. Y., Fung, C. W., Kramer, F. R. & Tyagi, S. tRNA-linked molecular beacons for imaging mRNAs in the cytoplasm of living cells. *Nucleic Acids Res* 33, 1902-1912 (2005).
19. Bratu, D. P. Molecular beacons: Fluorescent probes for detection of endogenous mRNAs in living cells. *Methods Mol Biol* 319, 1-14 (2006).
20. Tyagi, S. & Kramer, F. R. Molecular beacons: probes that fluoresce upon hybridization. *Nat Biotechnol* 14, 303-308 (1996).
21. Bertrand, E. et al. Localization of ASH1 mRNA particles in living yeast. *Mol Cell* 2, 437-445 (1998).
22. Shav-Tal, Y. et al. Dynamics of single mRNPs in nuclei of living cells. *Science* 304, 1797-1800 (2004).
23. Vargas et al
24. Bratu, D. P., Cha B. J., Mhlanga, M. M., Kramer, F. R., and Tyagi, S. (2003). Visualizing the distribution and transport of mRNAs in living cells. *Proc Natl Acad Sci USA*
25. Matsuo, T. (1998). In situ visualization of messenger RNA for basic fibroblast growth factor in living cells. *Biochim Biophys Acta* 1379, 178-84.
26. Sokol, D. L., Zhang, X., Lu, P. & Gewirtz, A. M. (1998). Real time detection of DNA.RNA hybridization in living cells. *Proc Natl Acad Sci USA* 95, 11538-43.
27. Southern, E. M., Milner, N. & Mir, K. U. (1997). Discovering antisense reagents by hybridization of RNA to oligonucleotide arrays. *Ciba Found Symp* 209, 38-44; discussion 44-6.
28. Ho, S. P., Bao, Y., Lesher, T., Malhotra, R., Ma, L. Y., Fluharty, S. J. & Sakai, R. R. (1998). Mapping of RNA accessible sites for antisense experiments with oligonucleotide libraries. *Nat Biotechnol* 16, 59-63
29. Mir, K. U. & Southern, E. M. Determining the influence of structure on hybridization using oligonucleotide arrays. *Nat Biotechnol* 17, 788-792 (1999).
30. Milner, N., Mir, K. U. & Southern, E. M. Selecting effective antisense reagents on combinatorial oligonucleotide arrays. *Nat Biotechnol* 15, 537-541 (1997).
31. Southern, E. M., Milner, N. & Mir, K. U. Discovering antisense reagents by hybridization of RNA to oligonucleotide arrays. *Ciba Found Symp* 209, 38-44; discussion 44-36 (1997).
32. Sohail, M. et al. Antisense oligonucleotides selected by hybridisation to scanning arrays are effective reagents in vivo. *Nucleic Acids Res* 29, 2041-2051 (2001).
33. Ooms, M., Verhoef, K., Southern, E., Huthoff, H. & Berkhout, B. Probing alternative foldings of the HIV-1 leader RNA by antisense oligonucleotide scanning arrays. *Nucleic Acids Res* 32, 819-827 (2004).
34. Nguyen, H. K. & Southern, E. M. Minimising the secondary structure of DNA targets by incorporation of a modified deoxynucleoside: implications for nucleic acid analysis by hybridisation. *Nucleic Acids Res* 28, 3904-3909 (2000).
35. Sohail, M., Doran, G., Riedemann, J., Macaulay, V. & Southern, E. M. A simple and cost-effective method for producing small interfering RNAs with high efficacy. *Nucleic Acids Res* 31, e38 (2003).
36. Wittwer, C. T., Herrmann, M. G., Moss, A. A. & Rasmussen, R. P. Continuous fluorescence monitoring of rapid cycle DNA amplification. *Biotechniques* 22, 130-131, 134-138 (1997).
37. Li, Q., Luan, G., Guo, Q. & Liang, J. A new class of homogeneous nucleic acid probes based on specific displacement hybridization. *Nucleic Acids Res* 30, E5 (2002).
38. Solinas, A. et al. Duplex Scorpion primers in SNP analysis and FRET applications. *Nucleic Acids Res* 29, E96 (2001).
39. Sambrook, J., Fritsch, E. & Maniatis, T. Molecular Cloning: A Laboratory Manual. 2nd. *New York: Cold Spring Harbor Laboratory* 18, 58 (1989).
40. Sansonetti P. J. et al—Involvement of a plasmid in the invasive ability of *Shigella flexneri*—Infection and Immunity, March 1982, p. 852-860.

The invention claimed is:

1. A process of assessing gene expression in a cell or in a cell line wherein the assessed gene is an endogenous gene, comprising:
   (a) providing a cell or cell line wherein a double-stranded polynucleotide construct has been introduced, which double-stranded polynucleotide construct is suitable for performing gene expression assay when integrated into a cell which naturally harbours and expresses gene(s) of interest for an activity, and which comprises on its positive strand considered from its 5' end to its 3' end, (i) a promoter of a gene of interest or several promoters of various genes of interest selected among genes which are endogenous to the cell and subject to gene transcription profiling, wherein said promoter is recognized by the internal transcription machinery of the cell, and, (ii) one or several beacon barcode(s) wherein each barcode contains at least one barcode unit which is a DNA construct comprising tandem repeats of at least one beacon recognition binding site each binding site being composed of a nucleotide sequence, and wherein each of said barcode(s) is(are) under the control of one of said at least one promoter(s) for transcription,
   (b) eliciting, silencing or modulating transcription of the polynucleotide construct
   (c) contacting the cell or cell line of step (a) with detection probe(s) capable of hybridizing with the beacon recognition binding site(s) of the barcode(s) and which is (are) one or several molecular beacon(s), said molecular beacon(s) having a stem-and-loop polynucleotide structure and being suitable for visualisation or measurement when hybridized to their target sequence, wherein the visualisation of the hybridization of the detection probe(s) with their target is obtained as a result of fluorescence which is switched on when the detection probe binds to its target sequence,
   (d) detecting hybridization between the detection probes and the transcript of the beacon recognition binding sites of the barcode as a reporter of transcription activity of the promoter of the polynucleotide construct,
   (e) measuring gene expression in the cell or in the cell line of step (a) on the transcriptional level, by quantifying in vivo hybridization events of the molecular beacon(s) with the transcript of the polynucleotide construct resulting in an increase in fluorescence obtained in step (c) over the signal of said molecular beacon(s) not hybridized to their target sequence.

2. The process according to claim 1, wherein the step of eliciting, silencing or modulating the transcription is obtained after contacting the cell or cell line with an external factor.

3. The process according to claim 2, wherein the external factor is provided as a library of compounds or a library of organisms, to the cell or cell line.

4. The process according to any of claims 1 to 3, wherein the process is performed on a single cell.

5. The process according to any of claims 1 to 3, wherein gene expression of a single gene is assessed.

6. The process according to any of claims 1 to 3, wherein gene expression of multiple genes from a single cell is assessed.

7. The process according to any one of claims 1 to 3, wherein transcription of the polynucleotide construct is studied in real-time and/or at an end point.

8. The process according to any of claims 1 to 3, wherein detection of the hybridization between the detection probe and the transcript of the beacon recognition binding sites of the barcode(s) is quantitative.

9. The process according to any of claims 1 to 3, wherein the transcription activity of 1 to 4, or 1 to 10, or 1 to 15, or 1 to 32 gene promoters is detected as a result of a measurable change resulting from hybridization between the molecular beacons and the transcript of the beacon recognition binding sites of the barcode, allowing a fluorescence emission.

10. The process according to any of claims 1 to 3, which further comprises the detection of an expressed reporter protein encoded by the polynucleotide construct and expressed under the control of one of the promoter(s) contained in the polynucleotide construct.

11. The process according to any of claims 1 to 3, wherein the promoter contained in the polynucleotide sequence is selected from the group of promoters of genes involved in the immune response, promoters of chemokine or cytokines genes, or promoters of cell adhesion molecules genes such as ICAM genes, promoters of interferon gene, or is selected from promoters of genes encoding tumor associated proteins.

12. The process according to claim 10, wherein the polynucleotide expresses a reporter selected from the group consisting of Green Fluorescent Protein (GFP), luciferase, and SYBR green.

13. The process according to claim 1, comprising a step of screening an RNAi library, a DNA library, a chemical library or a library of pathogen organisms based on the results of step (e).

14. The process according to claim 1, comprising diagnosing a disease state or an infection state based on the results of step (e).

15. The process according to claim 1, comprising following up the outcome of a therapeutic treatment based on the results of step (e), said results being determined after administration of a drug.

16. The process according to claim 1, comprising screening putative therapeutic compounds based on the results of step (e).

17. The process according to claim 1, comprising screening compounds possibly interacting with the immune response based on the results of step (e).

18. The process according to claim 1, comprising a step of monitoring the interactions between a pathogen and a host, at the level of a cell of the host or of a cell derived from said cell, optionally when said cell is placed in conditions of being infected with said pathogen, based on the results of step (e).

19. The process according to claim 1, comprising a step of investigating cellular targets of a compound or of a pathogen organism or agent based on the results of step (e).

20. The process according to claim 1, wherein in the polynucleotide, one beacon recognition binding site has one of the following sequences:

(SEQ ID NO: 1)
5'-TTCTCTTCAAACTTTTCCGCTTTT-3', or (SEQ ID NO: 2)
5'-CGCCAAAACCTATTATCTTAAGTC-3', or (SEQ ID NO: 3)
5'-CTCACCTGCTCTTCTCAGACC-3' and (SEQ ID NO: 4)
5'-GCTATAGCACTAAGGTAAGACCC-3' and/or the molecular beacons have one of the following nucleotide sequences:

(SEQ ID NO: 5)
5'-GCUGC AAAAGCGGAAAAGUUUGAAGAGAA GCAGC-3' or (SEQ ID NO: 6)
5'-CGACC GACUUAAGAUAAUAGGUUUUGGCG GGUCG-3'.

21. The process according to claim 20, wherein the molecular beacon of the detection probe is a stem-and-loop polynucleotide structure wherein the loop portion of the polynucleotide is the probe sequence suitable to hybridize specifically to a beacon binding site and the stem portion consists of two arms formed of sequences complementary to each other, each of the arm sequence harbouring, attached to its free extremity which is adverse to the loop portion of the polynucleotide, one of either a fluorescent moiety or a non-fluorescent quenching moiety wherein said moieties, when attached to said arm sequences, are sufficiently close to each other to cause the fluorescence of the fluorescent moiety to be quenched by fluorescence resonance energy transfer, and further said loop portion of the polynucleotide is at least twice longer in nucleotides than each arm polynucleotide structure.

22. The process according claim 21, wherein the fluorescent moiety (fluorophore) is selected from the group consisting of Quantum Dots and derivatives, Alexafluor family of dyes, FAM, TET or CAL FluorGold 540, HEX or JOE, VIC$^B$, CAL Fluor Orange 560$^A$; Cy3$^C$ or NED$^B$, Quasar 570$^A$, Oyster 556$^D$; TMR or CAL Fluor Red 590$^A$; ROX or LC red 610$^E$, CAL FLuor Red 610$^A$; Texas red or LC red 610$^E$, CAL Fluor Red 610$^A$; LC red 640$^E$ or CAL Fluor Red 635$^A$; Cy5$^C$ or LC red 670$^E$, Quasar 670$^A$, Oyster 645$^D$; LC red 705$^E$ or Cy5.5$^C$ or 5-(2'-aminoethyl)aminonaphthalene-1-sulfonic acid (EDANS), fluorescein, anthranilamide, coumarin, and terbium chelates, and wherein the quencher is selected from the group consisting of DDQ-I$^A$ (absorption max 430 μm), Dabcyl (absorption max 475), Eclipse$^B$ (absorption max 530), Iowa Black FQ$^C$ (absorption max 532), BHQ-1$^D$ (absorption max 534), QSY-7$^E$ (absorption max 571), BHQ-2$^D$ (absorption max 580), DDQ-II$^A$ (absorption max 630), Iowa Black RQ$^C$ (absorption max 645), QSY-21$^E$ (absorption max 660), BHQ-3$^D$ (absorption max 670), Gold, Rare Earth Metals or 4-(4'-dimethylaminophenylazo)benzoic acid (DABCYL), rhodamin, pyrenebutyrate, eosine, nitrotyrosine, ethidium and tetramethylrhodamine.

* * * * *